(12) United States Patent
Kircher et al.

(10) Patent No.: US 10,888,227 B2
(45) Date of Patent: *Jan. 12, 2021

(54) RAMAN-TRIGGERED ABLATION/RESECTION SYSTEMS AND METHODS

(71) Applicant: Memorial Sloan Kettering Cancer Center, New York, NY (US)

(72) Inventors: Moritz Kircher, New York, NY (US); Ricardo Toledo-Crow, New York, NY (US)

(73) Assignee: Memorial Sloan Kettering Cancer Center, New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 14/464,642

(22) Filed: Aug. 20, 2014

(65) Prior Publication Data

US 2015/0018807 A1 Jan. 15, 2015

Related U.S. Application Data

(63) Continuation-in-part of application No. PCT/US2014/017508, filed on Feb. 20, 2014.
(Continued)

(51) Int. Cl.
*A61B 5/00* (2006.01)
*G01N 21/65* (2006.01)
(Continued)

(52) U.S. Cl.
CPC ........ *A61B 5/0075* (2013.01); *A61B 1/00087* (2013.01); *A61B 5/0084* (2013.01); *A61B 5/7425* (2013.01); *A61B 5/7445* (2013.01); *A61B 18/02* (2013.01); *A61B 18/12* (2013.01); *A61B 18/20* (2013.01); *A61M 5/007* (2013.01); *A61M 31/005* (2013.01); *G01N 21/65* (2013.01);
(Continued)

(58) Field of Classification Search
CPC .............................. A61B 5/0075; A61B 18/20
USPC .......................................................... 606/12
See application file for complete search history.

(56) References Cited

U.S. PATENT DOCUMENTS 4,127,329 A 11/1978 Chang et al.
4,604,992 A 8/1986 Sato
(Continued)

FOREIGN PATENT DOCUMENTS

CN 101679022 A 3/2010
CN 102015020 A 4/2011
(Continued)

OTHER PUBLICATIONS

Dick Wieboldt, Understanding Raman Spectrometer Parameters, Jun. 1, 2010, Spectroscopy, Special Issues.*
(Continued)

*Primary Examiner* — Jonathan T Kuo
(74) *Attorney, Agent, or Firm* — Wolf, Greenfield & Sacks, P.C.

(57) ABSTRACT

Apparatus and methods are presented herein that permit real-time, accurate detection of residual tumor in the operating room. The Raman-based wide-field imaging apparatus and methods described herein permit real-time imaging of tumor-targeted R-MR nanoparticles over a wide field. Apparatus and methods are presented herein for operating a Raman-based resection system.

28 Claims, 35 Drawing Sheets

Related U.S. Application Data

(60) Provisional application No. 61/767,241, filed on Feb. 20, 2013, provisional application No. 61/834,854, filed on Jun. 13, 2013.

(51) Int. Cl.

| | |
|---|---|
| *A61B 18/20* | (2006.01) |
| *A61B 1/00* | (2006.01) |
| *A61B 18/02* | (2006.01) |
| *A61B 18/12* | (2006.01) |
| *A61M 5/00* | (2006.01) |
| *A61M 31/00* | (2006.01) |
| *A61B 90/00* | (2016.01) |
| *A61B 18/00* | (2006.01) |

(52) U.S. Cl.
CPC ........... *A61B 2018/00577* (2013.01); *A61B 2018/00595* (2013.01); *A61B 2018/00642* (2013.01); *A61B 2090/3937* (2016.02); *A61B 2218/007* (2013.01); *A61B 2576/00* (2013.01)

(56) References Cited

U.S. PATENT DOCUMENTS

| | | | |
|---|---|---|---|
| 4,669,467 A | 6/1987 | Willett et al. | |
| 4,938,205 A | 7/1990 | Nudelman | |
| 5,275,594 A | 1/1994 | Baker et al. | |
| 5,293,872 A | 3/1994 | Alfano et al. | |
| 5,300,097 A | 4/1994 | Lerner et al. | |
| 5,306,403 A | 4/1994 | Vo-Dinh | |
| 5,491,510 A | 2/1996 | Gove | |
| 5,594,497 A | 1/1997 | Ahern et al. | |
| 5,609,907 A | 3/1997 | Natan | |
| 5,713,364 A | 2/1998 | DeBaryshe et al. | |
| 5,721,102 A | 2/1998 | Vo-Dinh | |
| 5,813,987 A | 9/1998 | Modell et al. | |
| 5,949,388 A | 9/1999 | Atsumi et al. | |
| 6,002,471 A | 12/1999 | Quake | |
| 6,006,126 A | 12/1999 | Cosman | |
| 6,008,889 A | 12/1999 | Zeng et al. | |
| 6,019,719 A | 2/2000 | Schulz et al. | |
| 6,025,202 A | 2/2000 | Natan | |
| 6,127,120 A | 10/2000 | Graham et al. | |
| 6,174,291 B1 | 1/2001 | McMahon et al. | |
| 6,174,677 B1 | 1/2001 | Vo-Dinh | |
| 6,219,137 B1 | 4/2001 | Vo-Dinh | |
| 6,228,076 B1 | 5/2001 | Winston et al. | |
| 6,242,264 B1 | 6/2001 | Natan et al. | |
| 6,251,127 B1 | 6/2001 | Biel | |
| 6,254,852 B1 | 7/2001 | Glajch et al. | |
| 6,514,767 B1 | 2/2003 | Natan | |
| 6,579,726 B1 | 6/2003 | Natan et al. | |
| 6,624,886 B2 | 9/2003 | Natan et al. | |
| 6,640,130 B1 | 10/2003 | Freeman et al. | |
| 6,788,860 B1 | 9/2004 | Treado et al. | |
| 6,959,024 B2 | 10/2005 | Paldus et al. | |
| 7,076,092 B2 | 7/2006 | Hollars et al. | |
| 7,192,778 B2 | 3/2007 | Natan | |
| 7,443,489 B2 | 10/2008 | Natan | |
| 7,538,859 B2 | 5/2009 | Tearney et al. | |
| 7,656,525 B2 | 2/2010 | Zhao et al. | |
| 7,738,096 B2 | 6/2010 | Zhao et al. | |
| 7,760,352 B2 | 7/2010 | Armstrong et al. | |
| 7,826,176 B2 | 11/2010 | Shirotori et al. | |
| 7,829,140 B1 | 11/2010 | Zhong et al. | |
| 8,054,463 B2 | 11/2011 | Morris et al. | |
| 8,320,650 B2 | 11/2012 | Demos et al. | |
| 8,409,862 B2 | 4/2013 | Caulfield et al. | |
| 8,409,863 B2 | 4/2013 | Natan et al. | |
| 8,416,405 B2 | 4/2013 | Panza et al. | |
| 8,497,131 B2 | 7/2013 | Natan et al. | |
| 8,568,878 B2 | 10/2013 | Wilson et al. | |
| 8,771,978 B2 | 7/2014 | Ragan | |
| 8,795,628 B2 | 8/2014 | Gambhir et al. | |
| 8,918,161 B2 | 12/2014 | Natan et al. | |
| 9,086,533 B1 | 7/2015 | Wach | |
| 9,295,391 B1 | 3/2016 | Tearney et al. | |
| 9,314,849 B2 | 4/2016 | Tracy et al. | |
| 9,561,292 B1* | 2/2017 | Vo-Dinh | A61K 41/0057 |
| 9,789,154 B1 | 10/2017 | Vo-Dinh et al. | |
| 9,833,144 B2 | 12/2017 | Kircher | |
| 10,105,456 B2 | 10/2018 | Harmsen et al. | |
| 10,322,194 B2 | 6/2019 | Kircher | |
| 2002/0045266 A1 | 4/2002 | Fenniri | |
| 2002/0082498 A1 | 6/2002 | Wendt et al. | |
| 2002/0163482 A1 | 11/2002 | Sullivan | |
| 2002/0165594 A1 | 11/2002 | Biel | |
| 2003/0055307 A1 | 3/2003 | Elmaleh et al. | |
| 2003/0191379 A1 | 10/2003 | Benaron et al. | |
| 2003/0201208 A1 | 10/2003 | Koch et al. | |
| 2004/0009341 A1 | 1/2004 | Naasani | |
| 2004/0010192 A1 | 1/2004 | Benaron et al. | |
| 2004/0073120 A1 | 4/2004 | Motz et al. | |
| 2004/0225222 A1 | 11/2004 | Zeng et al. | |
| 2004/0254419 A1 | 12/2004 | Wang et al. | |
| 2004/0254454 A1 | 12/2004 | Kockro | |
| 2005/0014851 A1 | 1/2005 | Bringley | |
| 2005/0074779 A1 | 4/2005 | Vo-Dinh | |
| 2005/0143662 A1 | 6/2005 | Marchitto et al. | |
| 2005/0221494 A1 | 10/2005 | Natan | |
| 2005/0272160 A1 | 12/2005 | Natan | |
| 2005/0277816 A1 | 12/2005 | Maier et al. | |
| 2006/0008924 A1 | 1/2006 | Anker et al. | |
| 2006/0054506 A1 | 3/2006 | Natan et al. | |
| 2006/0098194 A1 | 5/2006 | Tuschel | |
| 2006/0173293 A1 | 8/2006 | Marquart et al. | |
| 2006/0250613 A1 | 11/2006 | Demuth et al. | |
| 2007/0010809 A1 | 1/2007 | Hovda et al. | |
| 2007/0134805 A1 | 6/2007 | Gilbert | |
| 2007/0167838 A1 | 7/2007 | Hubble et al. | |
| 2007/0178067 A1* | 8/2007 | Maier | G01N 21/65 424/93.2 |
| 2007/0196281 A1 | 8/2007 | Jin et al. | |
| 2007/0232874 A1 | 10/2007 | Ince | |
| 2007/0238953 A1 | 10/2007 | Lucassen et al. | |
| 2007/0255356 A1 | 11/2007 | Rose et al. | |
| 2007/0260295 A1 | 11/2007 | Chen et al. | |
| 2007/0269382 A1 | 11/2007 | Santra et al. | |
| 2007/0282190 A1 | 12/2007 | Dekel et al. | |
| 2007/0299550 A1 | 12/2007 | Nishijima et al. | |
| 2008/0007716 A1 | 1/2008 | Igarashi | |
| 2008/0058908 A1 | 3/2008 | Bornstein | |
| 2008/0089839 A1 | 4/2008 | Lu et al. | |
| 2008/0095852 A1 | 4/2008 | Kong | |
| 2008/0118912 A1 | 5/2008 | Dickson et al. | |
| 2008/0119832 A1 | 5/2008 | Cronin | |
| 2008/0295646 A1 | 12/2008 | Mirkin et al. | |
| 2008/0305045 A1 | 12/2008 | Kuniyil et al. | |
| 2009/0137666 A1 | 5/2009 | Wang et al. | |
| 2009/0171330 A1 | 7/2009 | Taylor et al. | |
| 2009/0204111 A1 | 8/2009 | Bissig et al. | |
| 2009/0218550 A1 | 9/2009 | Koyakutty et al. | |
| 2009/0237648 A1 | 9/2009 | Armstrong et al. | |
| 2009/0263485 A1 | 10/2009 | Li et al. | |
| 2009/0281536 A1* | 11/2009 | Beckman | A61B 5/0059 606/33 |
| 2009/0285766 A1 | 11/2009 | Kishen et al. | |
| 2009/0294692 A1 | 12/2009 | Bourke, Jr. et al. | |
| 2009/0304581 A1 | 12/2009 | Scheinberg et al. | |
| 2010/0016783 A1 | 1/2010 | Bourke, Jr. et al. | |
| 2010/0045778 A1 | 2/2010 | Yelin | |
| 2010/0166650 A1* | 7/2010 | Gambhir | G01N 21/658 424/1.11 |
| 2010/0197937 A1 | 8/2010 | Minami et al. | |
| 2010/0211137 A1 | 8/2010 | Kim et al. | |
| 2010/0233147 A1 | 9/2010 | Schwartz et al. | |
| 2010/0255599 A1 | 10/2010 | Drake et al. | |
| 2010/0279272 A1 | 11/2010 | Burrell et al. | |
| 2010/0322471 A1 | 12/2010 | Treado et al. | |
| 2011/0020239 A1 | 1/2011 | Bulte et al. | |
| 2011/0021970 A1 | 1/2011 | Vo-Dinh et al. | |
| 2011/0045081 A1 | 2/2011 | Steitz et al. | |
| 2011/0123439 A1 | 5/2011 | Cheon et al. | |

(56) References Cited

U.S. PATENT DOCUMENTS

| | | |
|---|---|---|
| 2011/0152692 A1 | 6/2011 | Nie et al. |
| 2011/0165077 A1 | 7/2011 | Qian et al. |
| 2011/0182881 A1 | 7/2011 | Chin et al. |
| 2011/0189483 A1 | 8/2011 | Zubarev et al. |
| 2011/0190760 A1 | 8/2011 | Niver et al. |
| 2011/0207231 A1 | 8/2011 | Natan et al. |
| 2011/0230760 A1 | 9/2011 | Gambhir et al. |
| 2011/0242533 A1 | 10/2011 | Treado et al. |
| 2011/0261351 A1 | 10/2011 | Treado et al. |
| 2011/0262351 A1 | 10/2011 | Chung et al. |
| 2011/0263920 A1 | 10/2011 | Bourke, Jr. et al. |
| 2011/0282181 A1 | 11/2011 | Wang et al. |
| 2012/0123205 A1 | 5/2012 | Nie et al. |
| 2012/0136241 A1 | 5/2012 | Chen et al. |
| 2012/0141380 A1 | 6/2012 | Margel et al. |
| 2012/0141981 A1 | 6/2012 | Pantazis et al. |
| 2012/0164624 A1 | 6/2012 | Natan et al. |
| 2012/0164680 A1 | 6/2012 | McNaughton et al. |
| 2012/0179029 A1 | 7/2012 | Kircher et al. |
| 2012/0212733 A1 | 8/2012 | Kodali et al. |
| 2012/0226139 A1 | 9/2012 | Peyman |
| 2012/0251450 A1 | 10/2012 | Punnoose et al. |
| 2012/0282632 A1 | 11/2012 | Chiu et al. |
| 2012/0283336 A1 | 11/2012 | Grigorenko et al. |
| 2012/0283379 A1 | 11/2012 | Auger et al. |
| 2012/0302940 A1 | 11/2012 | Ray |
| 2013/0012794 A1 | 1/2013 | Zeng et al. |
| 2013/0023770 A1 | 1/2013 | Courtney et al. |
| 2013/0029360 A1 | 1/2013 | Suh et al. |
| 2013/0040292 A1 | 2/2013 | Fernandez Lopez et al. |
| 2013/0137944 A1 | 5/2013 | Jeong et al. |
| 2013/0164842 A1 | 6/2013 | Ujihara et al. |
| 2013/0231573 A1 | 9/2013 | Zeng et al. |
| 2013/0309280 A1 | 11/2013 | Choi et al. |
| 2013/0330839 A1 | 12/2013 | Suh et al. |
| 2013/0342683 A1 | 12/2013 | Nelson et al. |
| 2014/0140594 A1 | 5/2014 | Mahadevan-Jansen et al. |
| 2014/0316255 A1 | 10/2014 | Garai et al. |
| 2014/0329089 A1 | 11/2014 | Yin et al. |
| 2014/0350534 A1* | 11/2014 | Kircher ............... A61B 18/203 606/10 |
| 2015/0125952 A1 | 5/2015 | Kim et al. |
| 2015/0182296 A1 | 7/2015 | Daon et al. |
| 2015/0258218 A1 | 9/2015 | Kircher et al. |
| 2015/0328346 A1 | 11/2015 | Harmsen et al. |
| 2016/0000329 A1* | 1/2016 | Kircher ............... G01N 21/65 600/431 |
| 2016/0000330 A1 | 1/2016 | Huang et al. |
| 2016/0018404 A1 | 1/2016 | Iyer et al. |
| 2016/0166194 A1 | 6/2016 | Gareau et al. |
| 2016/0367668 A1 | 12/2016 | Kircher et al. |
| 2017/0138860 A1 | 5/2017 | Huang |
| 2017/0266328 A1 | 9/2017 | Wall et al. |
| 2017/0296293 A1 | 10/2017 | Mak et al. |
| 2018/0193910 A1 | 7/2018 | Kircher |
| 2018/0271502 A1 | 9/2018 | Zarrine-Afsar |

FOREIGN PATENT DOCUMENTS

| | | |
|---|---|---|
| CN | 102175655 A | 9/2011 |
| CN | 102410994 A | 4/2012 |
| CN | 102686181 A | 9/2012 |
| CN | 102770071 A | 11/2012 |
| CN | 102559190 B | 9/2013 |
| CN | 104551012 A | 4/2015 |
| DE | 102 49 674 A1 | 5/2004 |
| DE | 102005030986 A1 | 1/2007 |
| DE | 10 2011 103 950 A1 | 12/2012 |
| EP | 2671613 A2 | 12/2013 |
| JP | H09-005666 A | 1/1997 |
| JP | H11-084307 A | 3/1999 |
| JP | 2002-534199 A | 10/2002 |
| JP | 2003/503135 A | 1/2003 |
| JP | 2004/193545 A | 7/2004 |
| JP | 2005 306827 A | 11/2005 |
| JP | 2009/011546 A | 1/2009 |
| JP | 2009/508571 A | 3/2009 |
| JP | 2009/511891 A | 3/2009 |
| JP | 2009/115546 A | 5/2009 |
| JP | 2009/222713 A | 10/2009 |
| JP | 2010/523983 A | 7/2010 |
| JP | 2011-158334 A | 8/2011 |
| TW | 572748 B | 1/2004 |
| WO | WO 1990/003803 A1 | 4/1990 |
| WO | WO-93/03672 A1 | 3/1993 |
| WO | WO-00/41611 A2 | 7/2000 |
| WO | WO-01/01854 A2 | 1/2001 |
| WO | WO 2001/081923 A1 | 11/2001 |
| WO | WO-02/100285 A1 | 12/2002 |
| WO | WO-2005/107623 A2 | 11/2005 |
| WO | WO-2008/122035 A1 | 10/2008 |
| WO | WO-2010/096828 A1 | 8/2010 |
| WO | WO-2010/111066 A2 | 9/2010 |
| WO | WO-2011/025640 A1 | 3/2011 |
| WO | WO-2011/084528 A1 | 7/2011 |
| WO | WO-2012/065163 A2 | 5/2012 |
| WO | WO 2012070893 A2 * | 5/2012 |
| WO | WO 2012/166796 A1 | 12/2012 |
| WO | WO 2013/128458 A1 | 9/2013 |
| WO | WO-2014/036470 A1 | 3/2014 |
| WO | WO-2014/089247 A2 | 6/2014 |
| WO | WO-2014/100380 A2 | 6/2014 |
| WO | WO-2014/130736 A1 | 8/2014 |
| WO | WO 2015/134620 A1 | 9/2015 |
| WO | WO-2016/028749 A1 | 2/2016 |
| WO | WO-2016/149378 A1 | 9/2016 |
| WO | WO-2016/179260 A1 | 11/2016 |
| WO | WO 2017/040915 A1 | 3/2017 |
| WO | WO-2018/213851 A1 | 11/2018 |

OTHER PUBLICATIONS

Kircher, Moritz F., et al. "A brain tumor molecular imaging strategy using a new triple-modality MRI-photoacoustic-Raman nanoparticle." Nature medicine 18.5 (2012): 829-834. doi:10.1038/nm.2721.*

Adiseshaiah, P.P. et al., Nanomaterial standards for efficacy and toxicity assessment, Advanced Review, 2:99-112 (2009).

Agarwal, A. et al., Targeted gold nanorod contrast agent for prostate cancer detection by photoacoustic imaging, Journal of Applied Physics, 102:064701-064704 (2007).

Aggarwal, S. et al., What's fueling the biotech engine-2009-2010, Nature Biotechnology, 28(11):1165-1171 (2010).

Beljebbar, A. et al., Ex vivo and in vivo diagnosis of C6 glioblastoma development by Raman spectroscopy coupled to a microprobe, Anal Bioanal Chem, 398:477-487 (2010).

Binkley, J. et al., RNA ligands to human nerve growth factor, Nucleic Acids Research, 23(16):3198-3205 (1995).

Bucci, M.K. et al., Near Complete Surgical Resection Predicts a Favorable Outcome in Pediatric Patients with Nonbrainstem, Malignant Gliomas, Cancer, 101(4): 817-824 (2004).

De La Zerda, A. et al., A Comparison Between Time Domain and Spectral Imaging Systems for Imaging Quantum Dots in Small Living Animals, Molecular Imaging and Biology, 12:500-508 (2010).

De La Zerda, A. et al., Advanced contrast nanoagents for photoacoustic molecular imaging, cytometry, blood test and photothermal theranostics, Contrast Media Mol. Imaging, 6:346-369 (2011).

De La Zerda, A. et al., Carbon nanotubes as photoscoustic molecular imaging agents in living mice, Letters, Nature Nanotechnology, 3:557-562 (2008).

De La Zerda, A. et al., Ultrahigh Sensitivity Carbon Nanotube Agents for Photoacoustic Molecular Imaging in Living Mice, Nano Letters, 10:2168-2172 (2010).

Eghtedari, M. et al., High Sensitivity of In Vivo Detection of Gold Nanorods Using a Laser Optoacoustic Imaging System, Nano Letters, 7(7):1914-1918 (2007).

Ermilov, S.A. et al., Laser optoacoustic imaging system for detection of breast cancer, Journal of Biomedical Optics, 14(2):024007-1-14 (2009).

(56) References Cited

OTHER PUBLICATIONS

Haaland, D.M. and Easterling, R.G., Improved Sensitivity of Infrared Spectroscopy by the Application of Least Squares Methods, Applied Spectroscopy, 34(5):539-548 (1980).
Jellinek, D.J. et al., Inhibition of Receptor Binding by High-Affinity RNA Ligands to Vascular Endothelial Growth Factor, Biochemistry, 33:10450-10456 (1994).
Kantelhardt, S.R. et al., Multiphoton Excitation Fluorescence Microscopy of 5-Aminolevulinic Acid Induced Fluorescence in Experimental Gliomas, Laser in Surgery and Medicine, 40:273-281 (2008).
Keren, S. et al., Noninvasive molecular imaging of small living subjects using Raman spectroscopy, PNAS, 105(15):5844-5849 (2008).
Kim, G. et al., Indocyanine-green-embedded PEBBLEs as a contrast agent of photoacoustic imaging, Journal of Biomedical Optics, 12(4):044020-1-8 (2007).
Kim, J. et al., Golden carbon nanotubes as multimodal photoacoustic and photothermal high-contrast molecular agents, Nature Nanotechnology, 4:688-694 (2009).
Kircher, M.F. et al., A brain tumor molecular imaging strategy using a new triple-modality MRI-photoacoustic-Raman nanoparticle, Nature Medicine, 18(5):829-834 (2012).
Kircher, M.F. et al., Noninvasive cell-tracking methods, Nature Reviews: Clinical Oncology, 8:677-688 (2011).
Knauth, M. et al., Low-field interventional MRI in neurosurgery: finding the right dose of contrast medium, Neuroradiology, 43:254-258 (2001).
Knauth, M. et al., Surgically Induced Intracranial Contrast Enhancement: Potential Source of Diagnostic Error in Intraoperative MR Imaging, AJNR Am J Neuroradiol, 20:1547-1553 (1999).
Koljenovic, S. et al., Raman Spectroscopic Characterization of Porcine Brain Tissue Using a Single Fiber-Optoic Probe, Anal. Chem., 79:557-564 (2007).
Loening, A.M. and Gambhir, S.S., Amide: A Free Software Tool for Multimodality Medical Image Analysis, Molecular Imaging, 2(3):131-137 (2003).
Lüdemann, L. et al., Pharmacokinetic analysis of glioma compartments with dynamic Gd-DTPA-enhanced magnetic resonance imaging, Magnetic Resonance Imaging, 18:1201-1214 (2000).
Maeda, H. et al., Tumor vascular permeability and the EPR effect in macromolecular therapeutics: a review, Journal of Controlled Release, 65:271-284 (2000).
Mansfield, J.R. et al., Autofluorescence removal, multiplexing, and automated analysis methods for in-vivo fluorescence imaging, Journal of Biomedical Optics, 10(4):041207-1-9 (2005).
McNay, G. et al., Surface-Enhanced Raman Scattering (SERS) and Surface-Enhanced Resonance Raman Scattering (SERRS): A Review of Applications, Applied Spectroscopy, 65(8):825-837 (2011).
Ozawa, T. et al., Bromophenol Blue Staining of Tumors in a Rat Glioma Model, Neurosurgey, 57(4):1041-1047 (2005).
Pelletier, M.J., Quantitative Analysis Using Raman Spectrometry, 57(1):20A-42A (2003).
Razansky, D. et al., Multispectral opto-acoustic tomography of deep-seated fluorescent proteins in vivo, Nature Photonics, 3:412-417 (2009).
Reinges, M.H.T. et al., Course of brain shift during microsurgical resection of supratentorial cerebral lesions: limits of conventional neuronavigation, Acta Neurochir, 146:369-377 (2004).
Robbins, S.L. and Angell, M., Neoplasia and Other Disturbances of Cell Growth, Basic Pathology: Non-Neoplastic Cell Growth, 2(3):68-105 (1976).
Schneider, J.P. et al., Intraoperative MRI to guide the resection of primary supratentorial glioblastoma multiforme-a quantitative radiological analysis, Neuroradiology, 47:489-500 (2005).
Shinoda, J. et al., Fluorescence-guided resection of glioblastoma multiforme by using high-dose fluorescein sodium, J Neurosurg, 99:597-603 (2003).
Short, M.A. et al., Development and preliminary results of an endoscopic Raman probe for potential in vivo diagnosis of lung cancers, Optics Letters, 33(7):711-713 (2008).
Stummer, W. et al., Fluorescence-guided surgery with 5-aminolevulinic acid for resection of malignant glioma: a randomised controlled multicentre phase III trial, Oncology: The Lancet, 7:392-401 (2006).
Stupp, R. et al., Changing Paradigms—An Upadate on the Multidisciplinary Management of Malignant Glioma, The Oncologist, 11:165-180 (2006).
Thakor, A.S. et al., Oxidative Stress Mediates the Effects of Raman-Active Gold Nanoparticles in Human Cells, Nanoparticle Cytotoxicity, 7(1):126-136 (2011).
Thakor, A.S. et al., The Fate and Toxicity of Raman-Active Silica-Gold Nanoparticles in Mice, Drug Delivery, Science Translation Medicine, 3(79):1-11 (2011).
Toms, S.A. et al., Intraoperative Optical Spectroscopy Identifies Infiltrating Glioma Margins with High Sensitivity, Operative Neurosurgery, 57(4):382-391 (2005).
Tréhin, R. et al., Fluorescent Nanoparticle Uptake for Brain Tumore Visualization, Neoplasia, 8(4):302-311 (2006).
Tuerk, C. and Macdougal-Waugh, S., In vitro evolution of functional nucleic acids: high-affinity RNA ligands of HIV-1 proteins, Gene, 137:33-39 (1993).
Wang, L.V., Multiscale photoacoustic microscopy and computed tomography, Nature Photonics, 3:503-209 (2009).
Yigit, M.V. and Medarova, Z., In vivo and ex vivo applications of gold nanoparticles for biomedical SERS imaging, Am J Nucl Med Mol Imaging, 2(2):232-341 (2012).
Zavaleta, C. et al., Noninvasive Raman Spectroscopy in Living Mice for Evaluation of Tumor Targeting with Carbon Nanotubes, Nano Letters, 8(9):2800-2805 (2008).
Zavaleta, C.L. et al., Multiplexed imaging of surface enhanced Raman scattering nanotags in living mice using noninvasive Raman spectroscopy, PNAS, 106(32):13511-13516 (2009).
Zavaleta, C.L. et al., Preclinical Evaluation of Raman Nanoparticle Biodistribution for their Potential Use in Clinical Endoscopy Imaging, Small, 7(15):2232-2240 (2011).
Zavaleta, C.L. et al., Raman's "Effect" on Molecular Imaging, J Nucl Med., 52:1839-1844 (2011).
Zhang, Y. et al., Molecular Imaging with SERS-Active Nanoparticles, Small, 7(23):3261-3269 (2011).
Harmsen, S. et al., Surface-enhanced resonance Raman scattering nanostars for high-precision cancer imaging, Science Translational Medicine, 7(271):1-8 (2015).
International Preliminary Report on Patentability, PCT/US2013/057636, dated Aug. 1, 2014, 27 pages.
International Search Report, PCT/US2014/017508, dated May 12, 2014, 3 pages.
International Search Report, PCT/US2013/057636, dated Jan. 3, 2014, 3 pages.
International Search Report, PCT/US2013/076475, dated Jun. 16, 2014, 4 pages.
Kim, J. et al., Multifunctional nanostructured materials for multimodal imaging, and simultaneous imaging and therapy, Chem. Soc. Rev., 38:372-390 (2009).
Stewart et al., Raman Imaging, Annual Review of Analytical Chemistry, 5:337-360 (2012).
Written Opinion, PCT/US2014/017508, dated May 12, 2014. 12 pages.
Written Opinion, PCT/US2013/057636, dated Jan. 3, 2014, 12 pages.
Written Opinion, PCT/US2013/076475, dated Jun. 16, 2014, 8 pages.
International Search Report, PCT/US2015/045646, dated Nov. 27, 2015, 5 pages.
Written Opinion, PCT/US2015/045646, dated Nov. 27, 2015. 7 pages.
Debbage, P. and Jaschke, W., Molecular imaging with nanoparticles: giant roles for dwarf actors, Histochem. Cell Biol., 130(5):845-75 (2008).
Fales, A.M. et al., Silica-coated gold nanostars for combined surface-enhanced Raman scattering (SERS) detection and singlet-oxygen generation: a potential nanoplatform for theranostics, Langmuir, 27(19):12186-90 (2011).
Harmsen, S. et al., Rational design of a chalcogenopyrylium-based surface-enhanced resonance Raman scattering nanoprobe with attomolar

(56) References Cited

OTHER PUBLICATIONS sensitivity, Nature Communications, 6:6570 | DOI: 10.1038/ncomms7570, pp. 1-9, Additional Information added, 8 pages.

Huang, R. et al., High Precision Imaging of Microscopic Spread of Blioblastoma with a Targeted Ultrasensitive SERRS Molecular Imaging Probe, Theranostics, 6(8):1075-1084 (2016).

Huang, X. et al., Gold nanoparticles: interesting optical properties and recent applications in cancer diagnostics and therapy, Nanomedicine, 2(5):681-693 (2007).

Lusic, H. and Grinstaff, M.W., X-ray-computed tomography contrast agents, Chem. Rev., 113(3):1641-66 (2013).

Massoud, T.F. and Gambhir, S.S., Molecular imaging in living subjects: seeing fundamental biological processes in a new light, Genes Dev., 17(5):545-80 (2003).

Qian, X. et al., In vivo tumor targeting and spectroscopic detection with surface-enhanced Raman nanoparticle tags, Nature Biotechnology, 26(1):83-90, (2008).

Shona, S. et al., Raman Imaging, Annu. Rev. Anal. Chem. 5:337-360 (2012).

Supplementary Partial European Search Report, European International Application No. 14753802.9, 8 pages, Oct. 20, 2016.

Esenturk, E. N. and Walker, A. R. H., Surface-enhanced Raman scattering spectroscopy via gold nanostars, Journal of Raman Spectroscopy, 40(1): 86-91 (2009).

Yi, Z. et al, Facile preparation of Au/Ag bimetallic hollow nanospheres and its application in surface-enhanced Raman scattering, Applied Surface Science, 258(1): 212-217 (2011).

Yigit, M. V. et al, Noninvasive MRI-SERS Imaging in Living Mice Using an Innately Bimodal Nanomaterial, ACS Nano, 5(2): 1056-1066 (2011).

Yuan, H. et al., Quantitative Surface-Enhanced Resonant Raman Scattering Multiplexing of Biocompatible Gold Nanostars for in Vitro and ex Vivo Detection, Analytical Chemistry, 85:208-212 (2012).

Zong, S. et al., A SERS and fluorescence dual mode cancer cell targeting probe based on silica coated Au@Ag core-shell nanorods, Talanta, 97:368-375 (2012).

Von Maltzahn, G. et al., SERS-Coded Gold Nanorods as a Multifunctional Platform for Densely Multiplexed Near-Infrared Imaging and Photothermal Heating, Adv. Mater., 21:3175-3180 (2009).

Von Maltzahn et al., SERS-Coded Gold Nanorods as a Multifunctional Platform for Densely Multiplexed Near-Infrared Imaging and Photothermal Heating, Advanced Materials, 21:3175-3180, (2009).

Extended European Search Report, dated Apr. 20, 2016, in connection with Application No. EP 13832980.0.

European Search Report, dated May 27, 2019, in connection with Application No. EP 14753802.9.

International Search Report and Written Opinion, dated Nov. 22, 2016, in connection with Application No. PCT/US2016/050090.

International Search Report and Written Opinion, dated May 27, 2015, in connection with Application No. PCT/US2015/018746.

International Search Report and Written Opinion, dated Oct. 19, 2015, in connection with Application No. PCT/US2015/042441.

International Preliminary Report on Patentability, dated Feb. 9, 2017, in connection with Application No. PCT/US2015/042441.

International Search Report and Written Opinion, dated Dec. 22, 2016, in connection with Application No. PCT/US2016/040250.

International Preliminary Report on Patentability, dated Jan. 2, 2018, in connection with Application No. PCT/US2016/040250.

Ahmed et al., Principles of and Advances in Percutaneous Ablation. Radiology. Feb. 2011; 258(2):351-369.

Akbari et al., Cancer detection using infrared hyperspectral imaging. Cancer Sci. Apr. 2011;102(4):852-7. doi: 10.1111/j.1349-7006.2011.01849.x. Epub Feb. 11, 2011.

Akerman et al., Nanocrystal targeting in vivo. Proc Natl Acad Sci U S A. Oct. 1, 2002;99(20):12617-21. Epub Sep. 16, 2002.

Amstad et al., Triggered Release from Liposomes through Magnetic Actuation of Iron Oxide Nanoparticle Containing Membranes. Nano Letters. Apr. 13, 2011;11(4):1664-70.

Asfari et al., Establishment of 2- Mercaptoethanol-Dependent Differentiated Insulin-Secreting Cell Lines. Endocrinology. Jan. 1, 1992;130(1):167-178.

Bekis et al., A new agent for sentinel lymph node detection: preliminary results. J Radioanal. Nucl. Chem. Nov. 1, 2011;290(2):277-82. doi: 10.1007/s10967-011-1250-4.

Bogart et al., Photothermal Microscopy of the Core of Dextran-Coated Iron Oxide Nanoparticles During Cell Uptake. ACS Nano. Jul. 24, 2012;6(7):5961-71.

Burckhardt et al., Virus Movements on the Plasma Membrane Support Infection and Transmission between Cells. PLoS Pathogens. Nov. 2009;5(11):e1000621 :1-9.

Chen et al., Chelator-free synthesis of a dual-modality PET/MRI agent. Angew Chem Int Ed Engl. Dec. 9, 2013;52(50):13319-23. doi: 10.1002/anie.201306306. Epub Oct. 24, 2013.

Cho et al., A magnetic switch for the control of cell death signaling in in vitro and in vivo systems. Nat. Mater. Dec. 2012;11(12):1038-43.

Cirman et al., Selective Disruption of Lysosomes in Hela Cella Triggers Apoptosis Mediated by Cleavage of Bid by Multiple Papain-Like Lysosomal Cathepsins. J. of Biological Chem. Jan. 30, 2004;279(5):3578-3587.

Corchero et al., Biomedical applications of distally controlled magnetic nanoparticles. Trends Biotechnol. Aug. 2009;27(8):468-476.

Creixell et al., EGFR-Targeted Magnetic Nanoparticle Heaters Kill Cancer Cells without a Perceptible Temperature Rise. ACS Nano. Sep. 27, 2011;5(9):7124-7129.

Daniel et al., Lysosomal trapping as an important mechanism involved in the cellular distribution of perazine and in pharmacokinetic interaction with antidepressants. European Neuropsychopharmacology. Dec. 1, 1991;9(6):483-491.

Declaration of Moritz Kircher for U.S. Appl. No. 14/464,642, 16 pages, executed Dec. 5, 2016.

Dobson, Remote control of cellular behaviour with magnetic nanoparticles. Nature Nanotechnology. Mar. 2008;3(3):139-143.

Domenech et al., Lysosomal Membrane Permeabilization by Targeted Magnetic Nanoparticles in Alternating Magnetic Fields. ACS Nano. Jun. 25, 2013;7(6):5091-5101.

El-Dakdouki et al., Development of Multifunctional Hyaluronan-Coated Nanoparticles for Imaging and Drug Delivery to Cancer Cells. Biomacromolecules. Apr. 9, 2012;13(4):1144-1151.

Eto et al., Glucose metabolism and glutamate analog acutely alkalinize pH of insulin secretory vesicles of pancreatic beta-cells. Am. J. Physiol. Endocrinol. Metab. Aug. 2003;285(2):E262-E271.

Gaster et al., Matrix-insensitive protein assays push the limits of biosensors in medicine. Nature Medicine. Nov. 2009;15(11):1327-1332.

Ghosh et al., M13-templated magnetic nanoparticles for targeted in vivo imaging of prostate cancer. Nat. Nanotechnol. Oct. 2012;7(10):677-682.

Grimm et al., Cell Tracking. Principles and Applications. Radiologe. Jan. 1, 2007;47(1):25-33.

Grüttner et al., Synthesis and antibody conjugation of magnetic nanoparticles with improved specific power absorption rates for alternating magnetic field cancer therapy. J Magnetism and Magnetic Materials. Apr. 1, 2007;311(1):181-186.

Guo et al., Multifunctional superparamagnetic nanocarriers with folate-mediated and pH-responsive targeting properties for anticancer drug delivery. Biomaterials. Jan. 1, 2011;32(1):185-194.

Gupta et al., Cytotoxicity suppression and cellular uptake enhancement of surface modified magnetic nanoparticles. Biomaterials. May 1, 2005;26(13),:1565-1573.

Haun et al., Magnetic nanoparticle biosensors. Wiley Interdiscip Rev Nanomed Nanobiotechnol. May 2010;2(3):291-304.

Haun et al., Micro-NMR for Rapid Molecular Analysis of Human Tumor Samples. Science Translation Medicine. Feb. 23, 2011;3(71):1-13 with 2 additional pages of Editor's Summary.

Haun et al., Probing Intracellular Biomarkers and Mediators of Cell Activation Using Nanosensors and Bioorthogonal. ACS Nano. Apr. 26, 2011;5(4):3204-13.

(56) References Cited

OTHER PUBLICATIONS

Hofmann-Amtenbrink et al., Superparamagnetic nanoparticles for biomedical applications. Nanostructured Materials for Biomedical Applications. Jan. 2009:119-49.

Huang et al., Preparation of Silica-Encapsulated Hollow Gold Nanosphere Tags Using Layer-by-Layer Method for Multiplex Surface-Enhanced Raman Scattering Detection. Langmuir. Aug. 16, 2011;27(16):10228-10233.

Ivkov et al., Application of High Amplitude Alternating Magnetic Fields for Heat Induction of Nanoparticles Localized in Cancer. Clin Cancer Res. Oct. 1, 2005;11(19 Suppl):7093s-7103s.

Kaaki et al., Magnetic Nanocarriers of Doxorubicin Coated with Poly(ethylene glycol) and Folic Acid: Relation between Coating Structure, Surface Properties, Colloidal Stability, and Cancer Cell Targeting. Langmuir. Jan. 17, 2012;28(2):1496-1505.

Kim et al., Silver-Coated Dye-Embedded Silica Beads: A Core Material of Dual Tagging Sensors Based on Fluorescence and Raman Scattering. ACS Applied Materials & Interfaces. Feb. 23, 2011;3(2):324-330.

Kim et al., Silver-particle-based surface-enhanced resonance Raman scattering spectroscopy for biomolecular sensing and recognition. Anal Bioanal Chem. May 1, 2007;388(1):81-8.

Kircher et al., A Multimodal Nanoparticle for Preoperative Magnetic Resonance Imaging and Intraoperative Optical Brain Tumor Delineation. Cancer Research. Dec. 1, 2003;63(23):8122-8125.

Kircher et al., Molecular Body Imaging: MR Imaging, CT, and US. Part II. Applications, Radiology. Aug. 2012;264(2):349-368.

Kodali et al., Optimally designed nanolayered metal-dielectric particles as probes for massively multiplexed and ultrasensitive molecular assays. PNAS. Aug. 3, 2010;107(31):13620-5.

Kornhuber et al., Lipophilic Cationic Drugs Increase the Permeability of Lysosomal Membranes in a Cell Culture System. Journal of Cellular Physiology. Jul. 2010;224(1):152-164.

Kozissnik et al., Magnetic fluid hyperthermia: Advances, challenges, and opportunity. International Journal of Hyperthermia. Dec. 1, 2013;29(8):706-714.

Kumar et al., Magnetic nanomaterials for hyperthermia-based therapy and controlled drug delivery. Advanced Drug Delivery Reviews. Aug. 14, 2011;63(9):789-808.

Laurent et al., Magnetic fluid hyperthermia: Focus on superparamagnetic iron oxide nanoparticles. Advances in Colloid Interface Science. Aug. 10, 2011;166(1-2):8-23.

Lee et al., Exchange-coupled magnetic nanoparticles for efficient heat induction. Nature Nanotechnology. Jul. 2011;6(7):418-422.

Lee et al., Mesoporous silica nanoparticle pretargeting for PET imaging based on a rapid bioorthogonal reaction in a living body. Angew Chem Int Ed Engl. Sep. 27, 2013;52(40):10549-52. doi: 10.1002/anie.201304026. Epub Aug. 16, 2013.

Mannix et al., Nanomagnetic actuation of receptor-mediated signal transduction. Nature Nanotechnology. Jan. 2008;3(1):36-40.

Martin et al., Synthesis of bombesin-functionalized iron oxide nanoparticles and their specific uptake in prostate cancer cells. J. Nanopart. Res. Jun. 1, 2010;12(5):1599-1608.

Pestovskii et al., Investigation into the growth of gold nanoparticles immobilized on a mica surface due to tetrachloroauric acid reduction by hydorgen peroxide. Nanotechnologis in Russia. May 1, 2011; 6(3-4):189-195.

Popp et al., Raman meets Medicine—Raman spectroscopy: a powerful tool in Biophotonics. Proc. of the SPIE. Oct. 5, 2009;7503: 6 pages. doi: 10.1117/12.837623.

Sa et al, Development of Nanoaptamers Using a Mesoporous Silica Model Labeled with 99mTc for Cancer Taraetina. Oncoloay. 2012;82(4):213-217.

Schulze et al., Uptake and Biocompatibility of Functionalized Poly(vinylalcohol) Coated Superparamagnetic Maghemite Nanoparticles by Synoviocytes InVitro. Journal of Nanoscience and Nanotechnology. Sep. 1, 2006;6(9-10):2829-2840.

Sun et al, Self-Illuminating 64Cu-Doped CdSe/ZnS Nanocrystals in Vivo Tumor Imaging. Journal of the American Chemical Society. Feb. 5, 2014;136(5):1706-1709.

Therasse et al., New guidelines to evaluate the response to treatment in solid tumors. J. Natl. Cancer Inst. Feb. 2, 2000;92(3):205-216.

Tognalli et al., From Single to Multiple Ag-Layer Modification of Au Nanocavity Substrates: A Tunable Probe of the Chemical Surface-Enhanced Raman Scattering Mechanism. ACS Nano. Jul. 26, 2011;5(7):5433-5443.

Tomasini et al., Molecular dynamics simulations of rupture in lipid bilayers. Experimental Biology Medicine. Feb. 2010;235(2):181-188.

Tseng et al., Magnetic nanoparticle-mediated massively parallel mechanical modulation of single-cell behavior. Nature Methods. Nov. 2012;9(11):1113-19.

Vikman et al., Insulin secretion is highly sensitive to desorption of plasma membrane cholesterol. The FASEB Journal. Jan. 2009;23(1):58-67.

Wahajuddin et al., Superparamagnetic iron oxide nanoparticles: magnetic nanoplatforms as drug carriers. Int. J. of Nanomedicine. 2012;7:3445-71.

Wust et al., Hyperthermia in combined treatment of cancer. The Lancet Oncology. Aug. 1, 2002;3(8):487-497.

Xu et al., Differential Internalization of Superparamagnetic Iron Oxide Nanoparticles in Different Types of Cells. J. Nanoscience Nanotechnology. Nov. 1, 2010;10(11):7406-7410.

Zhang et al. Alternating Magnetic Fields Trigger Apoptosis by Destruction of Lysosomes with LAMP1-Targeted Nanoparticles. Biophysical Journal. Feb. 2, 2011;100(3):472.

Zhang et al., Dynamic magnetic fields remote-control apoptosis via nanoparticle rotation. ACS Nano. Apr. 22, 2014;8(4):3192-201.

* cited by examiner

RAMAN-TRIGGERED ABLATION/RESECTION SYSTEMS AND METHODS

CROSS REFERENCE TO RELATED APPLICATIONS

This application is a continuation-in-part application and claims priority to and the benefit of International Patent Application No. PCT/US2014/017508, filed Feb. 20, 2014, which claims the benefit of U.S. Provisional Application No. 61/767,241, filed Feb. 20, 2013, and of U.S. Provisional Application No. 61/834,854, filed Jun. 13, 2013. The contents of all of these applications are hereby incorporated by reference herein in their entireties.

GOVERNMENT SUPPORT

This invention was made with government support under grant numbers CA008748 and CA163961 awarded by the National Institutes of Health. The government has certain rights in the invention.

BACKGROUND

A variety of surgical techniques have been developed for the physical removal of cancerous or other diseased tissue. A goal of these methods is to remove cancerous/diseased tissue with minimal damage to nearby healthy tissue. A surgeon resects tissue that appears to be abnormal from visual inspection.

Surgical resection is the standard of care for most cancer types. However, complete resection is hindered by the ability of a surgeon to accurately identify tumor margins and small infiltrative tumor deposits. The degree of residual tumor post-surgery correlates with the probability of tumor recurrence and development of metastatic disease. To be certain that all tumor is removed, surgeons often perform "wide excisions" to achieve tumor-free margins. This may be problematic or impossible due to adjacent vital structures or organs which would need to be sacrificed. For example, limb amputation or exenteration, i.e., removal of adjacent organs, may be necessary. Alternatively, surgeons can spare adjacent structures, but risks for recurrence may be increased, due to tumor tissue remaining in the body.

Although advances in medical imaging systems, such as MRI, have been made to help a surgeon localize abnormal tissue prior to surgery, the surgeon's ability to identify abnormal tissue at the margins of infiltratively growing cancers or in the setting of metastatis spread via visual inspection during surgery are limited. Tissue may be analyzed during surgery to aid in determination of abnormal tissue boundaries, but biopsy and analysis of tissue by a pathologist during surgery is time-consuming, and may be limited to only one or two areas during a single operation.

There remains a need for imaging apparatus and methods that accurately detect and visually identify residual tumor during a real-time surgical procedure. This would allow more precise removal of cancerous and/or diseased tissue from locations within, surrounding, and/or adjacent to critical organs or tissue, where significant harm may result from damage to or removal of healthy tissue. This would also reduce the amount of healthy tissue that is removed, and would reduce the risk of recurrence.

SUMMARY

Systems and methods are presented herein that provide automated laser ablation and/or tissue resection triggered by detection of one or more Raman reporters, such as Raman nanoparticles (e.g., surface-enhanced Raman spectroscopic (SERS) and/or surface-enhanced (resonance) Raman spectroscopic (SERRS) nanoparticles), and/or intrinsic species that produce(s) a characteristic, identifiable Raman signal (e.g., Raman spectrum). These systems and methods provide for precise removal of cancerous or other diseased tissue with minimal damage to adjacent healthy tissue.

In one aspect, a method for operating a Raman-based resection system is disclosed. The method includes producing, via an ablation laser of the resection system, an interrogation electromagnetic radiation over a scanning point of a sample (e.g., patient) having been treated (e.g., injected) with a Raman reporter (e.g., SERS, SERRS, SERS-MRI, R-MR and other nanoparticles). The ablation laser illuminates the scanning point at an interrogating power level (e.g., less than 20 mW or 10% of the maximum power level of the ablation laser).

In some embodiments, the method includes acquiring, via a detector of the system, a signal indicative of scattered photons emanating from the scanning point following illumination by the interrogation electromagnetic radiation.

In some embodiments, the method includes determining, via a processor of the system, whether the acquired signal is indicative of the presence of the Raman reporter in and/or upon the scanning point. In some embodiments, the processor determines whether the acquired signal is indicative of the presence of the Raman reporter in and/or upon the scanning point by determining a comparison index between the acquired signal and a referenced signal of the Raman reporter and evaluating the determined comparison index to determine if the index exceeds a pre-defined threshold (e.g., between 0.5 and 1). The comparison index may be calculated based on:

$$\frac{\sum_{i=1}^{n}(s_i-s)(r_i-r)}{\sqrt{\sum_{i=1}^{n}(s_i-s)^2 \sum_{i=1}^{n}(r_i-r)^2}},$$

in which $s_i$ is the acquired spectrum at acquisition point i, $r_i$ is the reference spectrum at point i, s is the mean of the acquired spectrum, and r is the mean of the reference spectrum, and n is the number acquisition points.

In other embodiments, the processor determines whether the acquired signal is indicative of the presence of the Raman reporter in and/or upon the scanning point using a method selected from the group consisting of absolute different value search, first derivative absolute value search, least square search, first derivative least square search, Euclidean distance search, correlation coefficient, and correlation search.

In some embodiments, the method includes, producing, via the ablation laser, an ablation electromagnetic radiation over the scanning point to ablate tissue at the scanning point responsive to a determination of the presence of the Raman reporter in and/or upon the scanning point. The ablation electromagnetic radiation is at a power level sufficient to ablate tissue (e.g., power level greater than 200 mW or 75% of the maximum power level of the ablation laser). In some embodiments, the spectrum of Raman scattered photons is acquired in about or less than 120 milliseconds.

In some embodiments, the outputs of the first and second excitation electromagnetic radiation are intermittent in between each measurement and ablation sequence at a given location and in between each sequence among the different locations. The method may include de-energizing the ablation laser when determining, via the processor of the system, whether the acquired spectrum is indicative of the presence of the Raman reporter. In other embodiments, the outputs of the first and second excitation electromagnetic radiation are continuous between the measurement and the ablation for a given spot location and between these sequences performed at the different locations.

In another aspect of the disclosure, a system for detecting and ablating a sample treated with a Raman reporter is described. The system includes an ablation laser (e.g., diode-pumped solid-state laser or an ion gas laser) (such as a $CO_2$ laser, Er:YAG laser, or Nd:YAG laser) for directing electromagnetic radiation onto or into a scanning point of a target tissue. The system includes an instrument operably linked to the ablation laser, including optics for directing the electromagnetic radiation onto or into the scanning point of the target tissue.

In some embodiments, the system includes a detector for detecting scattered photons emanating from the scanning point of the target tissue. The scattered photons results from illumination of the sample (with or without the Raman reporter) with the electromagnetic radiation. The electromagnetic radiation may have a wavelength that is in the visible range, the near-infrared range, or in the mid-infrared range (e.g., about 500 nm to about 11 μm). In some embodiments, the electromagnetic radiation has a wavelength of about 785 nm.

In some embodiments, the system includes a processor configured to regulate output power levels of the ablation laser and to process data corresponding to the scattered photons detected from the scanning point of the target tissue. The processor is configured to trigger a switch from an interrogation power level (e.g., less than 10% of the maximum power level of the ablation laser or less than 10 milliwatts) to an ablation power level (e.g., greater than 50% of the maximum power level or greater than 150 milliwatts) of the ablation laser upon a determination of a presence of a Raman reporter (e.g., SERS, SERRS, SERS-MRI, R-MR and other nanoparticles) in the target tissue in or near the scanning point. The ablation power level is sufficient to ablate tissue at the scanning point. In some embodiments, the processor determines whether the acquired signal is indicative of the presence of the Raman reporter in and/or upon the scanning point by (i) determining a comparison index between the acquired signal and a referenced signal of the Raman reporter and (ii) evaluating the determined comparison index to determine if the index exceeds a pre-defined threshold (e.g., between 0.5 and 1.0).

In some embodiments, the instrument includes optics for imaging. In some embodiments, the system includes a suction vacuum operably linked to the instrument. In some embodiments, the system includes a raster scanning device for positioning the instrument over the target tissue.

In another aspect, a system is provided herein with a resection/ablation mechanism that is activated only at locations at which one or more Raman reporters are detected. For example, an ablation laser or resection mechanism is activated at a location only when a Raman signal indicative of the presence of a Raman reporter at the location is recognized by a Raman spectrometer, where the Raman reporter is associated with tissue to be resected/ablated (e.g., cancerous, diseased, infected, or otherwise abnormal tissue).

If the specific Raman signal associated with one or more Raman reporters is not detected, the ablation/resection mechanism is not activated. In this way, extremely precise destruction and/or removal of diseased tissue may be accomplished while limiting damage to nearby healthy tissue. For example, a precision of 500, 400, 300, 200, 100, or 50 micrometers or better may be achieved.

In certain embodiments, a Raman reporter is a Raman nanoparticle (e.g., SERS and/or SERRS nanoparticle), or a component of a Raman nanoparticle. In some embodiments, Raman nanoparticles are administered (e.g., by injection or topically) to a patient/subject and are allowed to accumulate in and/or around cancerous tissue, pre-cancerous tissue, or other diseased tissue (e.g., necrotic tissue, infected tissue, inflamed tissue, etc.). The Raman nanoparticles that may be used in the disclosed systems and methods include, for example, those described in Kircher et al., Nature Medicine 2012 Apr. 15; 18(5): 829-34, the text of which is incorporated herein by reference in its entirety. These are based on surface enhanced Raman scattering (SERS). Other nanoparticles may be used, as long as they create a sufficiently detectable and distinguishable Raman signal (e.g., a Raman spectrum).

In some embodiments, a Raman reporter is a molecule or substance present within, on, or near diseased tissue itself ("intrinsic species"), which is identified or targeted using an intrinsic Raman spectrum (e.g., a Raman spectrum detected following illumination of tissue). In some embodiments, tissue is selected and/or resected/ablated if a detected Raman signal satisfactorily matches a predetermined Raman signal known to be indicative of the Raman reporter.

In certain embodiments, the system includes a hand-held instrument of size and shape that may be customized depending on the application. For example, the system may include a laser suitable to ablate/destroy tissue (such as, for example, a $CO_2$, Er:YAG, or Nd:YAG laser). Alternatively or additionally, the system may include a motor-driven, controlled resection mechanism such as, for example, a small rotating blade, located at the tip of the hand-held instrument. Alternatively or additionally, the system may include an electro-cautery mechanism, a cryoablation mechanism, and/or a radiofrequency ablation mechanism. In some embodiments, an ablation mechanism is a robotic/remote controlled ablation mechanism (e.g., located at the tip of the hand-held instrument). The system may also include a vacuum suction mechanism connected to a collection bag for removal of destroyed/ablated/resected tissue as well as nanoparticles located within the target tissue. The system may also include an excitation laser and associated optics for determination of Raman spectra associated with detected photons emanating from the tissue. A rinsing mechanism may be included to keep optics clean during the procedure. The hand-held instrument may be connected to other components of the system via fiberoptic cable, for example, and suction tubing. The hand-held instrument may be connected to components of a box housing mechanics, optics, electronics, excitation laser, ablation laser, resection instrument motor, radiofrequency or cryoablation generator, suction motor, rinsing mechanism, Raman spectral analysis optics, and/or the CCD chip.

A surgeon using the disclosed system can destroy or remove cancerous (or otherwise abnormal) tissue quickly and with high precision in a semiautomated fashion. For example, the hand-held instrument may be positioned and moved over regions of tissue "blindly" or "semi-blindly" near the site of disease/cancer, as the system destroys only cancerous tissue, with no or minimal damage to adjacent healthy tissue. The system may be used, for example, during open surgical procedures, in-office (non-surgical) procedures, invasive procedures, non-invasive or minimally invasive procedures, endoscopic procedures, robotically-assisted procedures, or in external applications such as skin cancer removal.

An automated or semi-automated X-Y (two-dimensional) or X-Y-Z (three-dimensional) scan of the tissue by the instrument may be performed. For example, the detection+ablation/resection instrument may be positioned such that excitation light from the instrument is directed to a sequence of X-Y or X-Y-Z positions of the tissue. At each location, light is detected and the processor of the system determines whether a Raman reporter is detected at that location. If so, the resection/ablation mechanism is activated at that location such that only tissue at that location is removed or destroyed. The resection/ablation mechanism is then deactivated prior to moving the instrument to a second location, whereupon excitation light is directed to the second position and light is detected from the second position and the resection/ablation mechanism is activated only if a Raman reporter is detected at that second position, and so on.

For applications involving skin cancer removal, or other abnormal topical tissue removal, a Raman reporter is a SERS nanoparticle (or a component thereof) that may be applied topically or injected prior to operation of the handheld instrument. A topical application may include penetrating peptides to facilitate absorption of the SERS nanoparticles into the skin. In some embodiments, a Raman reporter is an intrinsic species within, on, or near the skin cancer or other abnormal tissue.

In one aspect, the invention encompasses a system comprising: an excitation light source for directing excitation light onto or into a target tissue; an instrument (e.g., handheld instrument) operably linked to the excitation light source, the instrument comprising: optics for directing the excitation light onto or into the target tissue; a detector for detecting Raman scattered photons emanating from the target tissue, said Raman scattered photons resulting from illumination with the excitation light; a resector/ablator mechanism; a processor (e.g., a Raman spectrometer and associated computer processor and/or software) configured to process data corresponding to the Raman scattered photons detected from the target tissue; and a resector/ablator controller operably linked to the processor and operably linked to the resector/ablator mechanism.

In certain embodiments, the excitation light source is a laser. In certain embodiments, the excitation light has a wavelength of about 500 nm to about 10 μm. In some embodiments, the excitation light has a wavelength of about 785 nm. In certain embodiments, the excitation light is near-infrared light (e.g., where deeper penetration, e.g., up to about 1 cm, is desired). In certain embodiments, the excitation is ultraviolet light (e.g., where shallow penetration, e.g., only up to 1 mm, up to 2 mm, or up to 3 mm, is desired). In certain embodiments, the instrument is an endoscopic instrument.

In certain embodiments, the resector/ablator mechanism comprises a laser. In certain embodiments, the laser of the resector/ablator mechanism is a $CO_2$ laser. In certain embodiments, the resector/ablator mechanism is a mechanical resector (e.g., rotary blade, vibrating knife, or percussing knife). In some embodiments, the resector/ablator mechanism is an electro-cautery mechanism, a cryoablation mechanism, and/or a radiofrequency ablation mechanism. In certain embodiments, the resector/ablator controller is configured to activate the resector/ablator mechanism to resect, ablate, and/or destroy tissue at a given location only if Raman scattered photons detected from the given location (e.g., a detected Raman signal or spectrum) indicate the presence of a Raman reporter (e.g., SERS nanoparticles, SERRS nanoparticles, or an intrinsic species). In certain embodiments, the system further comprises a suction vacuum operably linked to the instrument.

In another aspect, the invention encompasses a method of resecting, ablating, and/or destroying diseased tissue, the method comprising the steps of: positioning an instrument in relation to a first location (e.g., (x,y,z) or (x,y) location) of a target tissue of a subject (e.g., human or animal), the instrument comprising: optics for directing excitation light onto or into the target tissue at a given location; a detector for detecting Raman scattered photons emanating from the target tissue at the given location; and a resector/ablator mechanism; detecting the Raman scattered photons emanating from the first location of the target tissue; analyzing the detected Raman scattered photons emanating from the first location to determine whether the detected photons are indicative of the presence of a Raman reporter (e.g., SERS nanoparticles, SERRS nanoparticles, or intrinsic species) at the first location; and activating the resector/ablator mechanism (e.g., via a resector/ablator controller) to resect the target tissue at the first location only if the analyzed photons from the first location are determined to be indicative of the presence of a Raman reporter at the first location.

In certain embodiments, the method further comprises: deactivating the resector/ablator mechanism prior to repositioning of the instrument in relation to a second location of the target tissue (e.g., wherein the second location of the target tissue is adjacent to the first location); detecting the Raman scattered photons emanating from the second location of the target tissue; analyzing the detected Raman scattered photons emanating from the second location to determine whether the detected photons are indicative of the presence of a Raman reporter (e.g., SERS nanoparticles, SERRS nanoparticles, and/or intrinsic species) at the second location; and activating the resector/ablator mechanism to resect, ablate, and/or destroy the target tissue at the second location only if the analyzed photons from the second location are determined to be indicative of the presence of the Raman reporter at the second location.

In certain embodiments, the method further comprises administering nanoparticles (e.g., SERS nanoparticles or SERRS nanoparticles) to the subject prior to implementation of the instrument (e.g., allowing accumulation of the nanoparticles in regions associated with disease). In certain embodiments, the method further comprises scanning the subject prior to implementation of the instrument to confirm the absence of nanoparticles from healthy (e.g., normal, e.g., non-cancerous) tissue.

In certain embodiments, the instrument is operably linked to an excitation light source. In certain embodiments, the excitation light source is a laser. In certain embodiments, the excitation light has a wavelength of about of about 500 nm to about 11 m. In some embodiments, the excitation light has a wavelength of about 785 nm. In certain embodiments, the excitation light is near-infrared light (e.g., where deeper penetration, e.g., up to about 1 cm, is desired). In certain embodiments, the excitation is ultraviolet light (e.g., where shallow penetration, e.g., only up to 1 mm, up to 2 mm, or up to 3 mm, is desired). In certain embodiments, the instrument is an endoscopic device. In certain embodiments, the resector/ablator mechanism comprises a laser. In certain embodiments, the laser of the resector/ablator mechanism is a $CO_2$ laser. In certain embodiments, the resector/ablator mechanism is a mechanical resector (e.g., rotary blade, vibrating knife, or percussing knife). In some embodiments, the resector/ablator mechanism is an electro-cautery mechanism, a cryoablation mechanism, and/or a radiofrequency ablation mechanism.

In certain embodiments, the analyzing step comprises using a computer processor (e.g., a Raman spectrometer and associated computer processor and/or software) to process data corresponding to the detected Raman scattered photons. In certain embodiments, the method further comprises removing resected tissue. In certain embodiments, the method is an in vivo method.

In any of the aspects described herein, the instrument can be a handheld instrument, a stationary instrument, and/or a robotically assisted instrument. In some embodiments, the device is an endoscopic instrument.

In any of the aspects described herein, the system may further include other optics, hardware, electronics, and/or software for imaging target cells or tissues.

In some aspects, apparatus and methods are presented herein that permit real-time, accurate detection of residual tumor in the operating room. The Raman-based wide-field imaging apparatus and methods described herein permit real-time imaging of tumor-targeted nanoparticles in an operating bed—for example, across a 30×30 cm field of view. The wide field imaging apparatus is particularly useful for imaging Raman signals emitted by nanoparticles such as R-MR nanoparticles, as described in Nature Medicine, Vol. 18, pp. 829,834, 2012, incorporated herein by reference in its entirety.

Existing Raman scanners are pen-like point scanners which do not acquire images, or imaging microscopes built for use of in vitro samples or small animals. By contrast, described herein is a wide field Raman scanner that is able to image an entire operative bed in near real-time.

In one aspect, the invention relates to a wide field Raman imaging apparatus comprising: at least one light source for producing excitation light; optics for directing the excitation light onto and/or into a target tissue; a detector for detecting Raman scattered photons emanating from the target tissue following illumination by the excitation light, the Raman scattered photons indicative of the presence of a Raman reporter in and/or upon the target tissue; and a processor configured to process data corresponding to the Raman scattered photons detected from the target tissue and to produce an image depicting a wide field corresponding to the target tissue, the image visually indicating position and/or intensity of the Raman reporter within the wide field.

In some embodiments, the at least one light source, the detector, and the processor are configured to produce a substantially real-time series of images visually indicating position and/or intensity of the Raman reporter within the wide field. In some embodiments, the processor is configured to produce each image of the real-time series of images by obtaining one or more monochromatic images within a given short interval of time (e.g., 500 milliseconds or less, e.g., 50 milliseconds or less), each monochromatic image obtained at a wavelength corresponding to a spectral peak characteristic of the Raman reporter, and to use the one or more monochromatic images to produce the image in the real-time series indicating the position and/or intensity of the Raman reporter within the wide field during the given short interval of time.

In some embodiments, the wide field is at least 100 cm$^2$ in area (e.g., at least 300, 500, 1000, or 1200 cm$^2$). In some embodiments, the at least one light source comprises a tunable laser source. In some embodiments, the optics comprise a tunable laser line filter (LLF) and/or a tunable notch filter (NF) (e.g., said filter(s) comprising tandem thick volume Bragg gratings). In some embodiments, the detector is a hyperspectral imager with a spatial resolution no greater than about 10 mm$^2$ (e.g., from 0.1 mm$^2$ to 3 mm$^2$, e.g., about 1 mm$^2$). In some embodiments, the detector comprises an optical pathway configured to allow x-y imaging of the Raman reporter within the wide field regardless of depth (z) of the Raman reporter in relation to the detector.

In some embodiments, the apparatus further includes a visual display for viewing the image. In some embodiments, the processor is configured to produce a substantially real-time series of images and transmit the images for display on a personal image display (e.g., worn by the surgeon), such that the series of images can be displayed on, in, or through a transparent display that superimposes the displayed series of images over a corresponding view of the wide field. In some embodiments, the processor is configured to track the position of the personal image display and compensate the series of images for movement of the display (e.g., movement of the wearer of the display), accordingly (e.g., by tracking the location of markers affixed on or near the patient as they appear within a field of view of the personal image display).

In some embodiments, the apparatus further comprises a visual display, wherein the visual display is an adjustable tablet-shaped screen positionable in relation to the target tissue of a patient in an operating bed, wherein the optics for directing the excitation light onto and/or into the target tissue are positioned on the side of the tablet-shaped screen facing the operating bed, and the image is displayed on the side of the tablet-shaped screen facing away from the operating bed so as to be viewable by a surgeon.

In some embodiments, the light source for producing excitation light comprises one or more lasers, and wherein the optics for directing the excitation light onto and/or into the target tissue are configured to disperse the excitation light evenly over the wide field corresponding to the target tissue.

In some embodiments, the apparatus further includes a resection/ablation mechanism described herein, e.g., a resection/ablation mechanism that is activated only at locations at which one or more Raman reporters are detected.

In another aspect, the invention relates to a method for performing wide field Raman imaging of target tissue of a patient during a surgical procedure, the method comprising: administering a first Raman reporter to the patient (e.g., intravenously, topically, intraarterially, intratumorally, intranodally, via lymphatic vessels, etc.); illuminating the target tissue with excitation light; detecting Raman scattered photons emanating from the target tissue following illumination by the excitation light, the Raman scattered photons indicative of the presence of the first Raman reporter in and/or upon the target tissue; obtaining, by the processor of a computing device, an image depicting a wide field corresponding to the target tissue, the image visually indicating position and/or intensity of the first Raman reporter within the wide field; and displaying the image.

In some embodiments, the first Raman reporter accumulates within and/or upon cancerous, diseased, and/or otherwise abnormal portions of the target tissue prior to the illuminating and detecting step. In some embodiments, the method comprises obtaining, by the processor of the computing device, a substantially real-time series of images visually indicating position and/or intensity of the first Raman reporter within the wide field and displaying the series of images in real-time. In some embodiments, the method comprises obtaining, for each image of the real-time series of images, by the processor of the computing device, one or more monochromatic images within a given short interval of time (e.g., 500 milliseconds or less, e.g., 50 milliseconds or less), each monochromatic image obtained at a wavelength corresponding to a spectral peak characteristic of the Raman reporter, and using the one or more monochromatic images to produce the image in the real-time series indicating the position and/or intensity of the Raman reporter within the wide field during the given short interval of time. In some embodiments, the method comprises displaying the real-time series of images at a frame rate at least 10 frames per second (e.g., 20 to 25 frames per second).

In some embodiments, the first Raman reporter comprises Raman-MRI (R-MR) nanoparticles. In some embodiments, the first Raman reporter comprises SERRS nanoparticles.

In some embodiments, the method comprises administering a second Raman reporter to the patient with different Raman signature than the first Raman reporter, wherein the detected Raman scattered photons are indicative of the presence of the first Raman reporter and the second Raman reporter in and/or upon the target tissue, and wherein the image visually indicates position and/or intensity of the first Raman reporter and the second Raman reporter within the wide field in a manner such that the first Raman reporter is distinguishable from the second Raman reporter.

In some embodiments, the wide field is at least 100 cm2 in area (e.g., at least 300, 500, 1000, or 1200 cm2). In some embodiments, the method comprises displaying the image on a visual display, wherein the visual display is an adjustable tablet-shaped screen positionable in relation to the target tissue of a patient in an operating bed, wherein the image is displayed on the side of the tablet-shaped screen facing away from the operating bed such that it is viewable by a surgeon during a surgical procedure.

In some embodiments, the method comprises producing, by the processor of the computing device, a substantially real-time series of images and displaying the images on a personal image display (e.g., worn by a surgeon operating on the patient), such that the series of images are displayed on, in, or through a transparent display that superimposes the displayed series of images over a corresponding view of the wide field. In some embodiments, the method comprises tracking, by the processor of the computing device, the position of the personal image display, and compensating the series of images for movement of the display (e.g., movement of the wearer of the display), accordingly (e.g., by tracking the location of markers affixed on or near the patient as they appear within the field of view of the personal image display). Details regarding an exemplary personal image display are described in U.S. Patent Application Publication No. US 2013/0044042, published Feb. 21, 2013.

In some embodiments, the method further includes resecting, ablating, and/or destroying diseased tissue using a resection/ablation apparatus, system, and/or method described herein.

In some aspects, systems and methods are presented herein that provide automated laser ablation and/or tissue resection triggered by detection of one or more Raman reporters, such as Raman nanoparticles (e.g., surface-enhanced Raman spectroscopic (SERS) and/or surface-enhanced (resonance) Raman spectroscopic (SERRS) nanoparticles), and/or intrinsic species that produce(s) a characteristic, identifiable Raman signal (e.g., Raman spectrum). These systems and methods provide for precise removal of cancerous or other diseased tissue with minimal damage to adjacent healthy tissue.

In some embodiments, a system is provided herein with a resection/ablation mechanism that is activated only at locations at which one or more Raman reporters are detected. For example, an ablation laser or resection mechanism is activated at a location only when a Raman signal indicative of the presence of a Raman reporter at the location is recognized by a Raman spectrometer, where the Raman reporter is associated with tissue to be resected/ablated (e.g., cancerous, diseased, infected, or otherwise abnormal tissue). If the specific Raman signal associated with one or more Raman reporters is not detected, the ablation/resection mechanism is not activated. In this way, extremely precise destruction and/or removal of diseased tissue may be accomplished while limiting damage to nearby healthy tissue. For example, a precision of 500, 400, 300, 200, 100, or 50 micrometers or better may be achieved.

In certain embodiments, a Raman reporter is a Raman nanoparticle (e.g., SERS and/or SERRS nanoparticle), or a component of a Raman nanoparticle. In some embodiments, Raman nanoparticles are administered (e.g., by injection or topically) to a patient/subject and are allowed to accumulate in and/or around cancerous tissue, pre-cancerous tissue, or other diseased tissue (e.g., necrotic tissue, infected tissue, inflamed tissue, etc.). The Raman nanoparticles that may be used in the disclosed systems and methods include, for example, those described in Kircher et al., Nature Medicine 2012 Apr. 15; 18(5): 829-34, the text of which is incorporated herein by reference in its entirety. These are based on surface enhanced Raman scattering (SERS). Other nanoparticles may be used, as long as they create a sufficiently detectable and distinguishable Raman signal (e.g., a Raman spectrum).

In some embodiments, a Raman reporter is a molecule or substance present within, on, or near diseased tissue itself ("intrinsic species"), which is identified or targeted using an intrinsic Raman spectrum (e.g., a Raman spectrum detected following illumination of tissue). In some embodiments, tissue is selected and/or resected/ablated if a detected Raman signal satisfactorily matches a predetermined Raman signal known to be indicative of the Raman reporter.

In certain embodiments, the system includes a hand-held instrument of size and shape that may be customized depending on the application. For example, the system may include a laser suitable to ablate/destroy tissue (such as, for example, a $CO_2$, Er:YAG, or Nd:YAG laser). Alternatively or additionally, the system may include a motor-driven, controlled resection mechanism such as, for example, a small rotating blade, located at the tip of the hand-held instrument. Alternatively or additionally, the system may include an electro-cautery mechanism, a cryoablation mechanism, and/or a radiofrequency ablation mechanism. In some embodiments, an ablation mechanism is a robotic/remote controlled ablation mechanism (e.g., located at the tip of the hand-held instrument). The system may also include a vacuum suction mechanism connected to a collection bag for removal of destroyed/ablated/resected tissue as well as nanoparticles located within the target tissue. The system may also include an excitation laser and associated optics for determination of Raman spectra associated with detected photons emanating from the tissue. A rinsing mechanism may be included to keep optics clean during the procedure. The hand-held instrument may be connected to other components of the system via fiberoptic cable, for example, and suction tubing. The hand-held instrument may be connected to components of a box housing mechanics, optics, electronics, excitation laser, ablation laser, resection instrument motor, radiofrequency or cryoablation generator, suction motor, rinsing mechanism, Raman spectral analysis optics, and/or the CCD chip.

A surgeon using the disclosed system can destroy or remove cancerous (or otherwise abnormal) tissue quickly and with high precision in a semiautomated fashion. For example, the hand-held instrument may be positioned and moved over regions of tissue "blindly" or "semi-blindly" near the site of disease/cancer, as the system destroys only cancerous tissue, with no or minimal damage to adjacent healthy tissue. The system may be used, for example, during open surgical procedures, in-office (non-surgical) procedures, invasive procedures, non-invasive or minimally invasive procedures, endoscopic procedures, robotically-assisted procedures, or in external applications such as skin cancer removal.

An automated or semi-automated X-Y (two-dimensional) or X-Y-Z (three-dimensional) scan of the tissue by the instrument may be performed. For example, the detection+ablation/resection instrument may be positioned such that excitation light from the instrument is directed to a sequence of X-Y or X-Y-Z positions of the tissue. At each location, light is detected and the processor of the system determines whether a Raman reporter is detected at that location. If so, the resection/ablation mechanism is activated at that location such that only tissue at that location is removed or destroyed. The resection/ablation mechanism is then deactivated prior to moving the instrument to a second location, whereupon excitation light is directed to the second position and light is detected from the second position and the resection/ablation mechanism is activated only if a Raman reporter is detected at that second position, and so on.

For applications involving skin cancer removal, or other abnormal topical tissue removal, a Raman reporter is a SERS nanoparticle (or a component thereof) that may be applied topically or injected prior to operation of the handheld instrument. A topical application may include penetrating peptides to facilitate absorption of the SERS nanoparticles into the skin. In some embodiments, a Raman reporter is an intrinsic species within, on, or near the skin cancer or other abnormal tissue.

In one aspect, the invention encompasses a system comprising: an excitation light source for directing excitation light onto or into a target tissue; an instrument (e.g., hand-held instrument) operably linked to the excitation light source, the instrument comprising: optics for directing the excitation light onto or into the target tissue; a detector for detecting Raman scattered photons emanating from the target tissue, said Raman scattered photons resulting from illumination with the excitation light; a resector/ablator mechanism; a processor (e.g., a Raman spectrometer and associated computer processor and/or software) configured to process data corresponding to the Raman scattered photons detected from the target tissue; and a resector/ablator controller operably linked to the processor and operably linked to the resector/ablator mechanism.

In certain embodiments, the excitation light source is a laser. In certain embodiments, the excitation light has a wavelength of about 500 nm to about 11 µm. In some embodiments, the excitation light has a wavelength of about 785 nm. In certain embodiments, the excitation light is near-infrared light (e.g., where deeper penetration, e.g., up to about 1 cm, is desired). In certain embodiments, the excitation is ultraviolet light (e.g., where shallow penetration, e.g., only up to 1 mm, up to 2 mm, or up to 3 mm, is desired). In certain embodiments, the instrument is an endoscopic instrument.

In certain embodiments, the resector/ablator mechanism comprises a laser. In certain embodiments, the laser of the resector/ablator mechanism is a diode-pumped solid-state laser or an ion gas laser (such as a $CO_2$ laser). In certain embodiments, the resector/ablator mechanism is a mechanical resector (e.g., rotary blade, vibrating knife, or percussing knife). In some embodiments, the resector/ablator mechanism is an electro-cautery mechanism, a cryoablation mechanism, and/or a radiofrequency ablation mechanism. In certain embodiments, the resector/ablator controller is configured to activate the resector/ablator mechanism to resect, ablate, and/or destroy tissue at a given location only if Raman scattered photons detected from the given location (e.g., a detected Raman signal or spectrum) indicate the presence of a Raman reporter (e.g., SERS nanoparticles, SERRS nanoparticles, or an intrinsic species). In certain embodiments, the system further comprises a suction vacuum operably linked to the instrument.

In another aspect, the invention encompasses a method of resecting, ablating, and/or destroying diseased tissue, the method comprising the steps of: positioning an instrument in relation to a first location (e.g., (x,y,z) or (x,y) location) of a target tissue of a subject (e.g., human or animal), the instrument comprising: optics for directing excitation light onto or into the target tissue at a given location; a detector for detecting Raman scattered photons emanating from the target tissue at the given location; and a resector/ablator mechanism; detecting the Raman scattered photons emanating from the first location of the target tissue; analyzing the detected Raman scattered photons emanating from the first location to determine whether the detected photons are indicative of the presence of a Raman reporter (e.g., SERS nanoparticles, SERRS nanoparticles, or intrinsic species) at the first location; and activating the resector/ablator mechanism (e.g., via a resector/ablator controller) to resect the target tissue at the first location only if the analyzed photons from the first location are determined to be indicative of the presence of a Raman reporter at the first location.

In certain embodiments, the method further comprises: deactivating the resector/ablator mechanism prior to repositioning of the instrument in relation to a second location of the target tissue (e.g., wherein the second location of the target tissue is adjacent to the first location); detecting the Raman scattered photons emanating from the second location of the target tissue; analyzing the detected Raman scattered photons emanating from the second location to determine whether the detected photons are indicative of the presence of a Raman reporter (e.g., SERS nanoparticles, SERRS nanoparticles, and/or intrinsic species) at the second location; and activating the resector/ablator mechanism to resect, ablate, and/or destroy the target tissue at the second location only if the analyzed photons from the second location are determined to be indicative of the presence of the Raman reporter at the second location.

In certain embodiments, the method further comprises administering nanoparticles (e.g., SERS nanoparticles or SERRS nanoparticles) to the subject prior to implementation of the instrument (e.g., allowing accumulation of the nanoparticles in regions associated with disease). In certain embodiments, the method further comprises scanning the subject prior to implementation of the instrument to confirm the absence of nanoparticles from healthy (e.g., normal, e.g., non-cancerous) tissue.

In certain embodiments, the instrument is operably linked to an excitation light source. In certain embodiments, the excitation light source is a laser. In certain embodiments, the excitation light has a wavelength of about of about 500 nm to about 11 µm. In some embodiments, the excitation light has a wavelength of about 785 nm. In certain embodiments, the excitation light is near-infrared light (e.g., where deeper penetration, e.g., up to about 1 cm, is desired). In certain embodiments, the excitation is ultraviolet light (e.g., where shallow penetration, e.g., only up to 1 mm, up to 2 mm, or up to 3 mm, is desired). In certain embodiments, the instrument is an endoscopic device. In certain embodiments, the resector/ablator mechanism comprises a laser. In certain embodiments, the laser of the resector/ablator mechanism is a diode-pumped solid-state laser or an ion gas laser (such as a $CO_2$ laser). In certain embodiments, the resector/ablator mechanism is a mechanical resector (e.g., rotary blade, vibrating knife, or percussing knife). In some embodiments, the resector/ablator mechanism is an electro-cautery mechanism, a cryoablation mechanism, and/or a radiofrequency ablation mechanism.

In certain embodiments, the analyzing step comprises using a computer processor (e.g., a Raman spectrometer and associated computer processor and/or software) to process data corresponding to the detected Raman scattered photons. In certain embodiments, the method further comprises removing resected tissue. In certain embodiments, the method is an in vivo method.

In any of the aspects described herein, the instrument can be a handheld instrument, a stationary instrument, and/or a robotically assisted instrument. In some embodiments, the device is an endoscopic instrument.

In any of the aspects described herein, the system may further include other optics, hardware, electronics, and/or software for imaging target cells or tissues.

BRIEF DESCRIPTION OF THE DRAWINGS

The following figures are presented for the purpose of illustration only, and are not intended to be limiting.

Immunohistochemical correlation shows that small foci of Raman signal correspond to residual microscopic prostate cancer that could not have been visualized otherwise and would have been "missed". Note the excellent correlation between the histological tumor markers and the presence of the nanoparticles ("Raman nanoparticle staining"=antibody against PEGylated silica nanoparticle surface).

Figure 12:
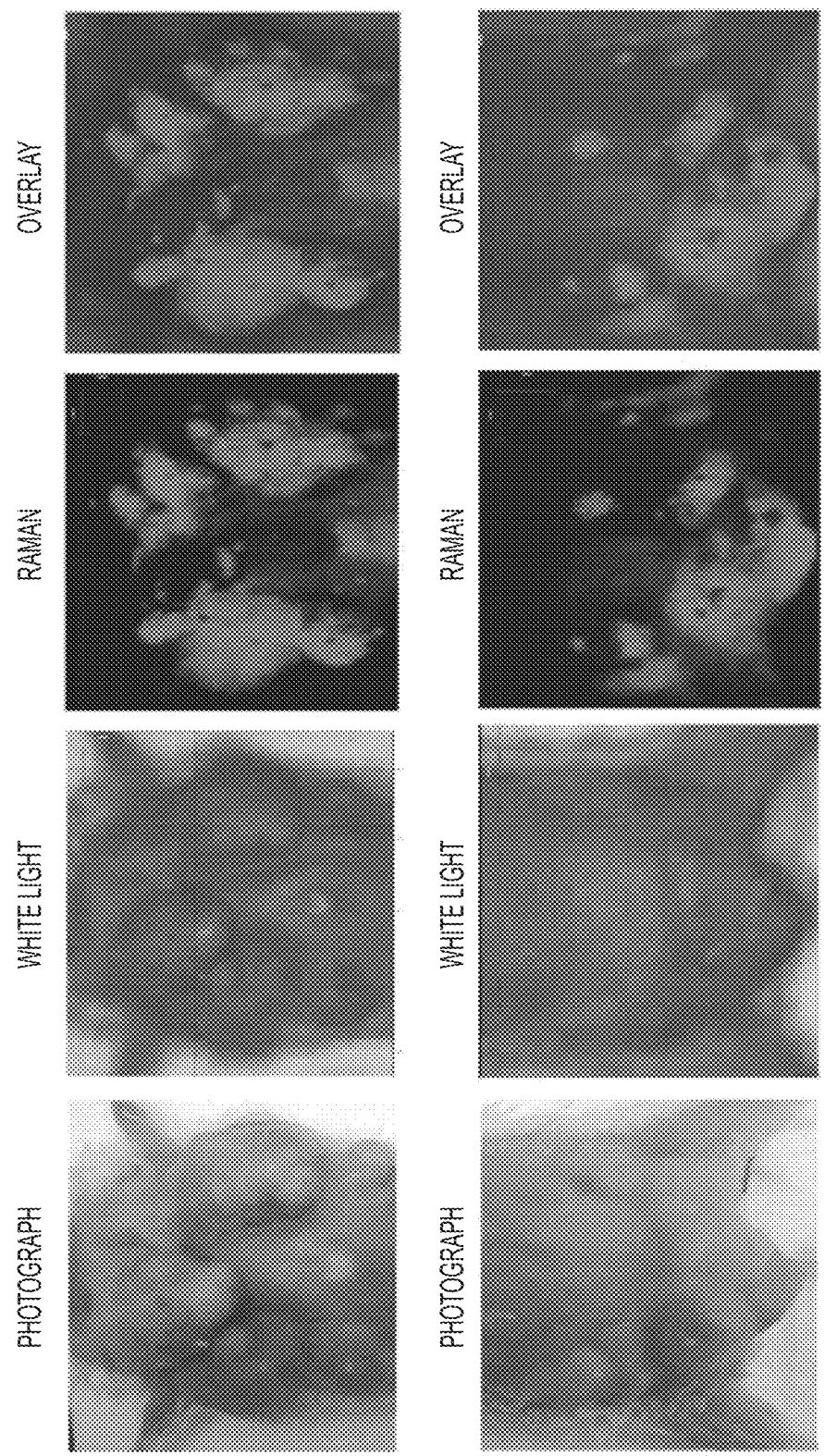

FIG. 12 shows how R-MR nanoparticles can be used to detect breast cancer in a state-of-the-art genetic MMTV-PyMT breast cancer mouse model, according to an illustrative embodiment. Mice with this genetic mutation spontaneously develop multiple breast cancers in different mammary glands and closely mimic human breast cancer pathology. Note that the Raman signal from the R-MR-Nanoparticles accurately depicts the extent of multiple 3-6 mm sized breast cancers in the same mice, including small submillimeter tumor extensions. Upper row: Breast cancers developed along the upper and middle mammary glands of a MMTV-PyMT mouse. Lower row: Breast cancers developed within the lower mammary glands of a MMTV-PyMT mouse.

Figure 13:
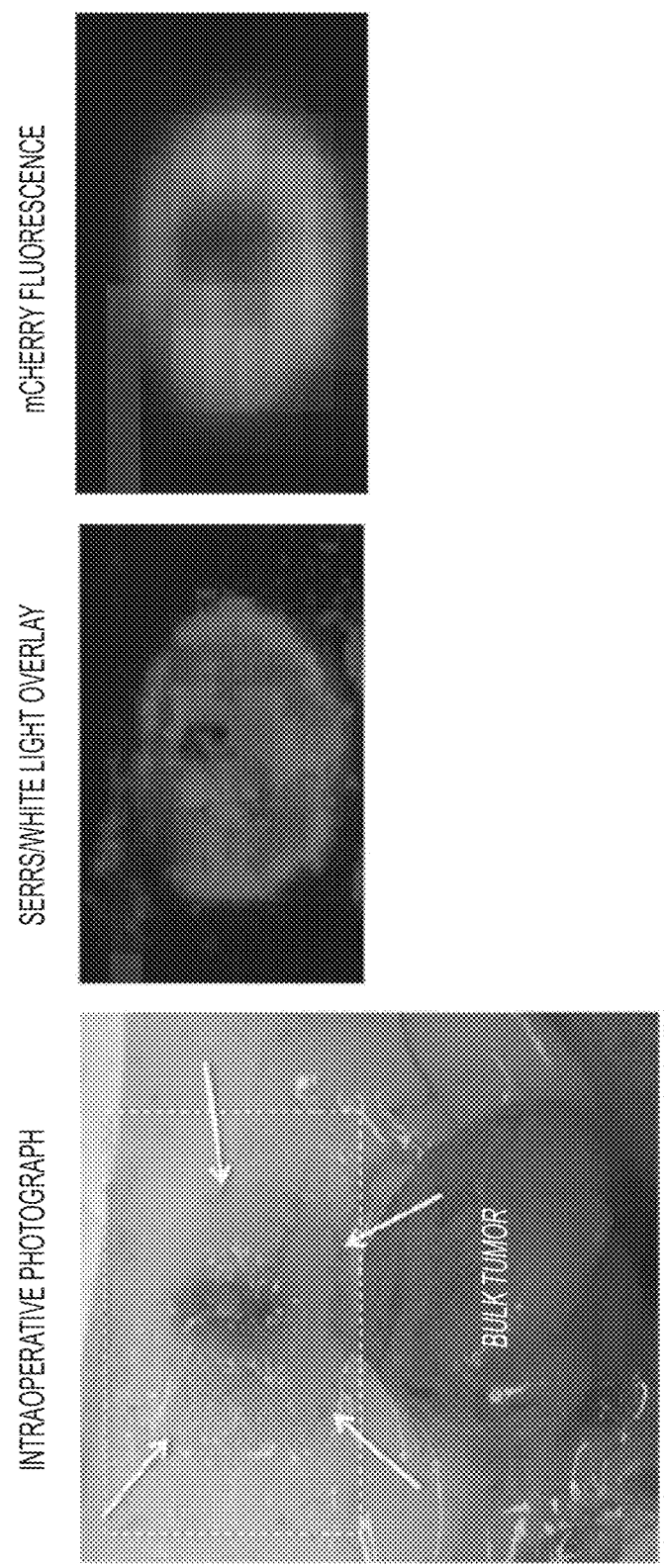

FIG. 13 shows how R-MR nanoparticles can be used to detect microscopic tumor infiltration into the skin, according to an illustrative embodiment. This experiment was performed in an orthotopic 4T1 breast cancer mouse model. The 4T1 breast cancer cell line was transfected to express mCherry fluorescence. The photograph on the left shows the bulk tumor after the overlying skin was lifted off. Within the skin overlying the tumor, a subtle area of thickening was observed, with a central area of discoloration (arrows in dashed white box). We then performed R-MR imaging of this area (middle image), which shows Raman signal (red) outlining the area. The Raman signal matches closely the mCherry fluorescence (right image) emitted from the skin, proving the presence of breast cancer cells in this location.

Figure 14:
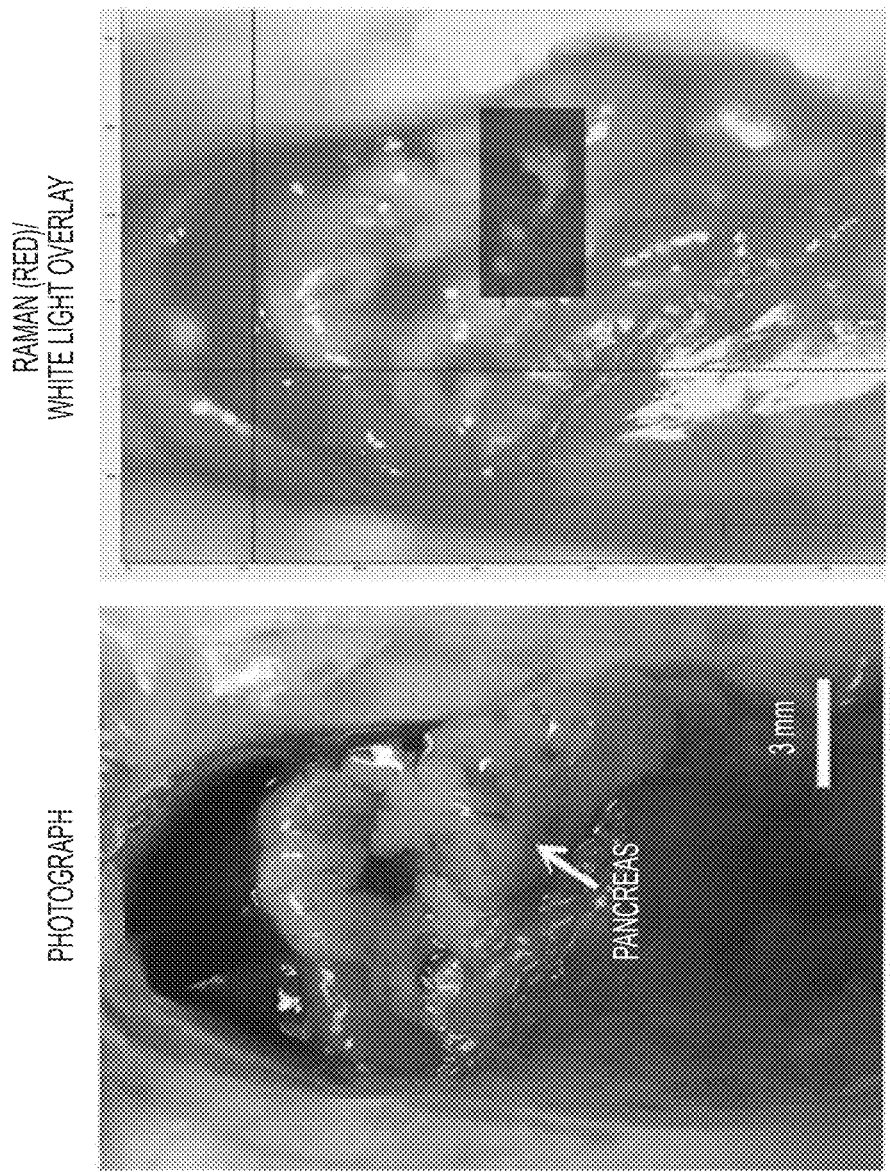

FIG. 14 shows how R-MR nanoparticles can be used to detect pancreatic cancer, according to an illustrative embodiment.

Figure 15:
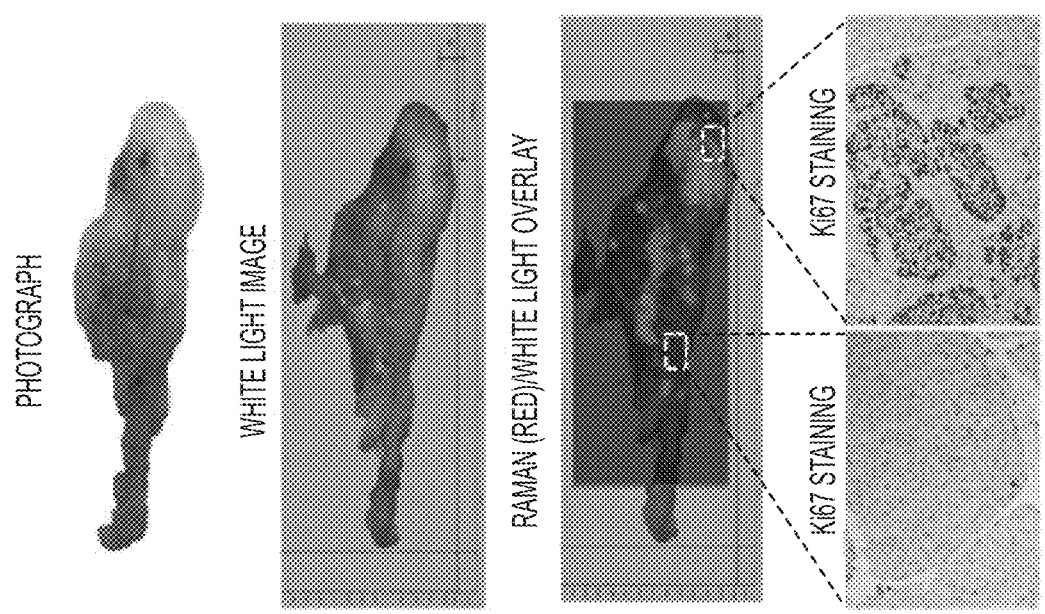

FIG. 15 shows an ex vivo high (1 micrometer) resolution Raman imaging of the excised pancreas from FIG. 14.

Figure 16:
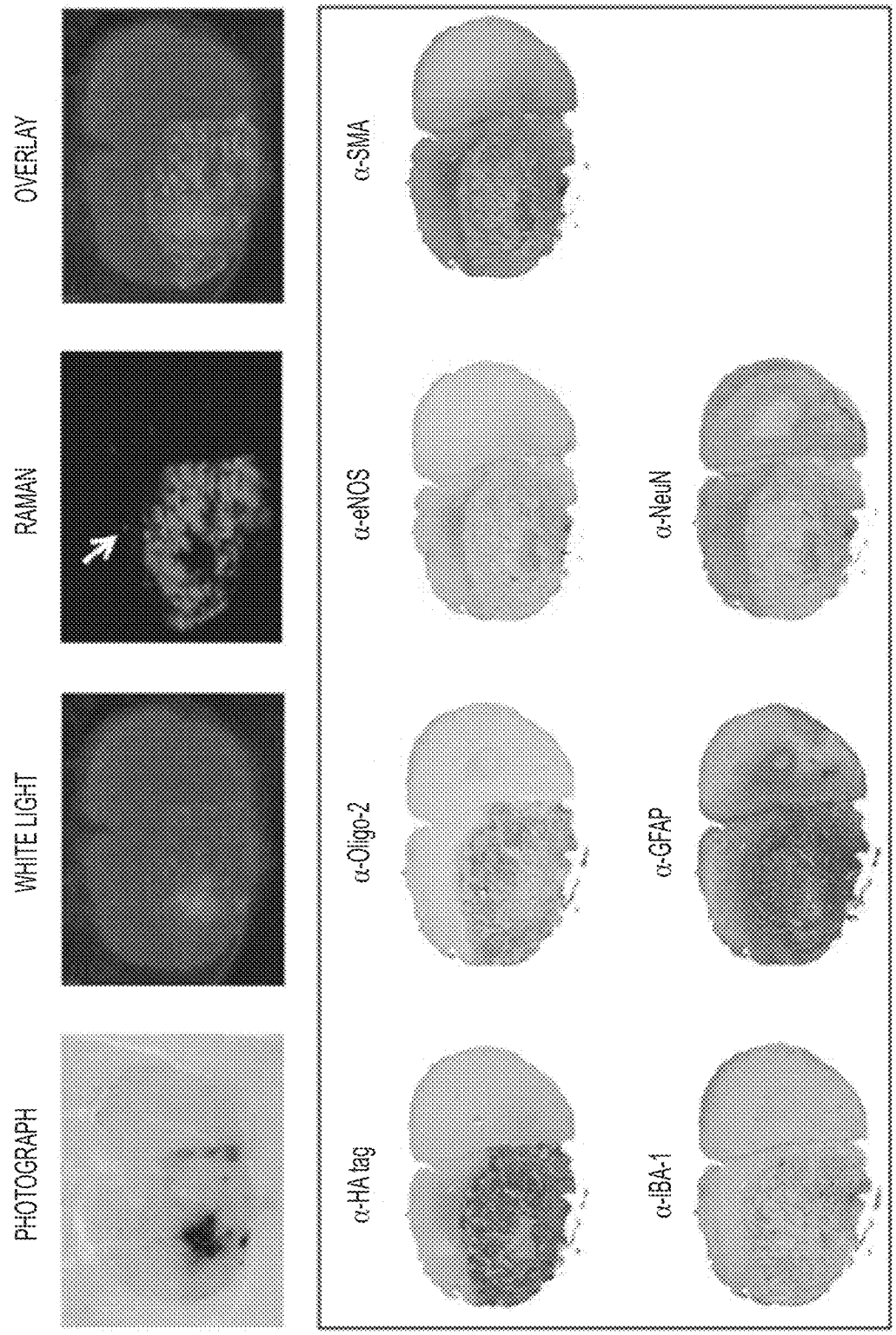

FIG. 16 shows how R-MR nanoparticles can be used to detect brain cancers in a genetic, spontaneous RCAS/tv-a glioblastoma model, according to an illustrative embodiment.

Figure 17:
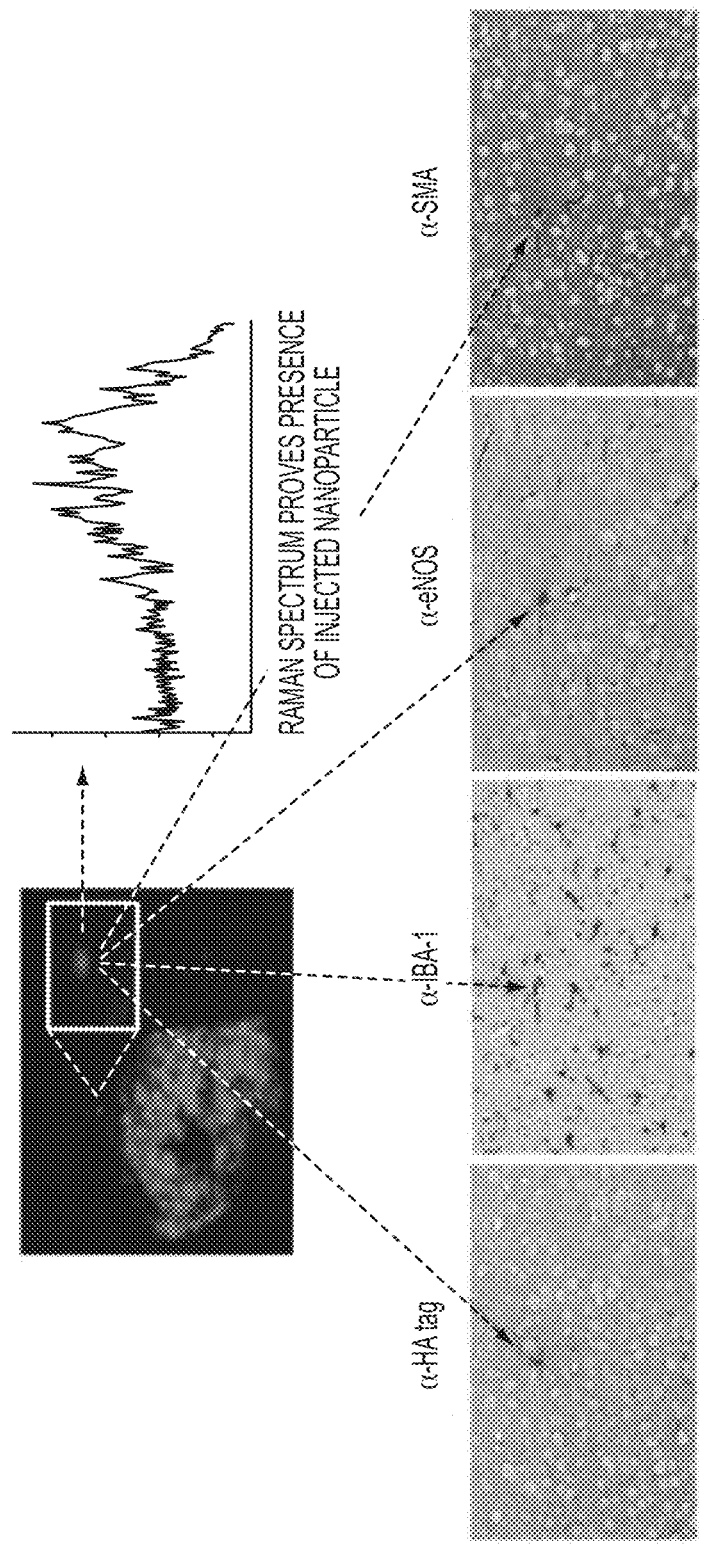

FIG. 17 shows how R-MR nanoparticles allow detection of single brain tumor cells, according to an illustrative embodiment.

Figure 18:
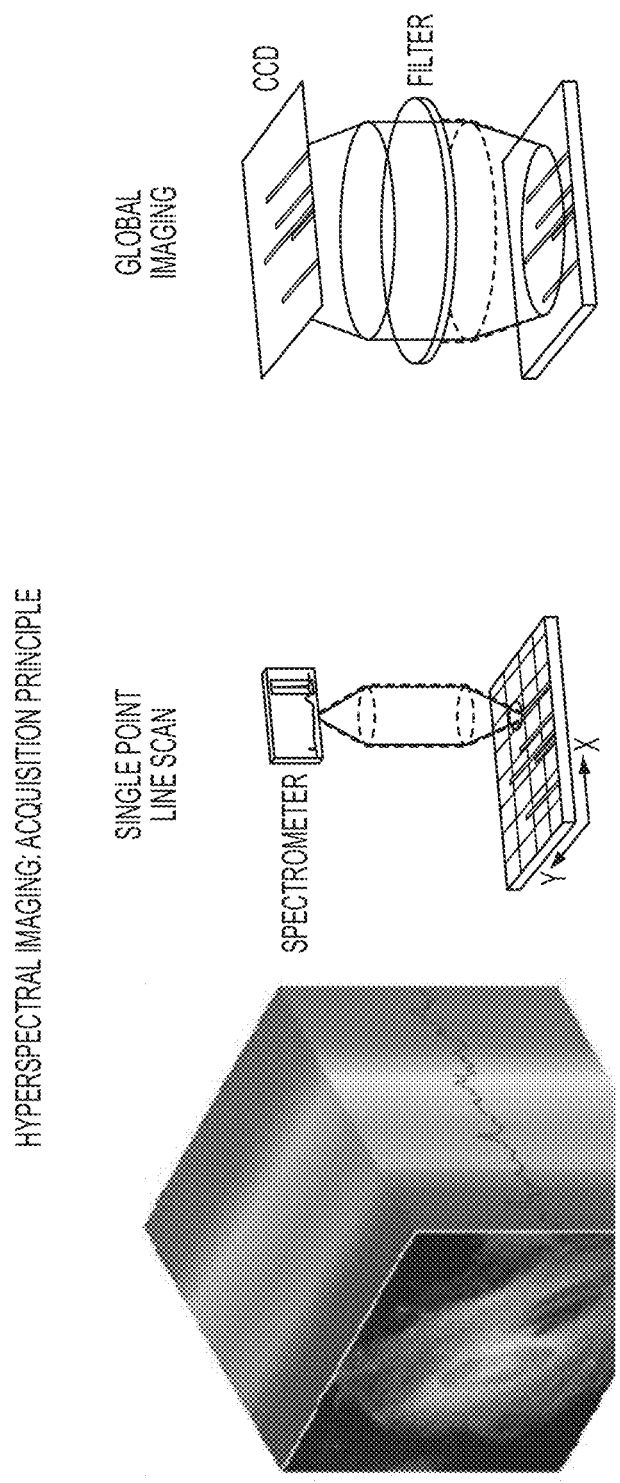

FIG. 18 is a schematic demonstrating differences between single point line scan methods and hyperspectral scanning/imaging, according to an illustrative embodiment.

Figure 19:
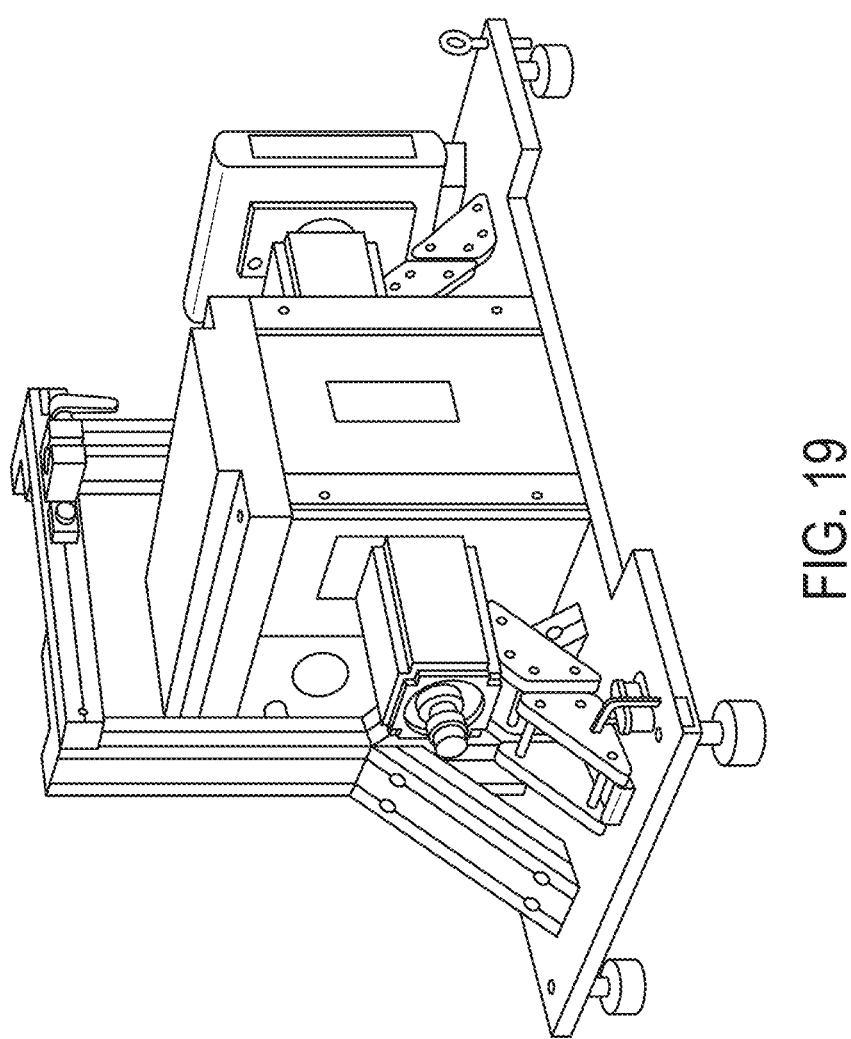

FIG. 19 is a schematic showing a widefield hyperspectral imaging camera which can be used (or components of which can be used) in an illustrative embodiment.

Figure 20:
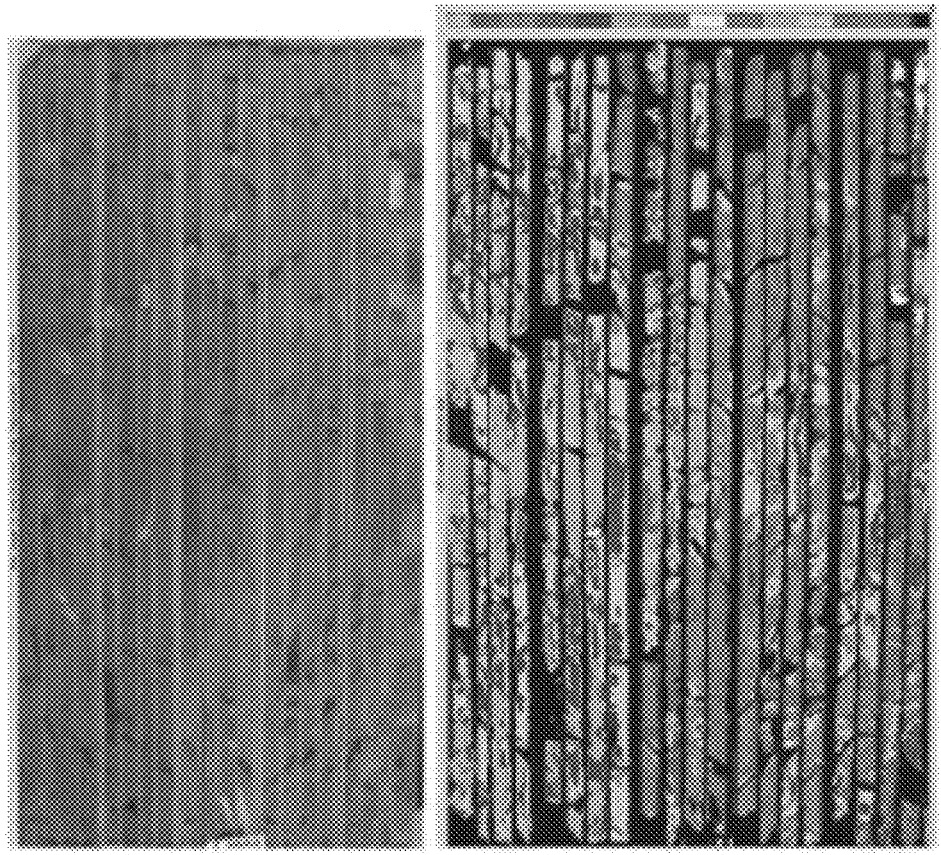
Figure 20:
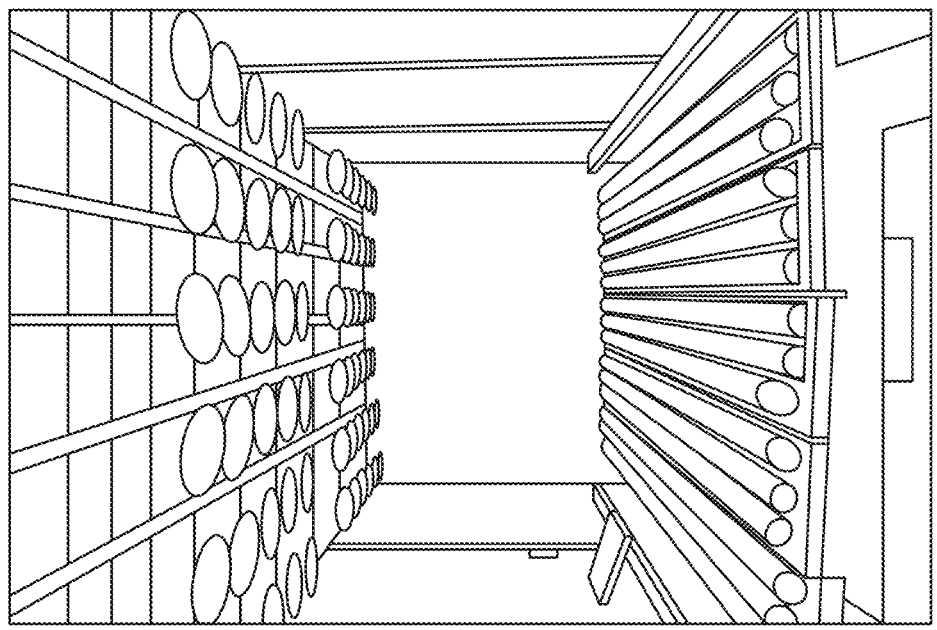

FIG. 20 shows images of geological material acquired with a widefield hyperspectral camera developed by Photon etc. of Montreal QC Canada.

Figure 21:
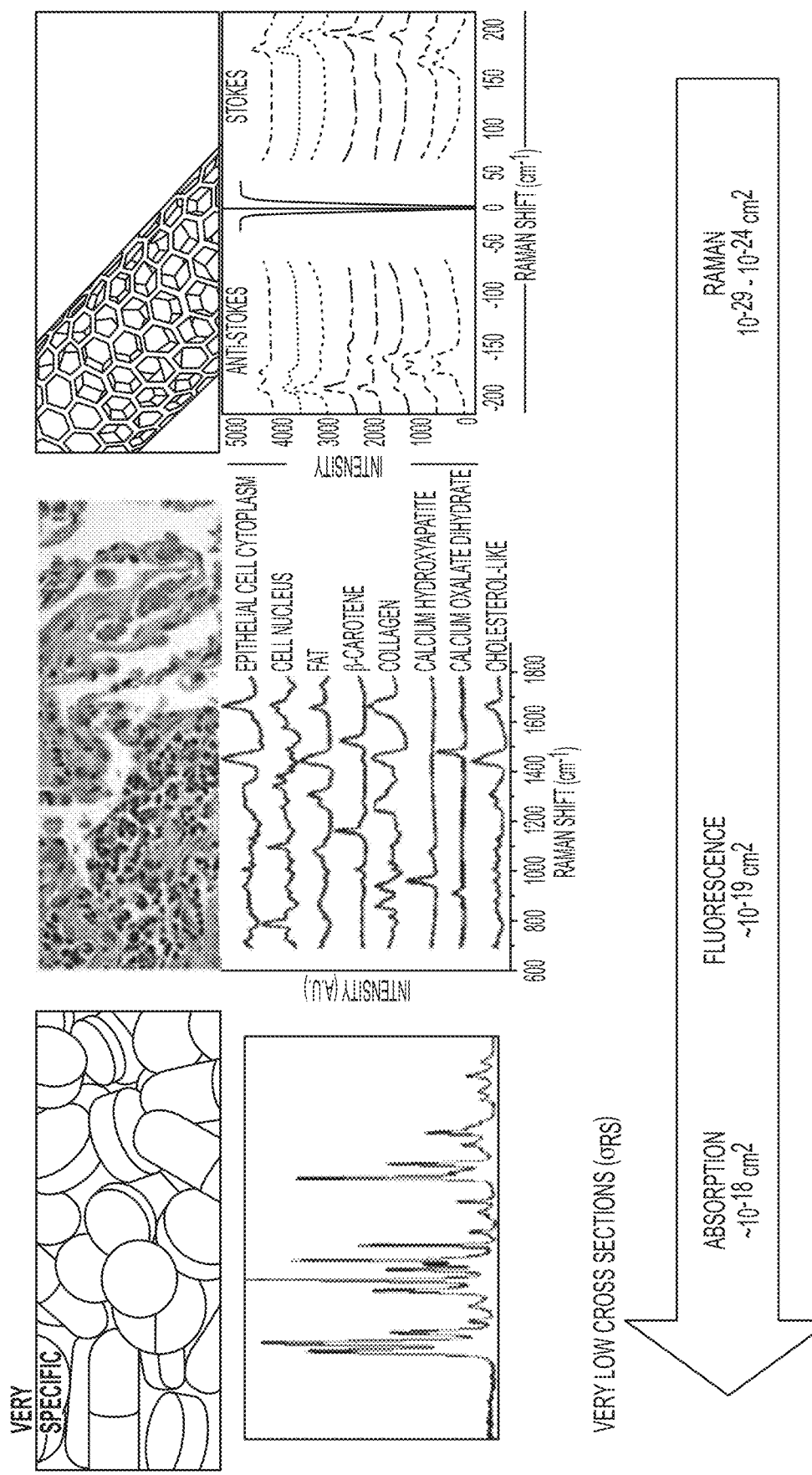

FIG. 21 is a schematic demonstrating advantages and challenges of traditional Raman spectroscopy.

Figure 22:
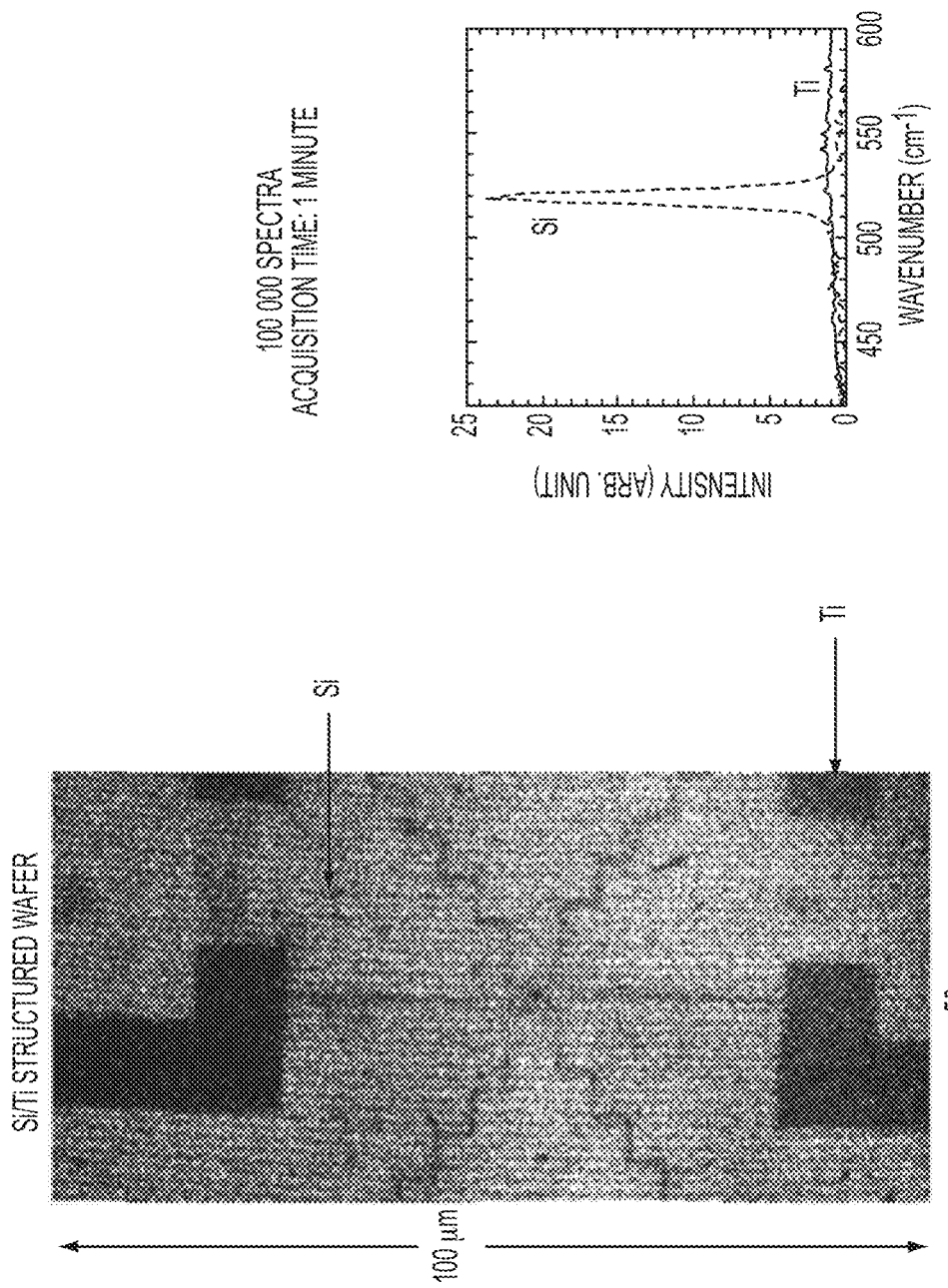

FIG. 22 shows feasibility of applying hyperspectral imaging technology to Raman spectroscopy, according to an illustrative embodiment.

Figure 23:
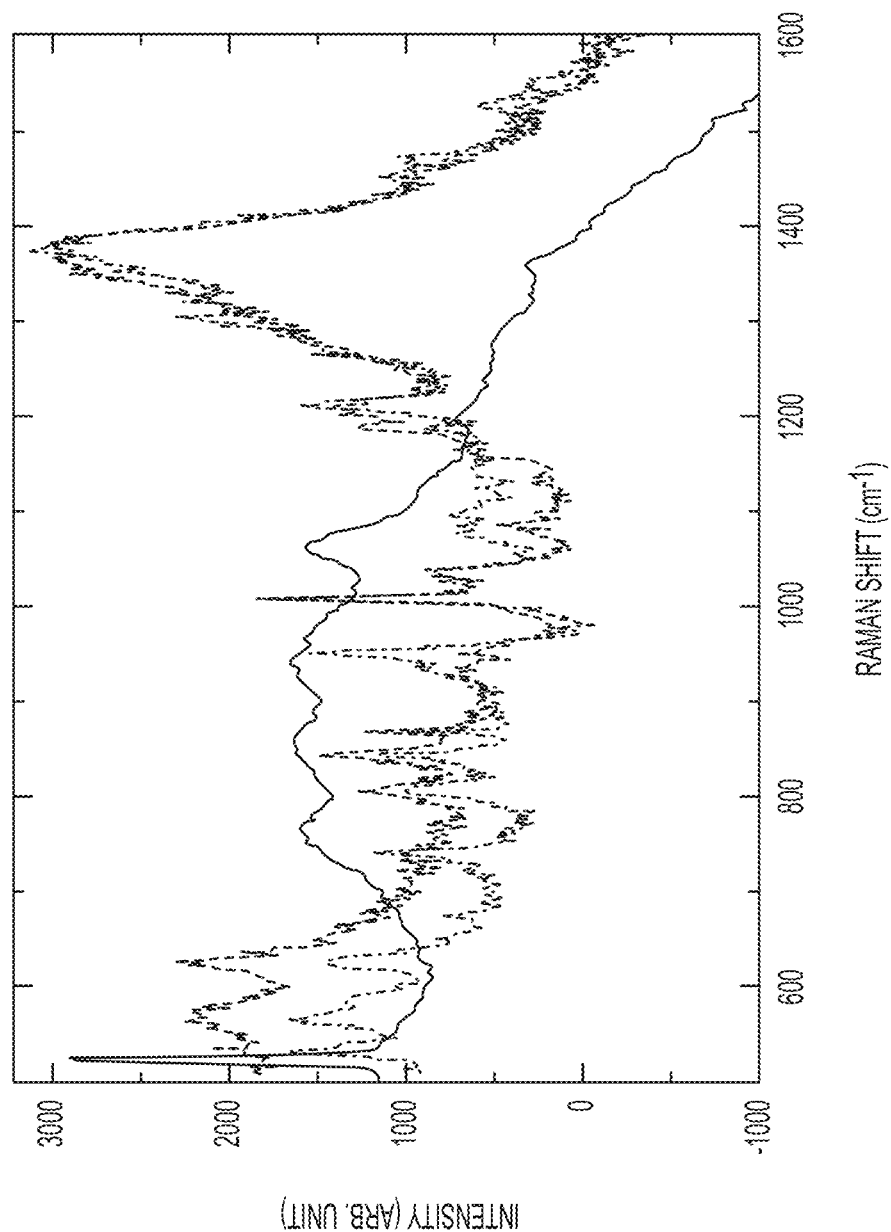

FIG. 23 shows data demonstrating that a Raman signal from the R-MR nanoparticles can be detected with a prototype Raman scanner.

Figure 24A:
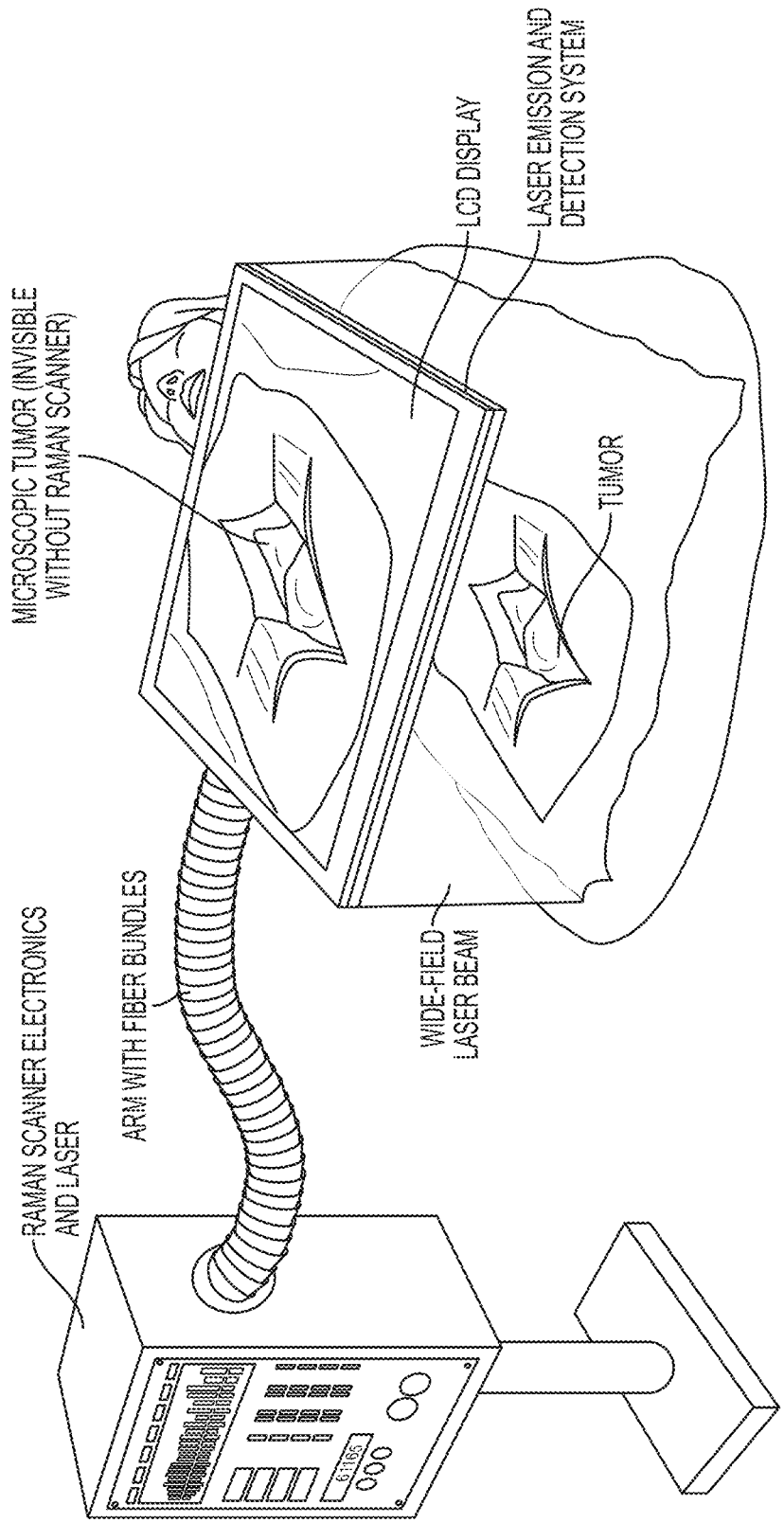

FIG. 24A shows a constructive embodiment of a Raman wide field scanner for use in the operating room. A surgeon can view a Raman image on an LCD screen (or other screen) built into the scanner, and can operate hands-free using the Raman information as real-time guidance. The viewing screen may display video superimposed with graphical indication of the location of R-MR nanoparticles. The screen may show a real-time (or near real-time) view of the operating bed. For example, the screen may show a real-time view of the patient and the surgeon's hands operating on the patient in real-time, thereby helping to guide the surgeon in removal of all portions of the tumor (or other abnormal material to be removed). Optics for directing and/or distributing a laser beam (or laser beams) over the wide field operating bed may be coupled to the screen (e.g., the back of the screen). A processor (not shown) is used for processing images and/or data for display. Resolution of the view may be adjusted during surgery. For example, once larger portions of tumor (or other abnormal) tissue are removed, the zoom may be adjusted for magnified viewing of the operating site, for example, for R-MR nanoparticle-enhanced microsurgical resection of tumor (or other abnormal) tissue.

Figure 24B:
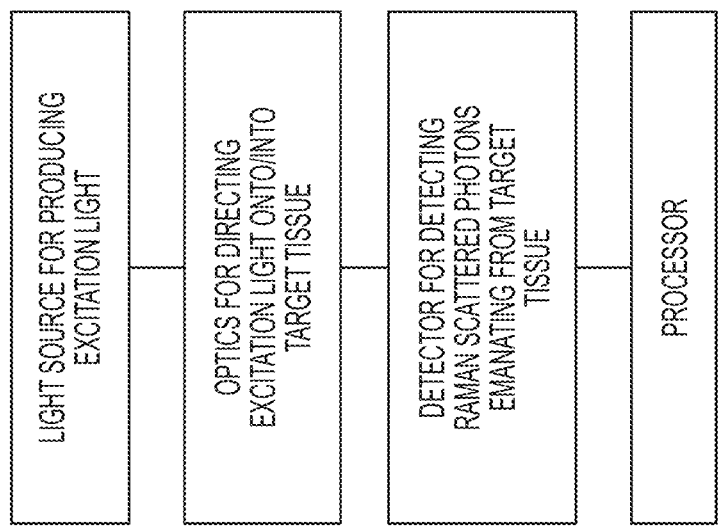

FIG. 24B is a schematic diagram of a wide field Raman imaging apparatus including at least one light source for producing excitation light, optics for directing the excitation light onto and/or into a target tissue, a detector for detecting Raman scattered photons emanating from the target tissue following illumination by the excitation light, and a processor configured to process data corresponding to the Raman scattered photons detected from the target tissue and to produce an image depicting a wide field corresponding to the target tissue. The detected Raman scattered photons are indicative of the presence of a Raman reporter in and/or upon the target tissue, and the image produced by the processor visually indicates position and/or intensity of the Raman reporter within the wide field. The apparatus may additionally include a display for displaying the image, for example, a real-time series of such images, to a surgeon during surgery.

Figure 25:
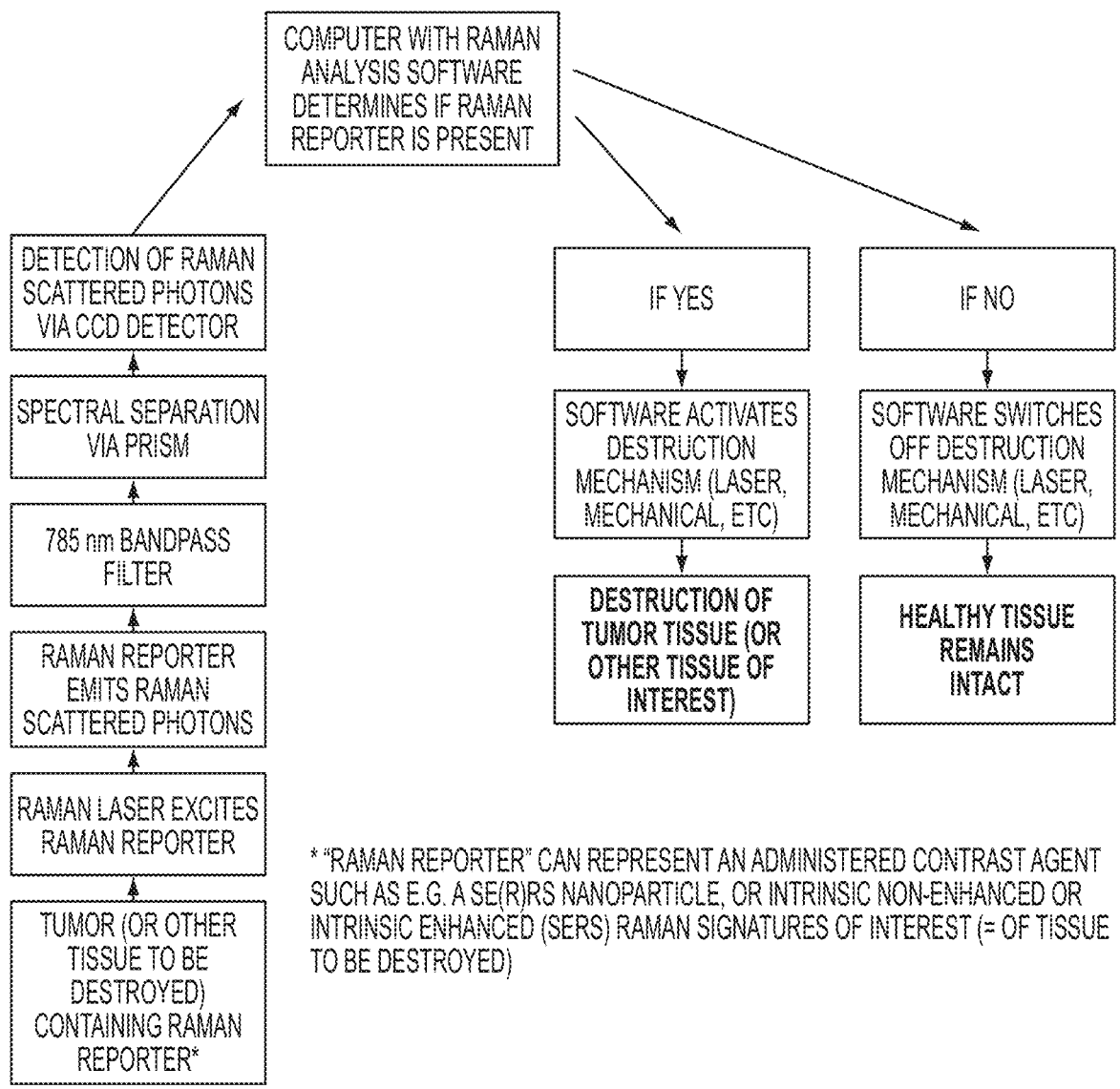

FIG. 25 is a schematic illustration of steps of an exemplary Raman reporter interrogation and ablation/resection method, according to an illustrative embodiment.

Figure 26:
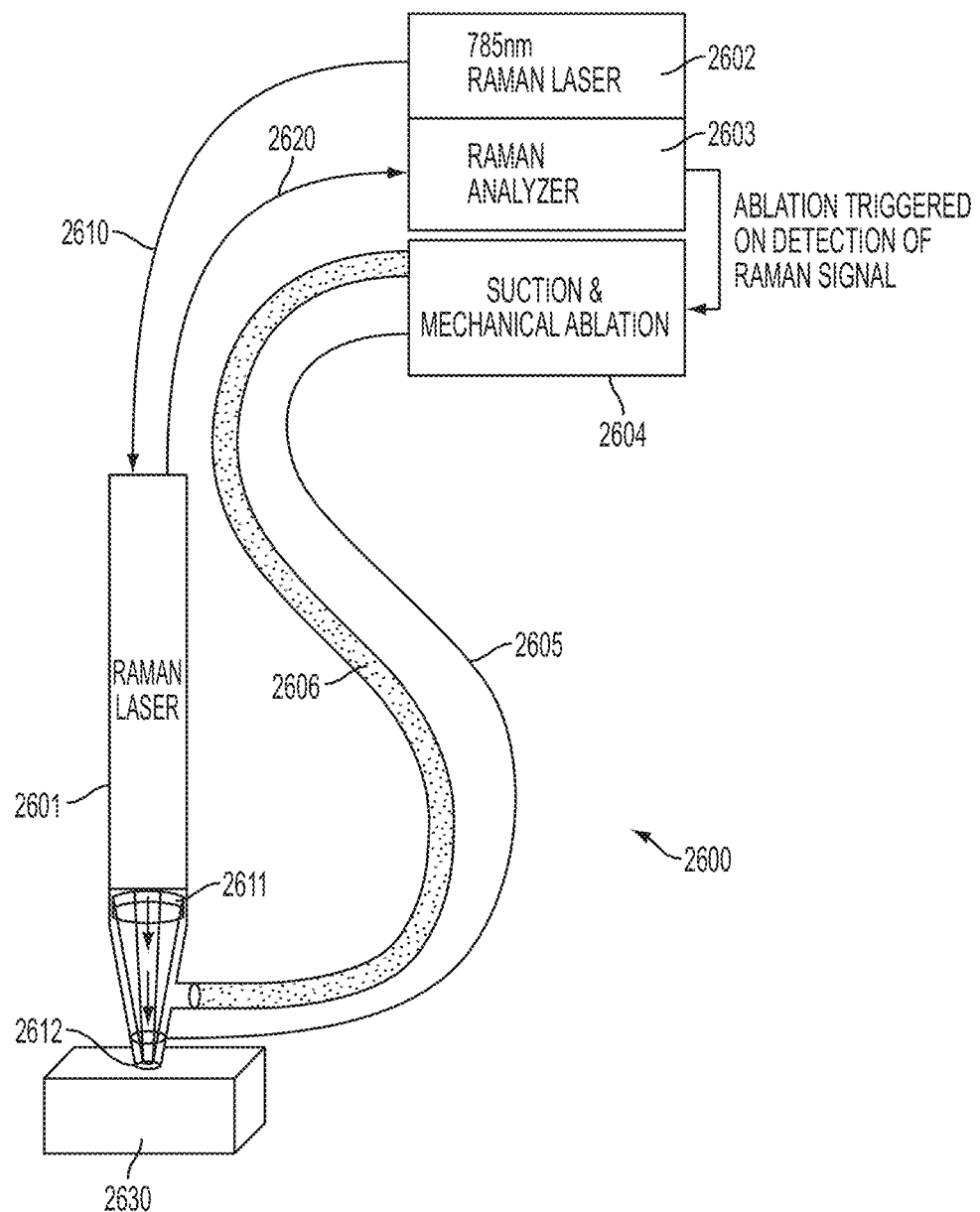

FIG. 26 is a schematic illustration of an exemplary Raman interrogation and ablation/resection system, according to an illustrative embodiment.

Figure 27:
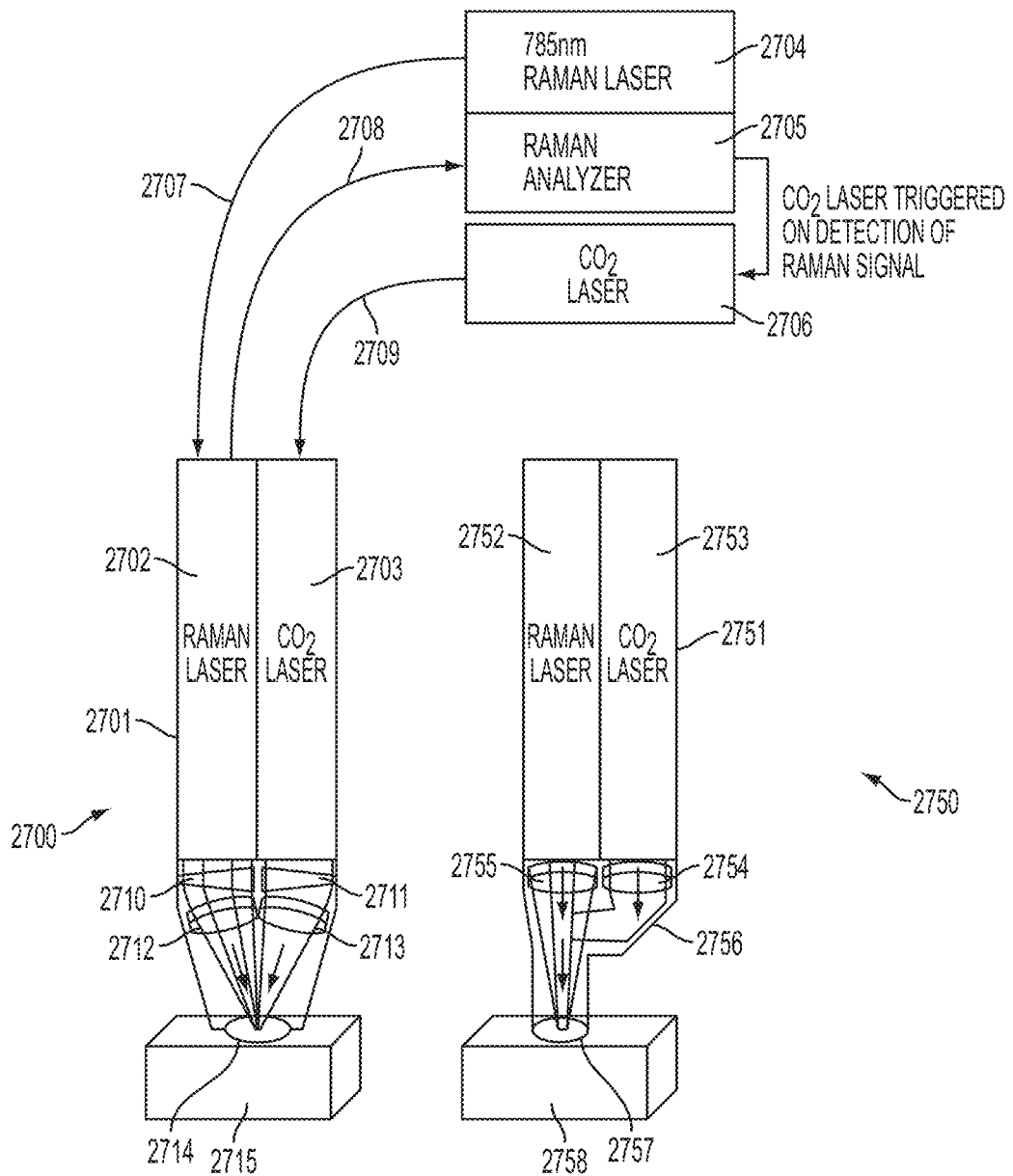

FIG. 27 is a schematic illustration of an exemplary Raman interrogation and ablation/resection system, according to an illustrative embodiment.

Figure 28:
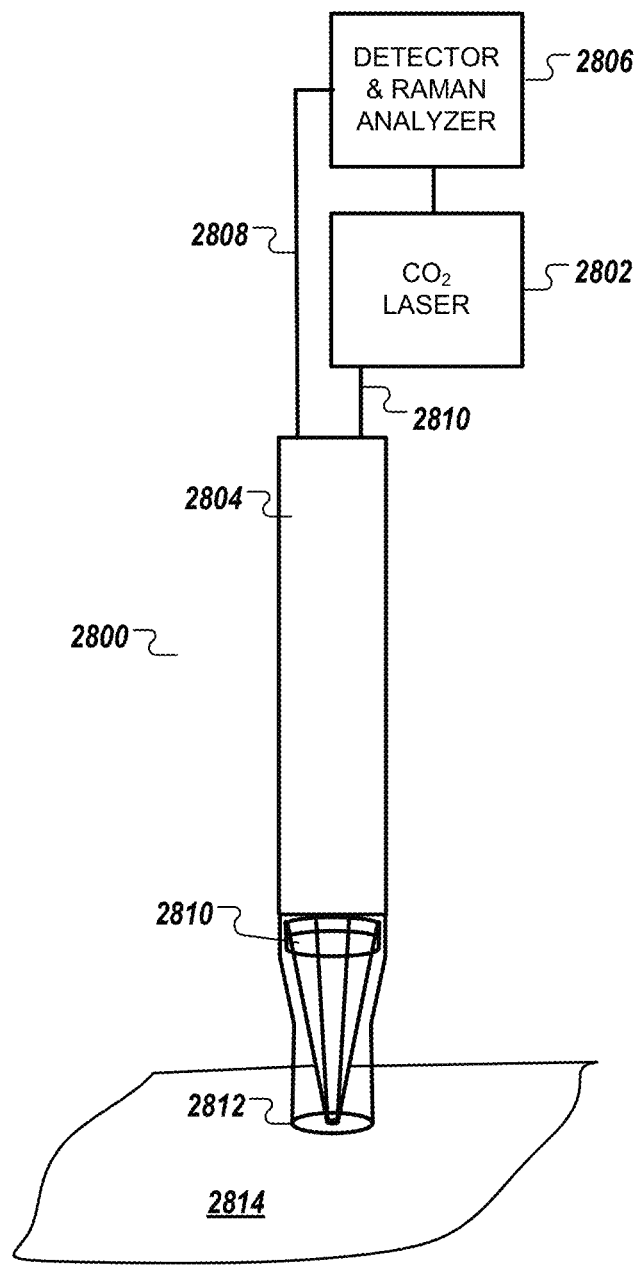

FIG. 28 is a schematic illustration of an exemplary Raman interrogation and ablation/resection system, according to an illustrative embodiment.

Figure 29:
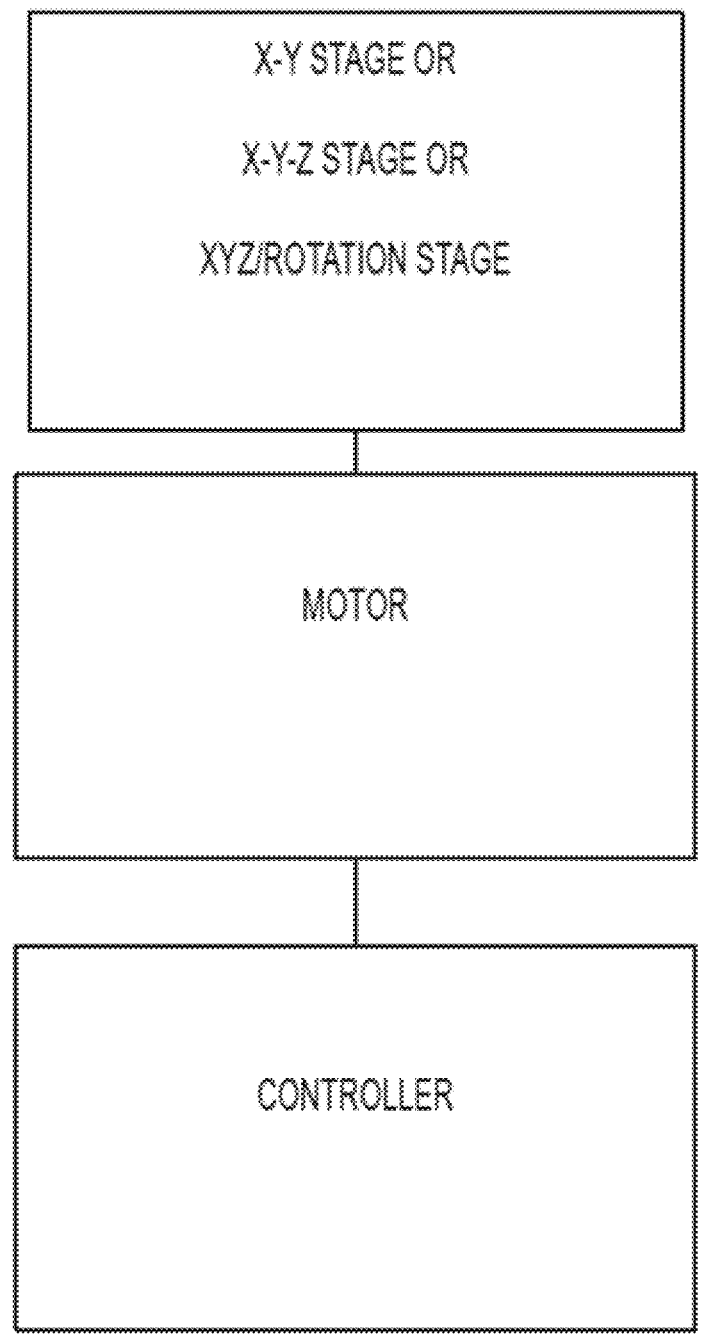

FIG. 29 is a schematic illustration of a system for controlling a Raman scanner according to an illustrative embodiment.

Figure 30:
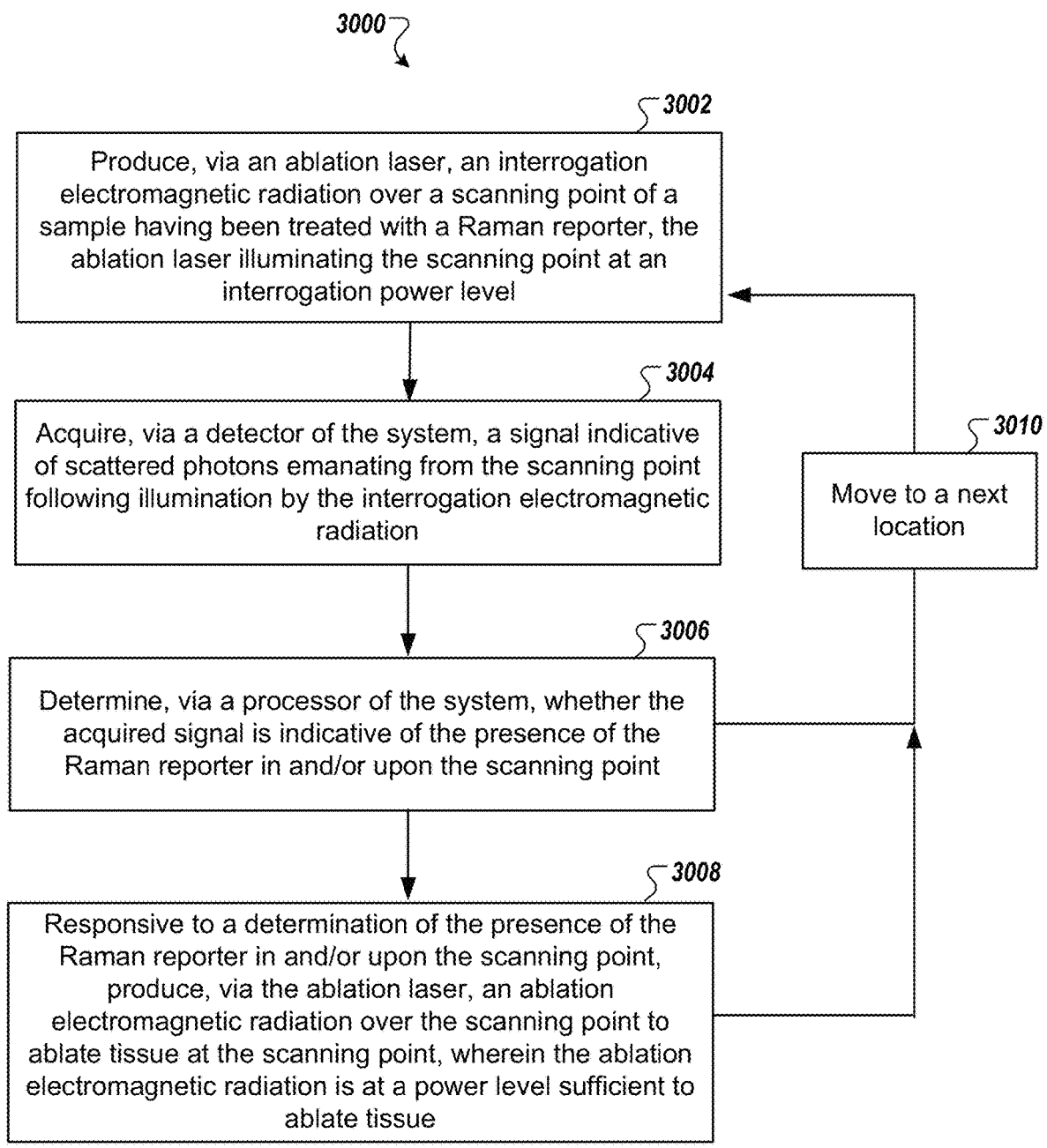

FIG. 30 is a schematic illustration of an imaging and ablation exemplary method of the disclosure.

Figure 31A:
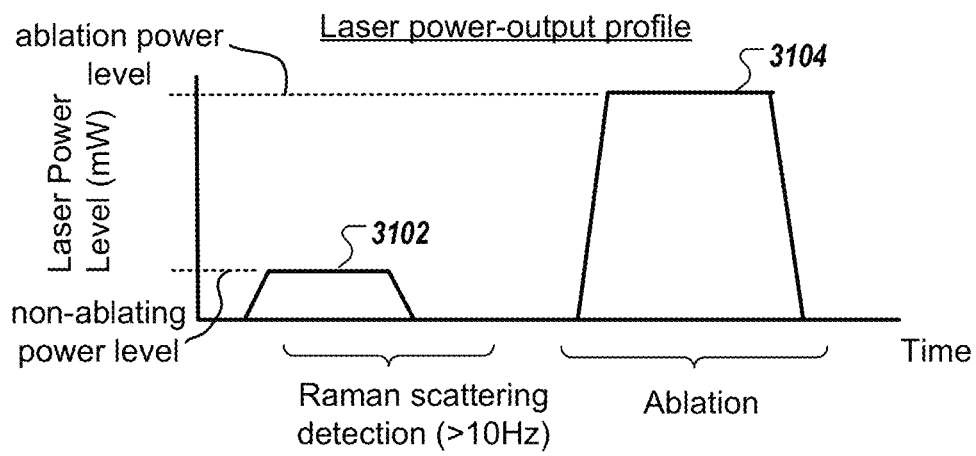
Figure 31B:
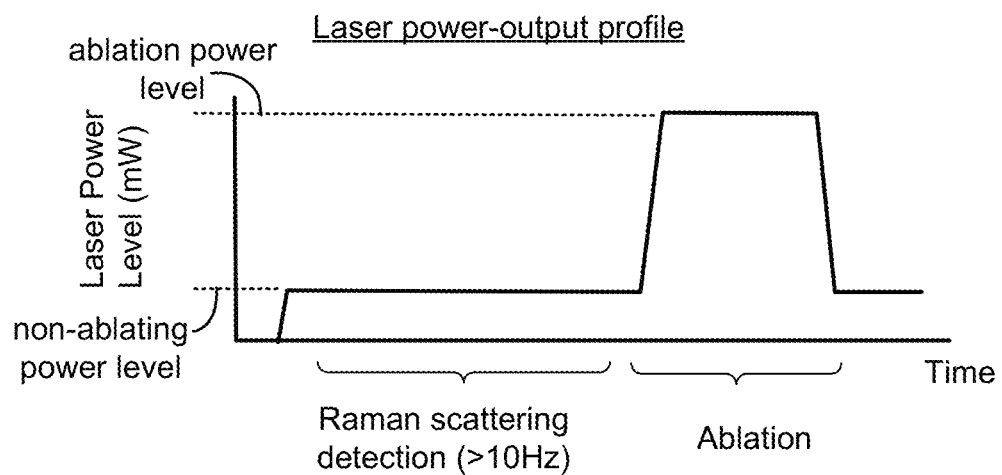

FIGS. 31A and 31B are schematic illustrations of an exemplary method of controlling a laser ablation and Raman scanning device, according to an illustrative embodiment.

Figure 32:
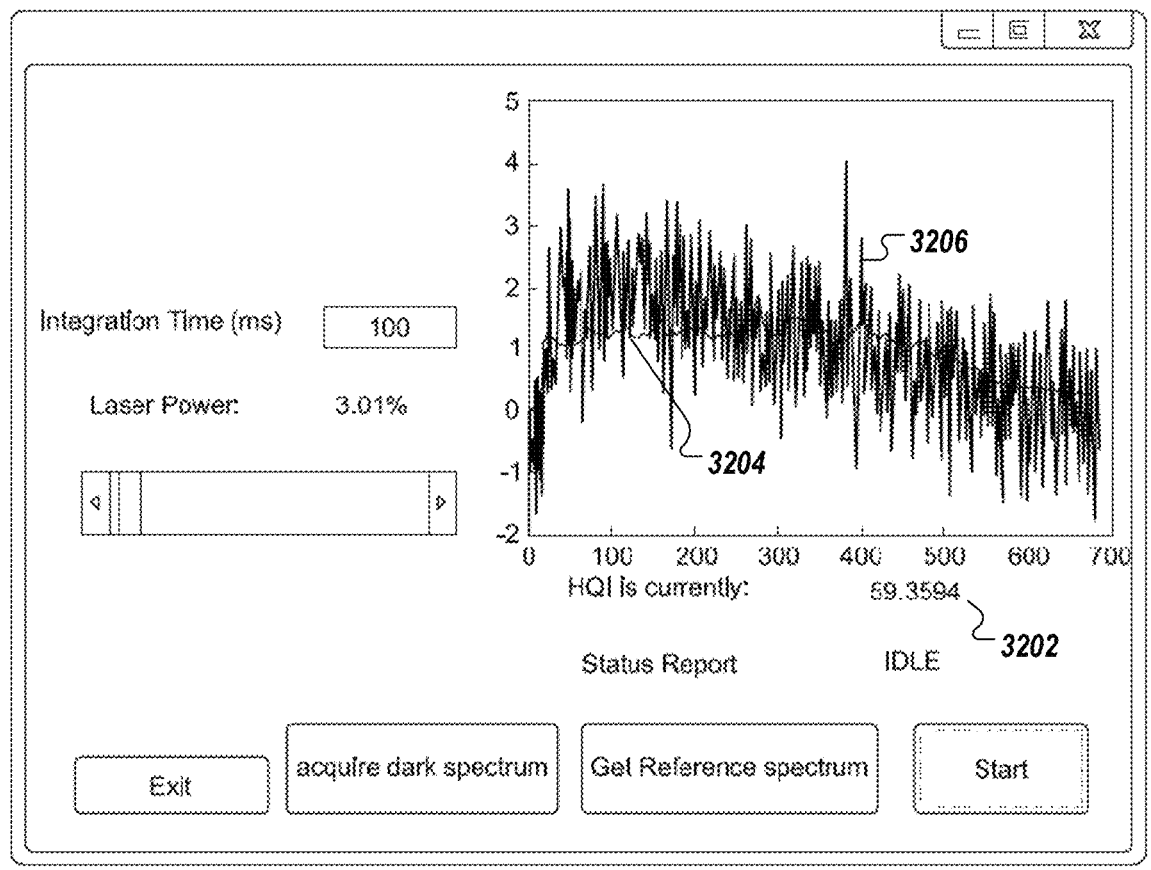

FIG. 32 is a schematic illustration of an exemplary graphic user interface for controlling a laser ablation and Raman scanning device, according to an illustrative embodiment.

Figure 33:
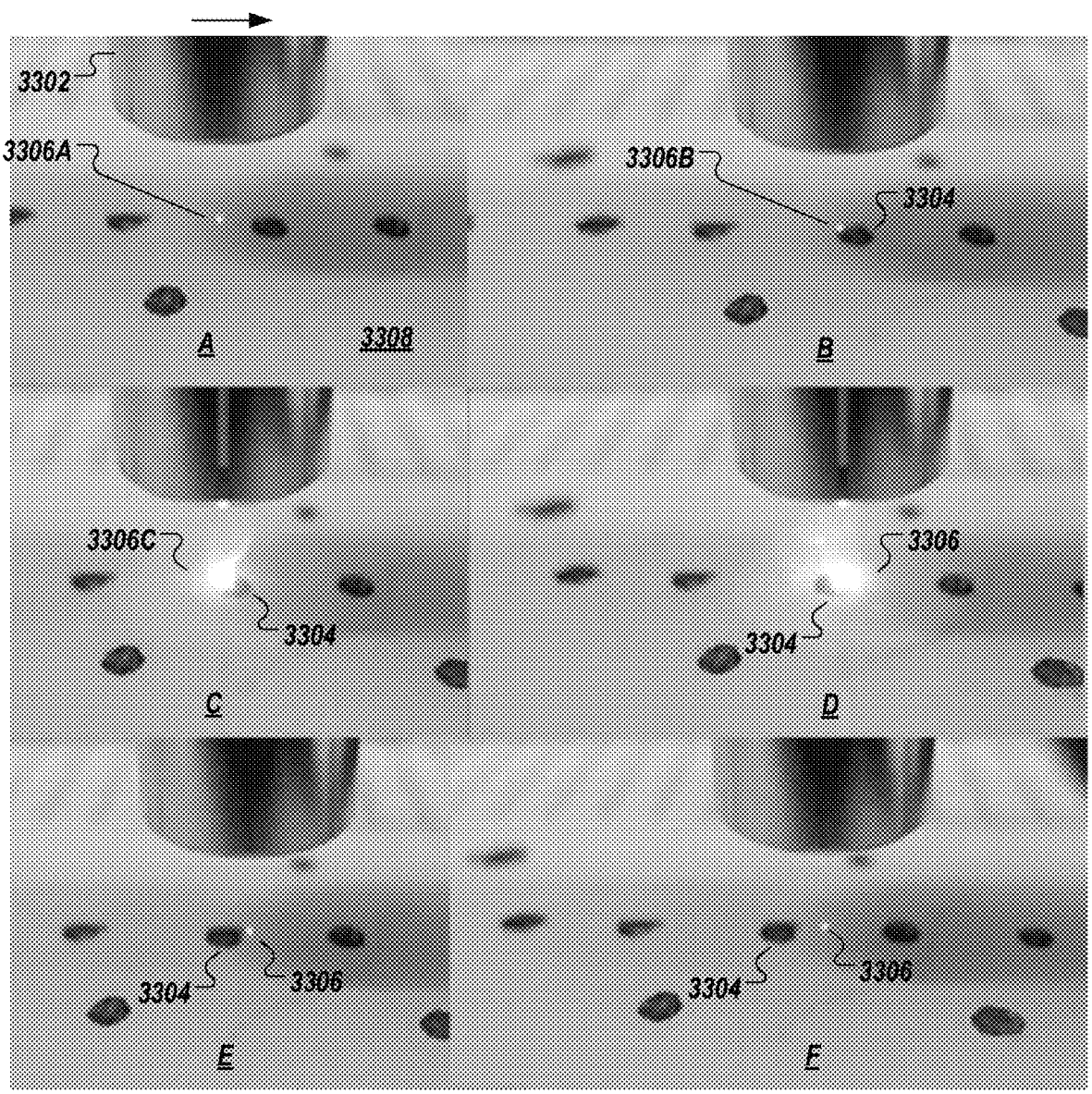

FIG. 33 shows images of an exemplary Raman scanning and ablation system during interrogation and ablation, according to an illustrative embodiment.

Figure 34:
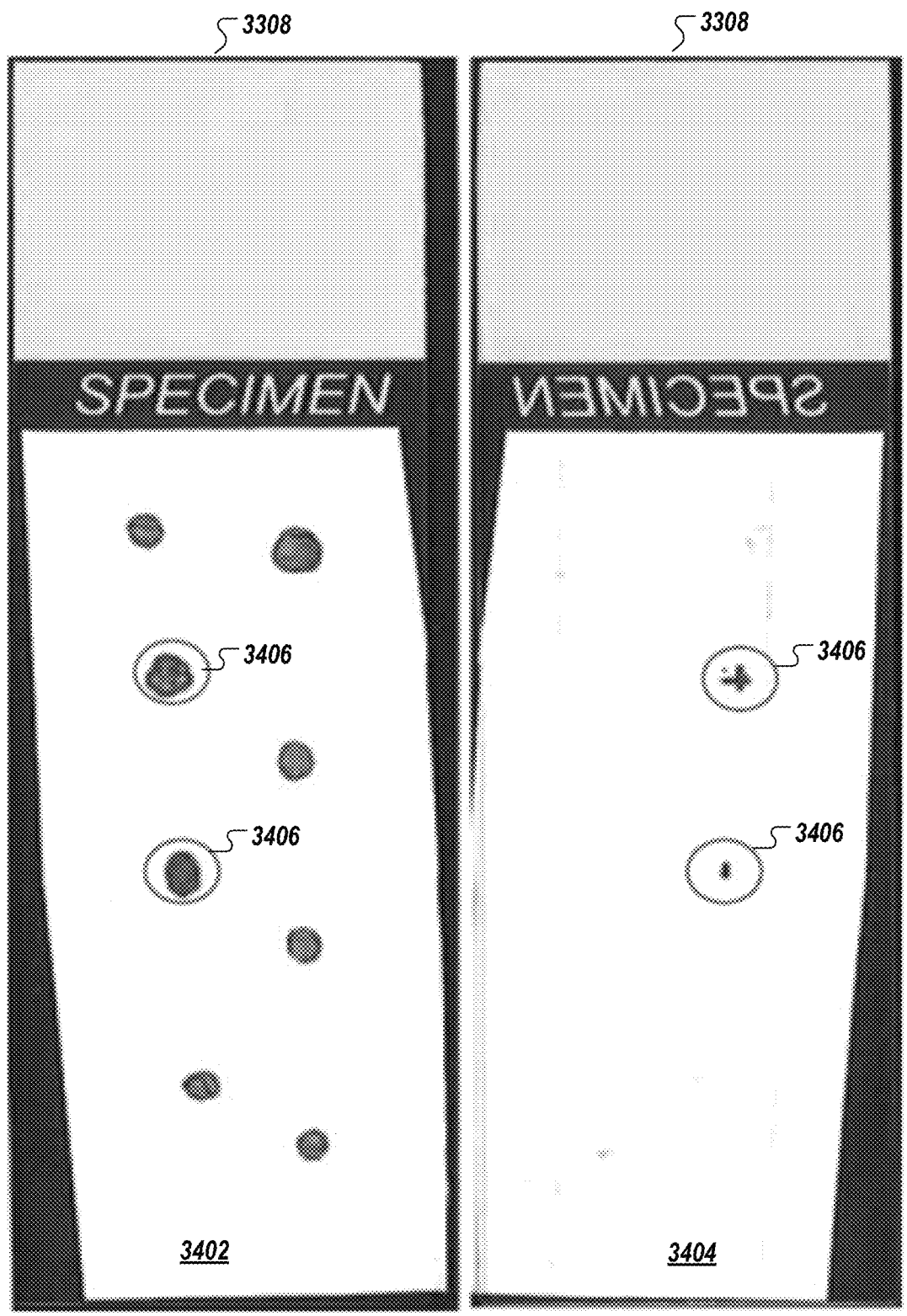

FIG. 34 shows images after being scanned and ablated by the Raman scanning and ablation system. The left and right images shows the top and bottom side of the sample that was treated with the Raman reporter and exposed to scanning by the ablation system.

All publications, patent applications, patents, and other references mentioned herein, are incorporated by reference in their entirety. In case of conflict, the present specification, including definitions, will control. In addition, the materials, methods, and examples are illustrative only and not intended to be limiting. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

Other features and advantages of the invention will be apparent from the following detailed description, and from the claims.

DETAILED DESCRIPTION

Headers are used herein to aid the reader and are not meant to limit the interpretation of the subject matter described.

Raman spectroscopy is an emerging technology that allows nondestructive analysis of matter by assessing wavelength shift of photons after interaction with specific atomic bonds. While intrinsic (non-amplified) Raman signatures of tissues have shown promise in distinguishing malignant tissues from benign ones, typical acquisition times for such spectra are at least 10 seconds per spectrum; such times simply cannot provide sufficient speed for surgical workflow.

Figure 1:
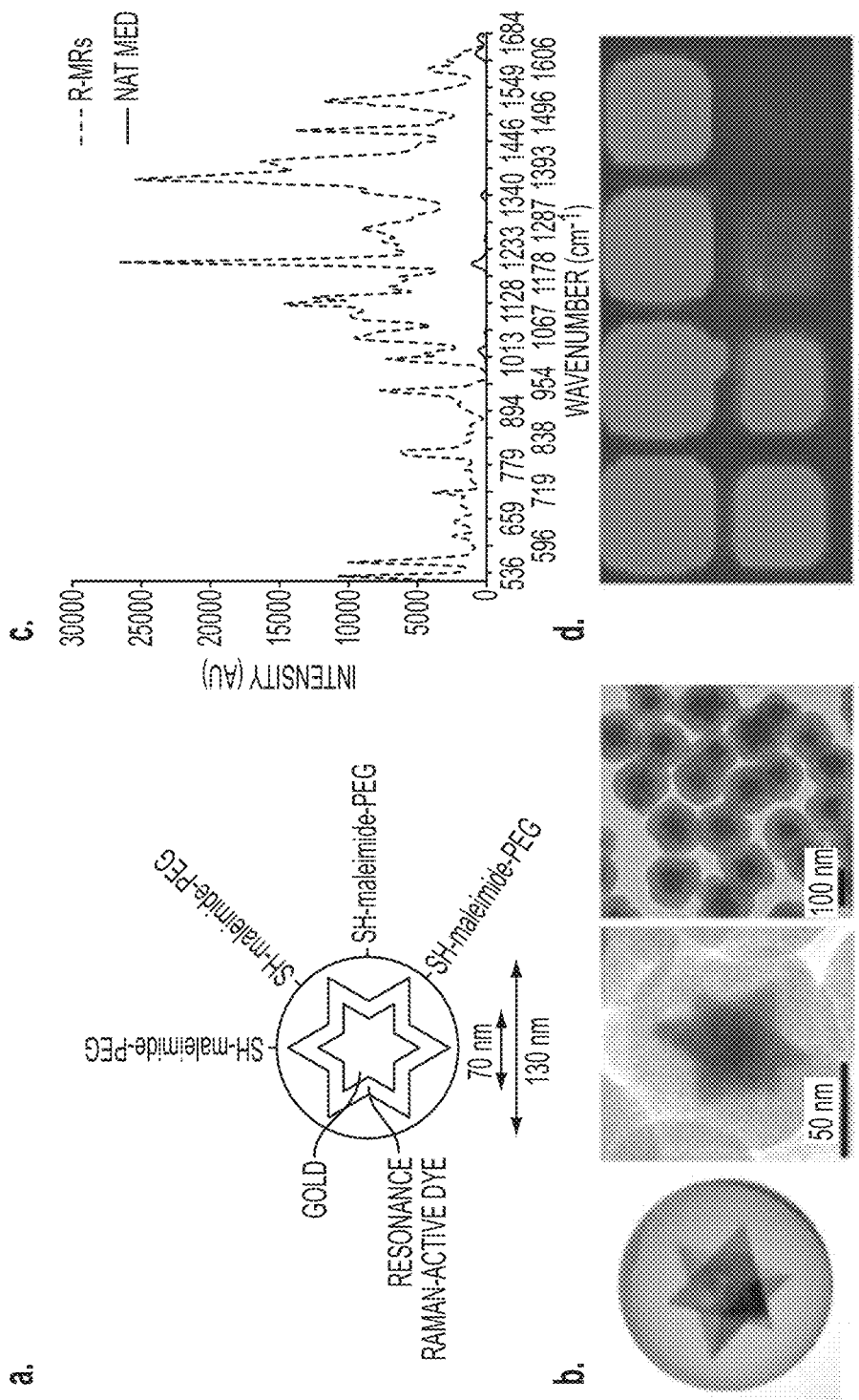
FIG. 1A shows a Raman-MRI (R-MR) nanoparticle used in conjunction with the wide-field Raman scanner/imaging apparatus described herein, according to an illustrative embodiment.
FIG. 1B is a computer rendering and electron microscopy images of the R-MR nanoparticle.
FIG. 1C is an exemplary Raman spectrum and intensity comparison of the R-MR nanoparticles versus equimolar amounts of first generation nanoparticles.
FIG. 1D shows R-MR nanoparticles suspended in a 384 well plate phantom imaged with a Renishaw InVia Raman microscope.
Figure 2:
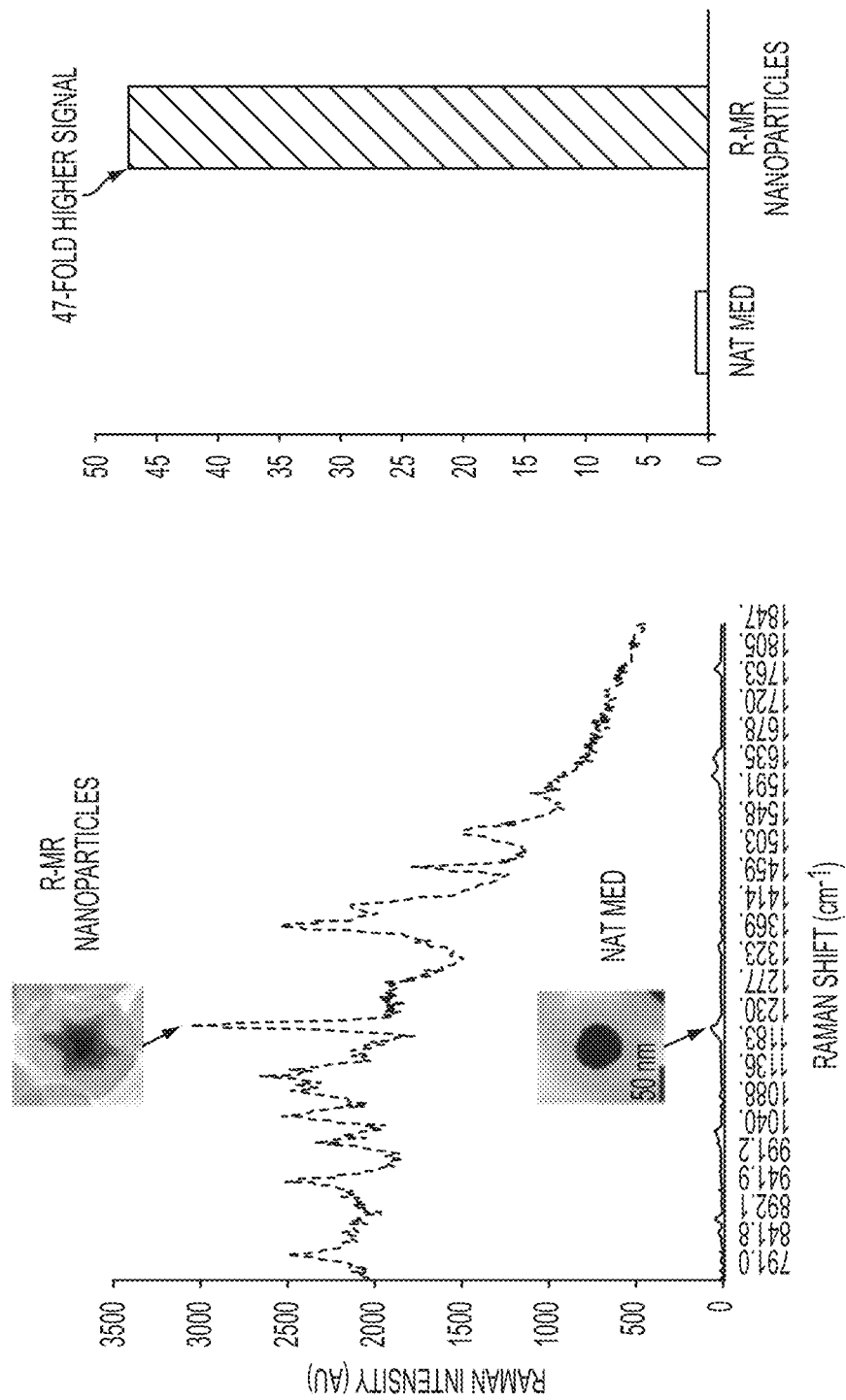
FIG. 2 shows a comparison of Raman signal intensity of R-MR nanoparticles and previous, first generation nanoparticles.
Figure 3:
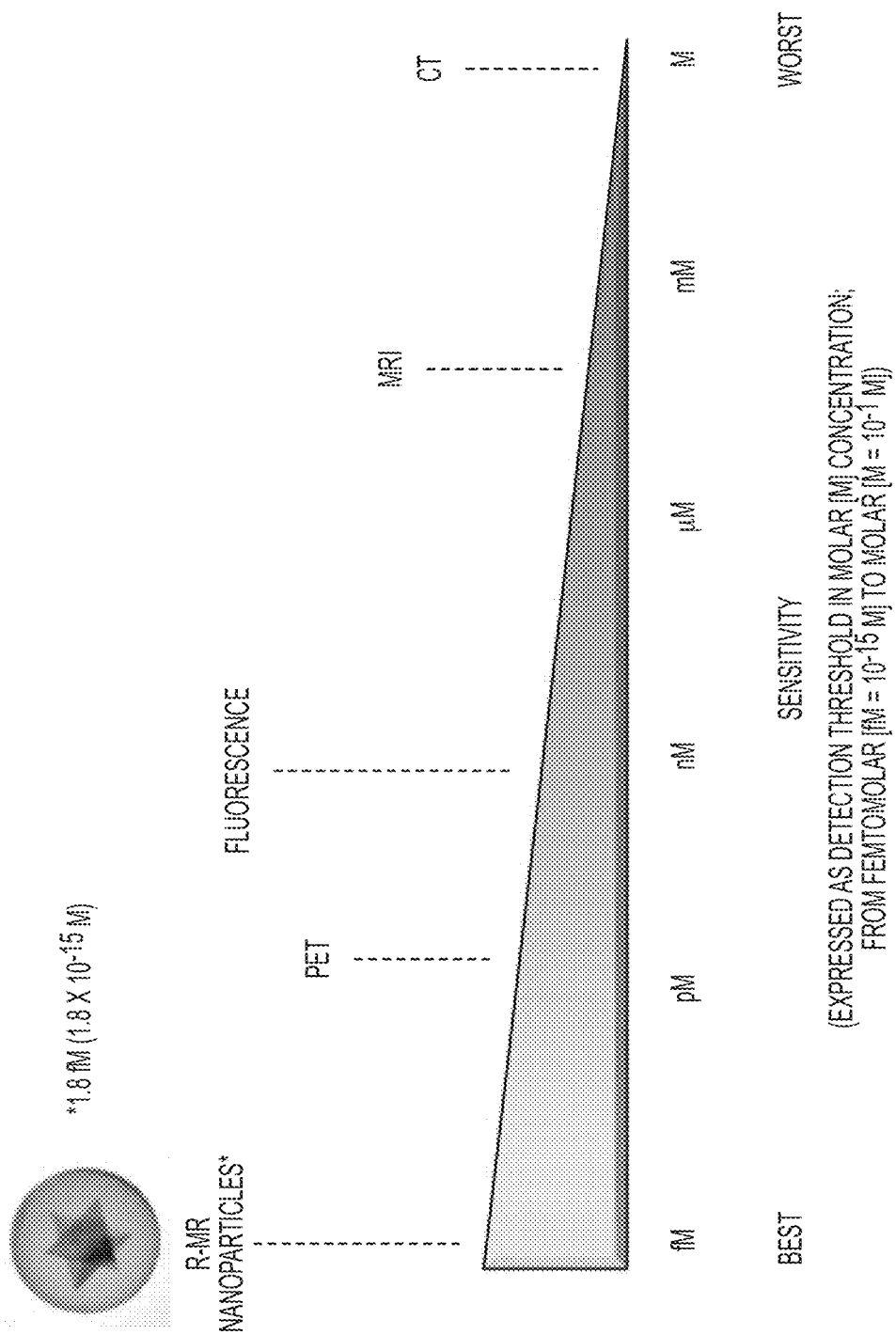
FIG. 3 shows a comparison of detection sensitivity between the Raman signal of the R-MR nanoparticles and other imaging modalities. R-MR nanoparticles have a detection threshold of 1.8×10-15 femtomolar [fM], and are therefore at least 3 orders of magnitude more sensitive than other ultra-sensitive imaging methods such as Positron-Emission Tomography (PET) or fluorescence imaging.
Figure 4:
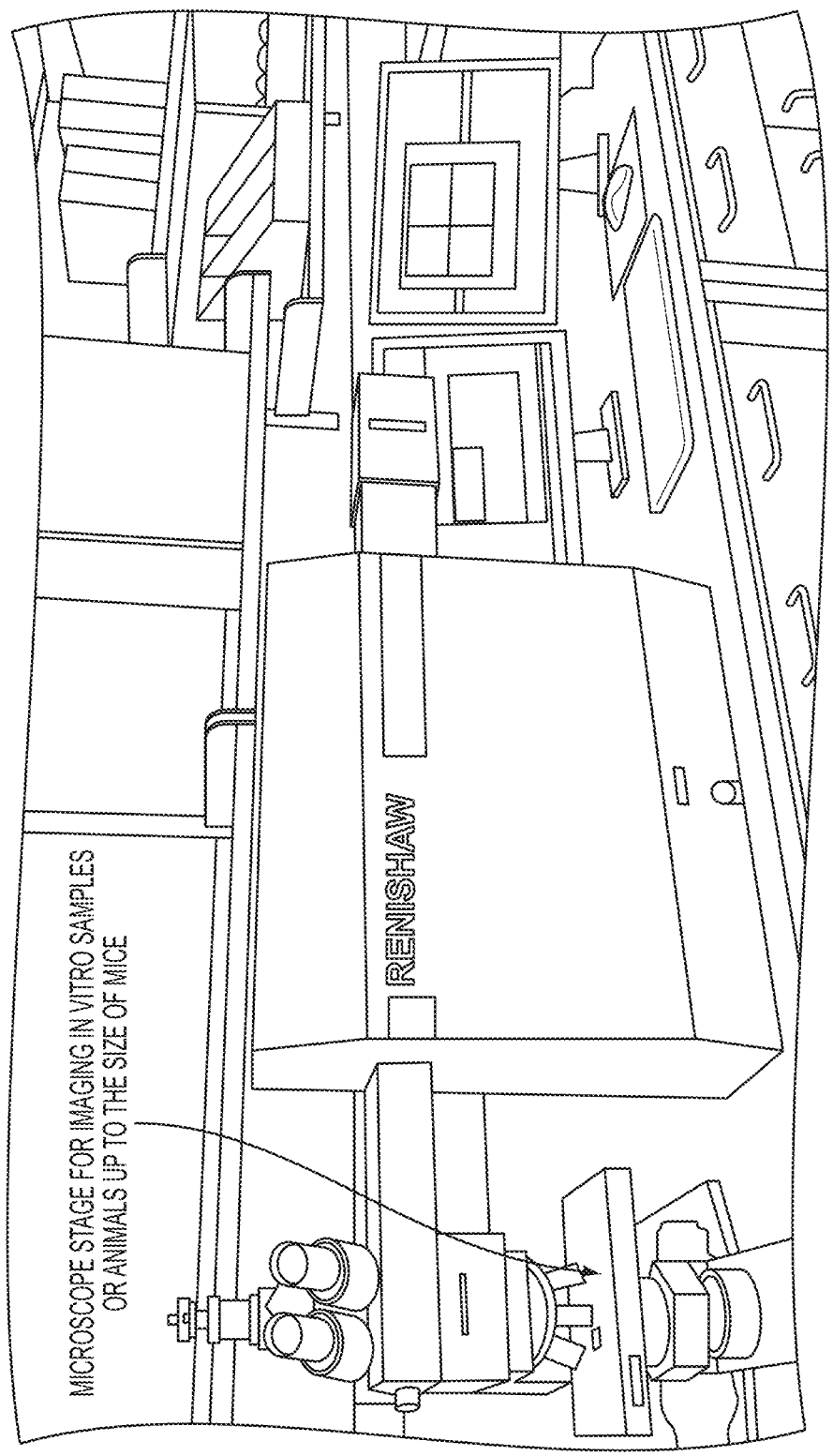
FIG. 4 shows the Renishaw InVia Raman microscope utilized to provide data presented in other Figures.
Figure 5:
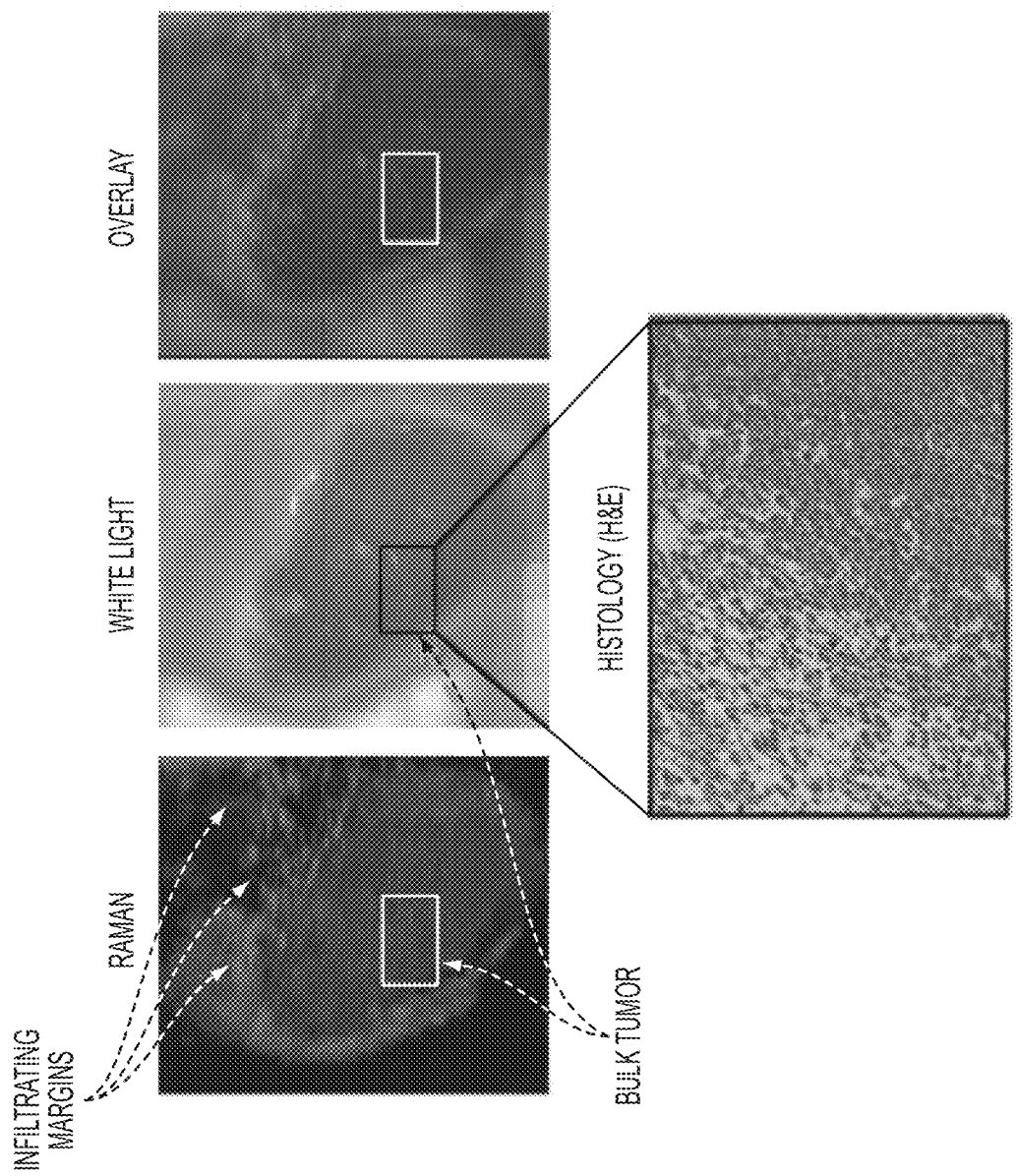
FIG. 5 shows how R-MR nanoparticles can be used to detect microscopic infiltration at tumor margins in a mouse with dedifferentiated liposarcoma implanted in the flank, according to an illustrative embodiment.
Figure 6:
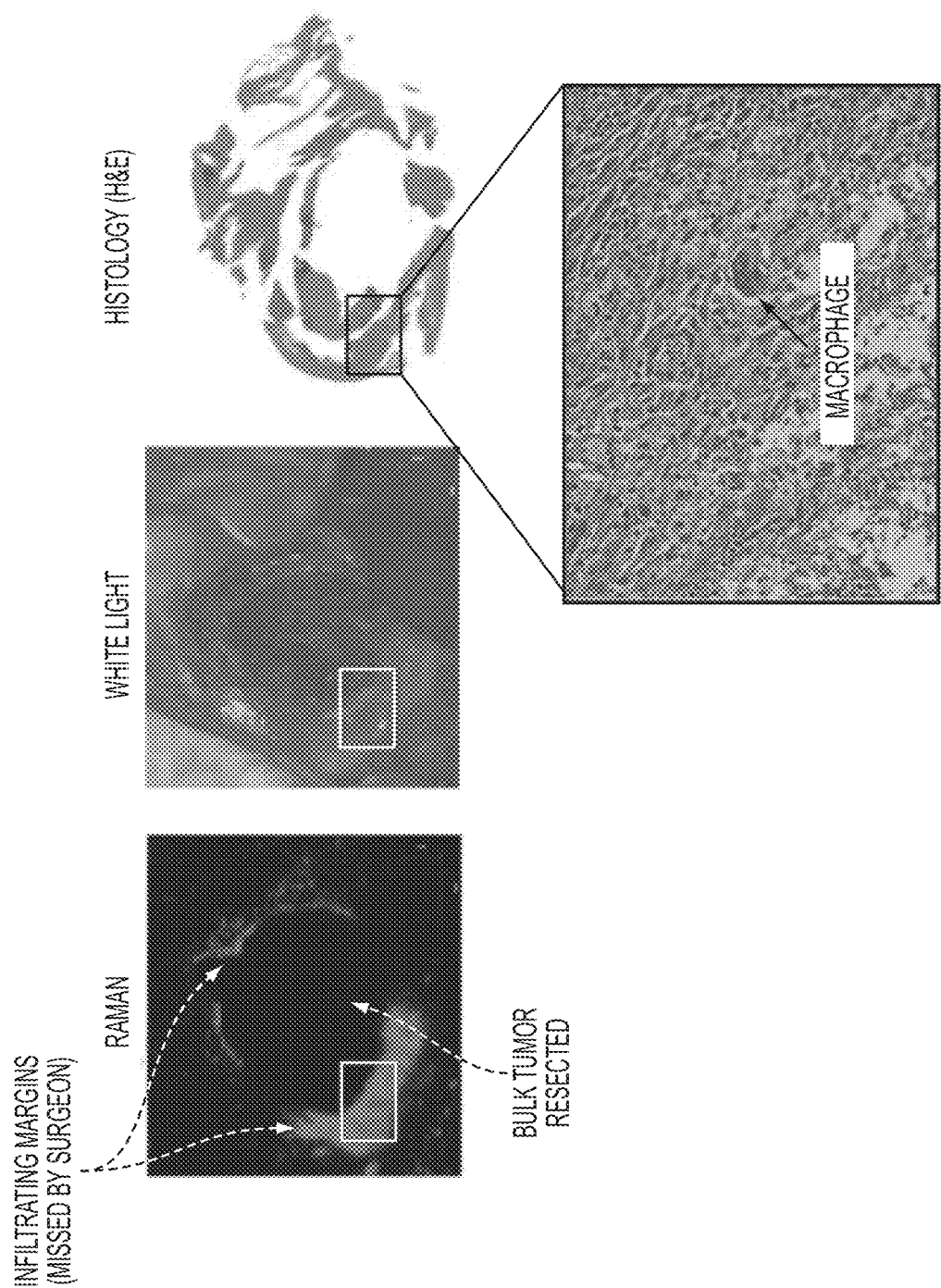
FIG. 6 shows how R-MR nanoparticles can be used to detect microscopic infiltration at tumor margins in the same mouse as FIG. 5, after resection of the bulk tumor by a board-certified surgeon using his unaided eye (blinded to Raman image), according to an illustrative embodiment. There is a residual rim of Raman signal in the resection bed around the resected tumor. Histological evaluation confirmed tumor in the locations of the Raman signal.
Figure 7:
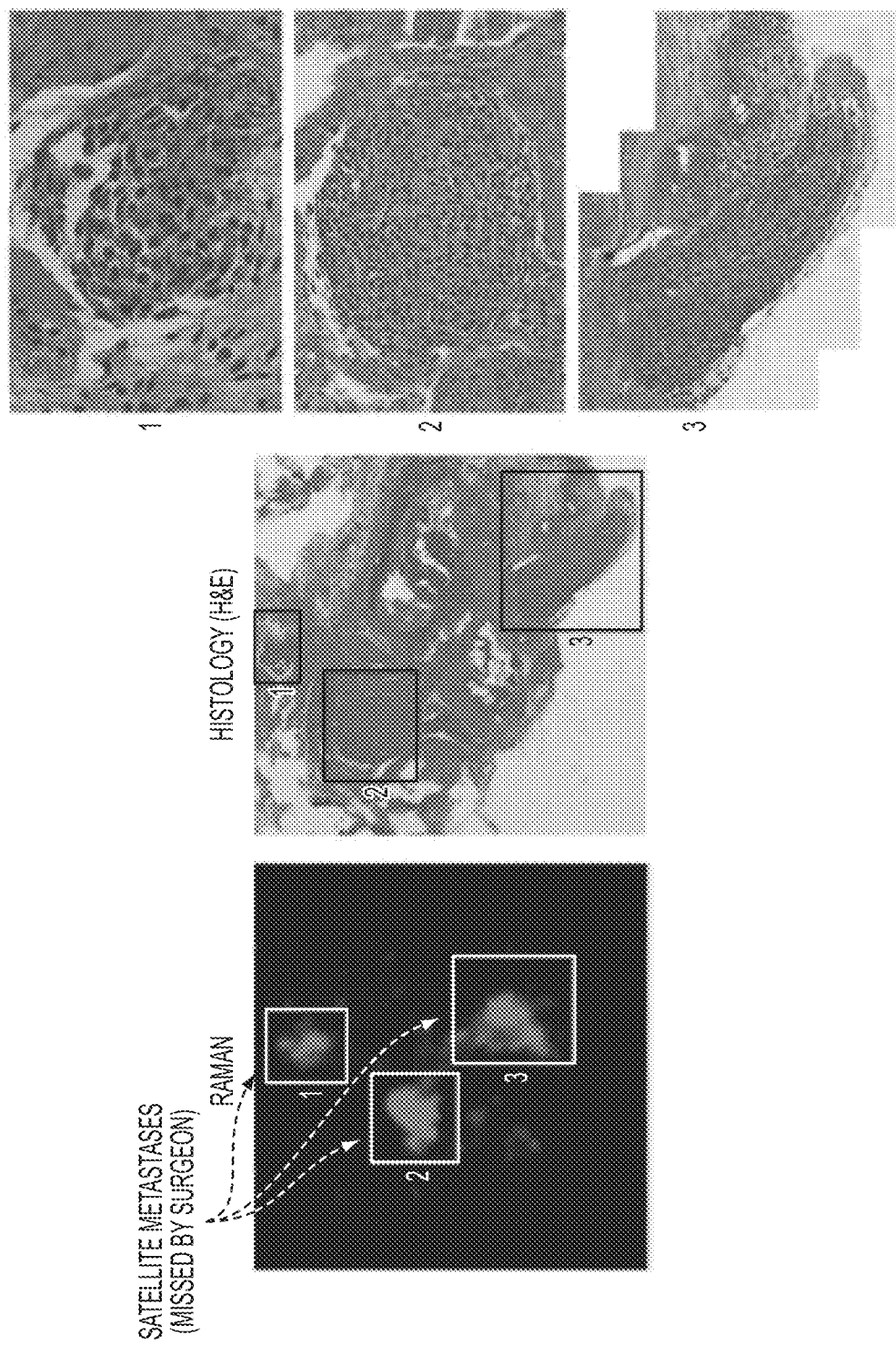
FIG. 7 shows how R-MR nanoparticles can be used to detect microscopic regional satellite metastases in a mouse with liposarcoma, according to an illustrative embodiment.
Figure 8:
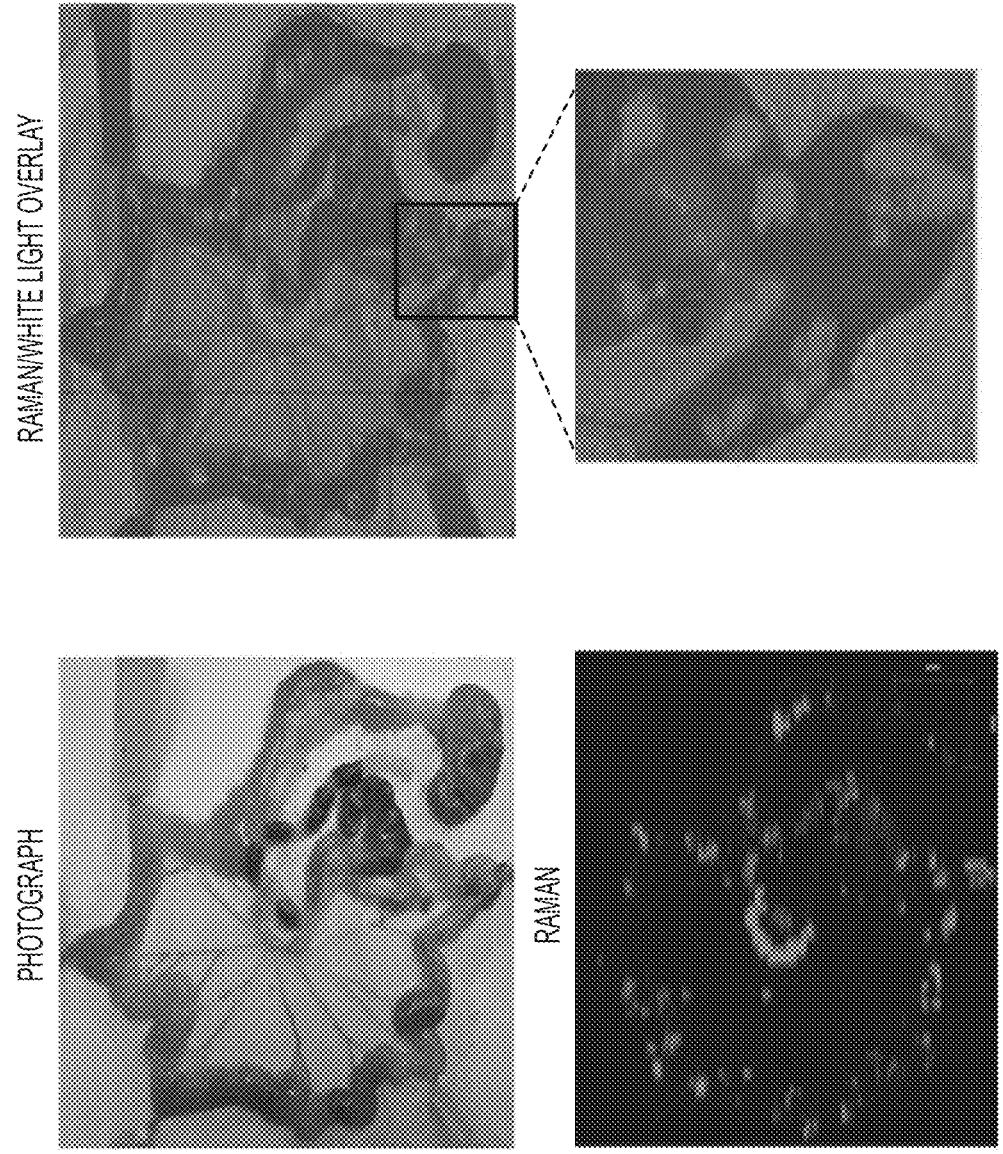
FIG. 8 shows how R-MR nanoparticles can be used to detect submillimeter-sized dysplastic (premalignant) polyps and adenocarcinomas, according to an illustrative embodiment. The experiment was performed in an APCmin mouse, which is a mouse model mimicking the human "adenomatosis polyposis coli" syndrome, a genetic disorder that causes many dysplastic polyps and adenocarcinomas to develop simultaneously. Note that Raman imaging reveals many small foci (less than 1 mm in size) of R-MR nanoparticle uptake within the colon and small bowel of an APCmin mouse (excised 24 hours after nanoparticle injection). These foci were then processed with histology, which demonstrated that they represented dysplastic polyps or adenocarcinomas.
Figure 9:
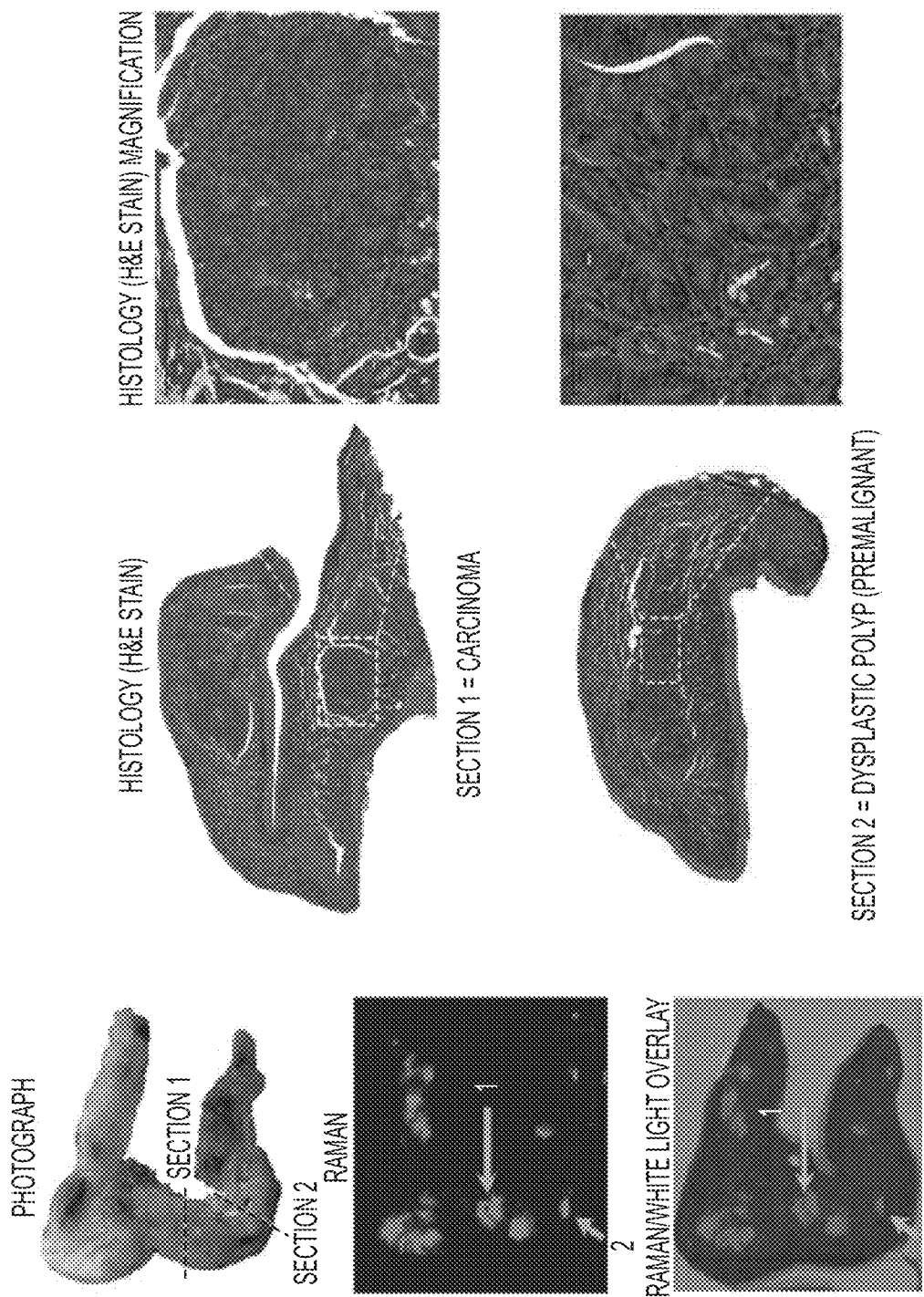
FIG. 9 shows how R-MR nanoparticles can be used to detect submillimeter-sized dysplastic (premalignant) polyps and adenocarcinomas, according to an illustrative embodiment—histological confirmation. Shown is a segment of colon from the mouse in FIG. 8. Two histological cross-sections through the Raman positive areas were obtained and stained with Hematoxylin-Eosin (H&E). Section 1 proved the lesion to represent an adenocarcinoma, section 2 a dysplastic polyp. This demonstrates that the R-MR nanoparticles are able to detect not only very small colon cancers, but also their premalignant form—dysplastic polyps—which will eventually develop into invasive adenocarcinomas. The R-MRs may therefore be used as a new method for early colon cancer detection.
Figure 10:
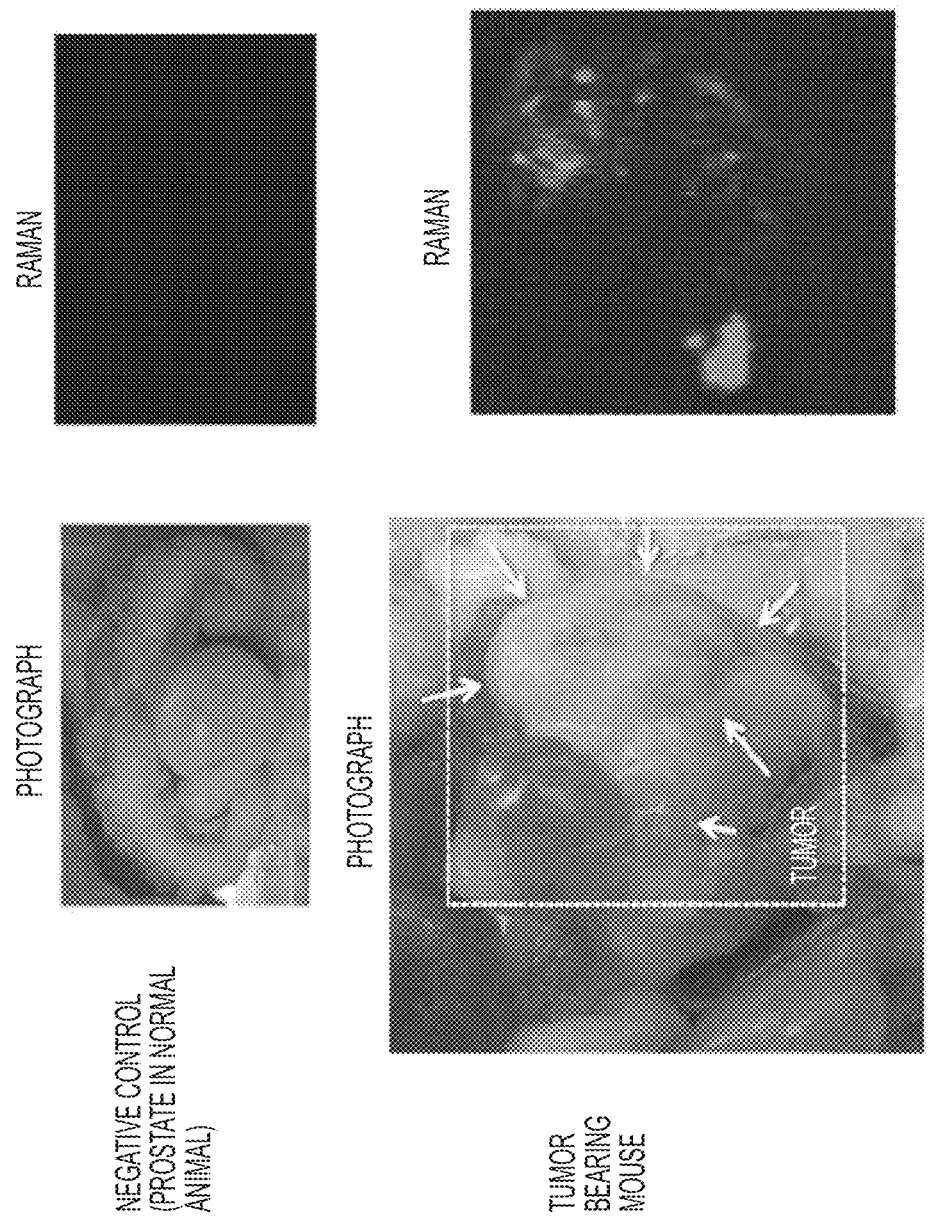
FIG. 10 shows how R-MR nanoparticles can be used to detect prostate cancer, according to an illustrative embodiment. Experiment was performed in a state-of-the-art genetic spontaneous (Hi-Myc) mouse model of prostate cancer. Mice express human c-Myc in the mouse prostate. Upper row: Images show a control animal (same mouse strain but without the Myc mutation) that was injected with R-MR-Nanoparticles: No Raman signal is seen in this normal prostate. Lower row: Images from a prostate cancer bearing mouse (hi-Myc) with obvious deformity of the prostate due to tumor (photograph) that was injected with the same amount of R-MR-Nanoparticles. The Raman image shows accumulation of R-MR-Nanoparticle within the tumor areas.
Figure 11:
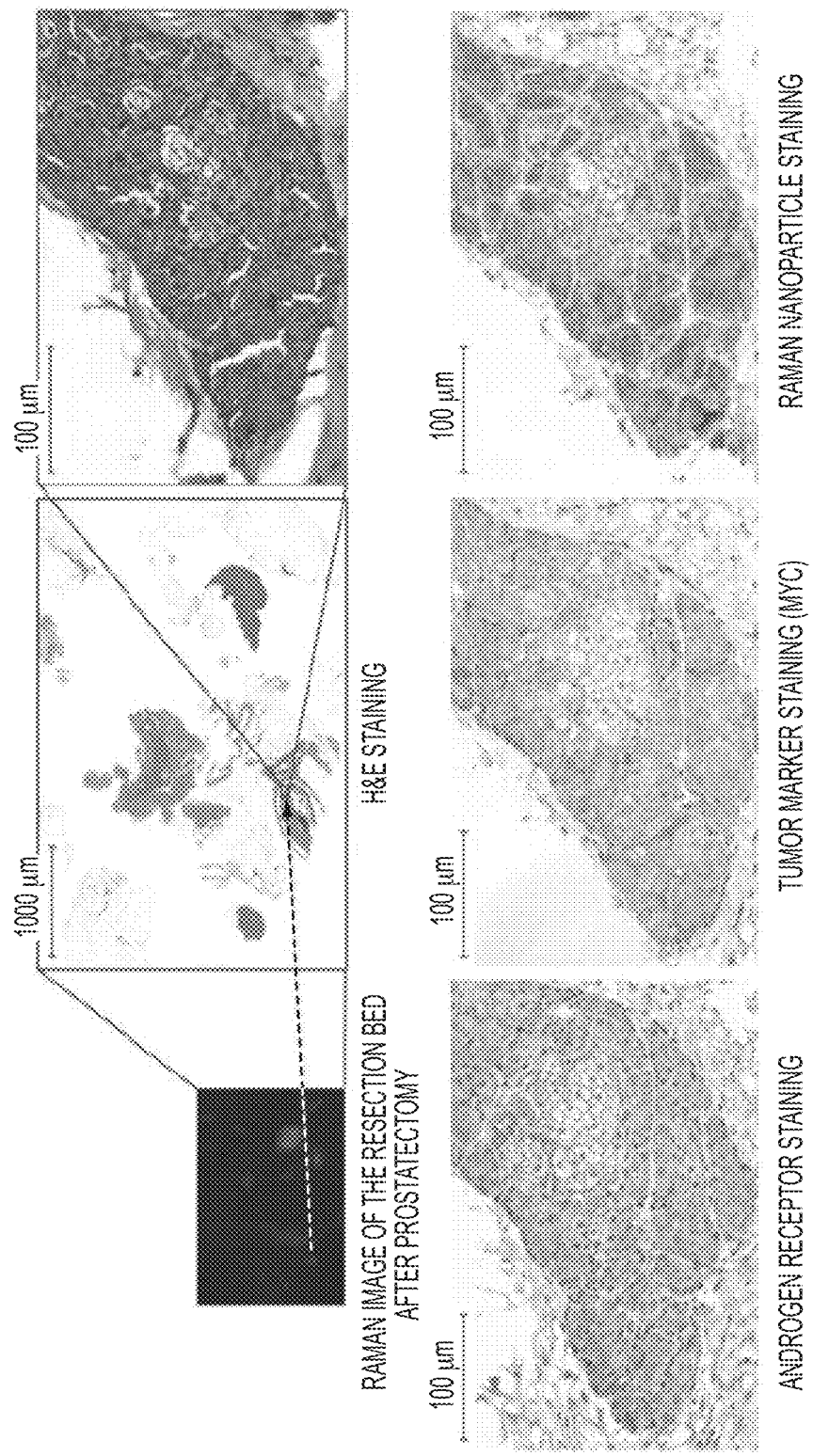
FIG. 11 shows how R-MR nanoparticles can be used to detect microscopic residual tumor in resection bed in a transgenic mouse model of prostate cancer (Hi-Myc), according to an illustrative embodiment. A prostatectomy was performed in a tumor-bearing Hi-Myc mouse, and subsequently the resection bed scanned with Raman imaging.

Surface-enhanced Raman scattering (SERS) represents a way to amplify the Raman signal many orders of magnitude. A Raman (SERS)-MRI nanoparticle that allows pre- and intraoperative brain tumor imaging has been described (Kircher et al., Nature Medicine, 18:829-835 (2012)), representing the first report of imaging a disease with a Raman nanoparticle. More recently, as described herein, a new generation of Raman-MRI nanoparticles, termed here "R-MR" nanoparticle has been developed that is characterized by: 1) vastly improved Raman signal amplification, which is about 50-fold (or more) higher than that reported for the original published SERS-MRI nanoparticle (FIG. 2), resulting in a detection threshold of only 1.8×10-15 molar (1.8 femtomolar, fM); and 2) use of an FDA-approved superparamagnetic iron oxide (Feraheme) in the R-MR nanoparticle core. Not only does this eliminate potential concerns regarding toxicity of Gadolinium (Gd3+) used in many prior Raman nanoparticles, it also increases the sensitivity for MRI detection. In many embodiments, R-MR nanoparticles are formed from inert materials (FDA approved core, gold shell, and a silica coating) and include a Raman active reporter embedded within the silica coating. The signal of such a reporter is massively amplified by the gold shell via the so-called localized surface plasmon resonance effect. R-MRs exhibit a pharmacokinetic behavior that is fundamentally different from conventional fluorescent dyes or currently clinically used MRI contrast agents (e.g. Magnevist®). Fluorescent dyes and clinical MRI agents wash out of tumors rapidly (within minutes) after i.v. injection. The tumor contrast is therefore only transient. In contrast, R-MRs do not wash out of the tumor, but are retained stably within the tumor cells, typically with a retention time at least 7 days. Without wishing to be bound by any particular theory, we propose that this behavior of R-MRs may be due, at least in part, to the so-called "enhanced permeability and retention (EPR)" effect, a phenomenon observed in all tumor types. This EPR effect means that particles of a certain size and surface charge enter tumors due to their leaky vasculature and are retained mostly via phagocytosis by tumor cells and tumor-associated macrophages. Up until recently nanoparticles were not able to visualize the EPR effect, because the trapped particle concentration is low, requiring very sensitive detection methods.

In some embodiments, the apparatus and methods described herein encompass the insight that development of a wide-field scanner would provide a variety of new and valuable uses for various types of Raman nanoparticles, including SERS, SERRS, SERS-MRI, R-MR and other nanoparticles. In some embodiments, a wide-field scanner is provided that permits imaging of nanoparticles over an entire operative bed in real time.

Previous Raman imaging systems include so-called Raman microscopes (e.g. InVia, Renishaw, Hoffman Estates, Ill.), which can only image in vitro samples or small animals up to the size of mice. They are large benchtop instruments that cannot be used in the operating room and require an imaging time of approx. 15 minutes to image a small field-of-view of 1 cm2. Hand-held Raman spectrometers (e.g. MiniRamIII®; B&WTek, Inc. Newark, Del.) are commercially available, however these do not acquire images, but only individual Raman spectra from one point in space. The present invention appreciates that neither of these two systems is suitable for rapid wide-field imaging in the operating room.

Nanoparticles which have a unique Raman spectrum consisting of several narrow peaks can be imaged without acquiring a full Raman spectrum; acquisition of the wavelengths located at the peaks is sufficient. Only 3-5 wavelengths (instead of >1000 for full spectral acquisition) need be acquired. The use of such nanoparticles together with hyperspectral detection technology, which generates a series of monochromatic images at user-specified wavelengths, can achieve instantaneous images across the full field of view. The hyperspectral system can detect spectra of a field of view of up to 1.5 $m^2$ at a spatial resolution of 1 $mm^2$ instantly. Because the above-described nanoparticles have unique Raman spectra with several very narrow peaks, it is not necessary to acquire the full Raman spectra, but sufficient to only acquire the wavelengths located at the peaks. An optical pathway can also be provided to acquire images that are "in focus" independent of the distance of the object from the detector, which may be important for imaging in the operating room, e.g., to account for an uneven operating bed, patient motion, and the like. The present Example describes development of a dedicated Raman imaging system with a field of view of 40×30 cm (sufficient for essentially all intraoperative scenarios) and a form factor that is optimized for the operating room.

In conjunction with certain nanoparticles as described herein, in some embodiments, this system enables ultrasensitive and -specific, real-time image guided cancer detection and resection.

The wide field Raman imaging apparatus described herein provides a variety of particular advantages, including speed, a wide field of view, specificity, depth independence, and multiplexing capabilities. Use of the hyperspectral acquisition technique allows spectra to be obtained substantially instantaneously (i.e., within milliseconds), and allows acquisition of a plurality of spectra at the same time, in contrast to raster- or line-scanning methods that result in very long image acquisition times. The apparatus is based on Raman spectroscopy and therefore detects specific Raman "fingerprints", in contrast to currently available wide-field imaging systems based on fluorescence, which may suffer from nonspecific background and autofluorescence that leads to "false-positives" (e.g., confusion of healthy tissue with cancerous tissue). The apparatus uses an optical pathway design that acquires images "in focus" independent of the distance of the object from the detector. This feature provides particular advantages for imaging of uneven fields of view expected to be encountered in the operating room. The apparatus and methods also enable differentiation of specific kinds of Raman nanoparticles, i.e., Raman nanoparticles that differ in their Raman reporter. This allows simultaneous imaging of many (10 or more) nanoparticles (e.g., co-injected nanoparticles targeted against different cancer epitopes, or nanoparticles injected via different routes [e.g., intravenously, intraarterially, intratumorally, intranodal, into lymphatic vessels etc.]). This feature allows imaging of multiple parameters at the same time, in contrast to fluorescence imaging, which typically can only differentiate up to 3 different fluorochromes with certainty.

Features of provided apparatus and methods enable imaging of large field of views (e.g., of up to 1.5 m$^2$) in less than a second, and furthermore enable simultaneous imaging of multiple particles, even on uneven fields. In some embodiments, a real-time (or near real-time) series of Raman-based images are obtained over a wide field.

Use of the provided wide-filed Raman scanner together with nanoparticle reporters, and particularly with the R-MR nanoparticles as described herein provides a variety of advantages including, for example, ultra-high sensitivity, reduced (or eliminated) autofluorescence, improved speed (lower acquisition times), improved versatility, photostability, unique pharmacokinetics, inertness, and scaleability.

In some embodiments, R-MR nanoparticles are used in apparatus, systems, and/or methods described herein. R-MR nanoparticle reporters have a Raman detection threshold of 1.8 fM (1.8×10-15 M), an extremely high sensitivity. This sensitivity approaches in vitro detection assays such as PCR. This sensitivity permits definition of tumor outlines without the need for a targeting moiety, exploiting the so-called "enhanced permeability and retention (EPR)" effect that all tumors exhibit. In contrast, the sensitivity of fluorescence imaging is only 10-9-10-12 M which is significantly less sensitive than the R-MR nanoparticles described herein, and would not allow imaging of nanoparticle EPR effects.

Furthermore, autofluorescence is common to all imaging methods based on fluorescence. Autofluorescence can cause an imaging system to mistakenly identify healthy for cancerous tissue. In contrast, Raman spectroscopy is based on a principle fundamentally different from fluorescence, and issues associated with autofluorescence are not observed.

Regarding image acquisition speed, the high Raman signal amplification via the SERRS effect allows ultra-short acquisition times, as described herein. As the EPR effect is observed in all tumor types, R-MRs work in a wide variety of different tumor types, even without any associated targeting moiety. In contrast, a targeted nanoparticle would have to be designed and FDA-approved for each target (tumor) separately.

R-MRs require no targeting moiety (such as an antibody, affibody, peptide, etc.) on their surface. Non-targeted embodiments permit easier and less expensive production. R-MRs, in contrast to organic fluorochromes, do not photobleach. A problem with many imaging technologies is that photobleaching prevents imaging in contexts that involve or require prolonged laser exposure (e.g., as would be expected during a lengthy surgical procedure). Use of Raman reporters, such as the R-MR nanoparticles, that do not photobleach, have the additional advantage that they can be useful in such contexts that involve or require prolonged laser exposure.

The contrast kinetics of R-MRs (stable retention within tumor cells) allows repeated pre- and intraoperative MRI and Raman scanning, for example, using just a single injection. Alternative imaging technologies, for example, those utilizing fluorochrome and clinical MRI agents, wash rapidly out of tissues, therefore typically requiring repeated rejections. Additionally, such technologies often cause issues with false positive contrast due to leaking into the resection bed. Embodiments of provided Raman technologies avoid these identified problems.

R-MRs are based on an RDA-approved core. Gold and silica are inert materials, and nanoparticles made of these materials have been shown to be nontoxic in cell cultures, mice, and in several clinical trials. Furthermore, facile and rapid synthesis of R-MRs allows for their large scale production.

In some embodiments, apparatus and methods described herein are used in conjunction with Raman-based ablation and resection systems described herein.

In some embodiments, Raman reporters are used in apparatus, systems, and/or methods described herein as an ablating source for tumor or tissues. Raman reporters represent a way to amplify the Raman signal many orders of magnitude. The amplification, when employed at sufficient energy levels, elevates the vibration modes of the Raman reporter (e.g., SERS, SERRS, SERS-MRI, R-MR and other nanoparticles) to a level to cause damage to or heating of nearby tissue or tumor in the vicinity of a given Raman reporter. In some instances, the vibrational mode can cause vaporization of the Raman reporter and the nearby tissue.

The present disclosure encompasses methods, systems, and devices for assessing and/or treating (e.g., ablating and/or resecting) cells and/or tissue in a subject. In particular, the methods and devices described herein provide for detection of Raman spectra from cells and/or tissues and subsequent targeted ablation and/or resection of cells and/or tissues from which Raman spectra are detected. In some embodiments, systems and devices of the disclosure further include components to visually image target cells and/or tissues. In some embodiments, methods, systems and devices of the disclosure do not need or include components to visually image target cells and/or tissues.

In some embodiments, the disclosure encompasses an automated surgical tissue resection instrument and/or an automated laser ablation instrument that resects and/or ablates only disease tissue at locations at which a Raman reporter is detected, e.g., by comparing detected Raman signal to specific Raman signals/spectra associated with one or more type of Raman nanoparticle or intrinsic species known to be associated with the presence of tissue to be resected or ablated. Such an instrument resects and/or ablates only diseased tissue, because a motorized resection mechanism and/or ablation laser included in the instrument is activated only when the specific spectrum of a Raman reporter is recognized by a Raman spectrometer included in the system. If a specific Raman signal is not detected at a given location (indicating healthy tissue), the instrument automatically stops (or does not start) resecting and/or ablating at that location. In some embodiments, a Raman reporter is a Raman nanoparticle, which can optionally can be designed to target and/or accumulate within or proximate to diseased tissue of interest (e.g., cancer, infection, or inflammation).

FIG. 25 depicts a flowchart of an exemplary method of the disclosure. Starting at the lower left box, a diseased tissue (e.g., a tumor) containing a Raman reporter (e.g., a Raman nanoparticle described herein or an intrinsic Raman species) is provided. In some embodiments, a Raman nanoparticle is administered to a subject, and the nanoparticle accumulates within diseased tissue. Using a Raman laser, a Raman reporter present within the diseased tissue is excited, which emits Raman scattered photons. In this exemplary method, Raman scattered photons are filtered using a 785 nm bandpass filter and are spectrally separated using a prism. Raman scattered photons are detected using a detector, e.g., a CCD detector. Detected Raman scattered photons are then analyzed using an analyzer (e.g., a computer with Raman analysis software) to determine if a Raman reporter is present. If a Raman reporter is present, the analyzer activates a resector/ablation mechanism (e.g., a mechanical resector (e.g., rotary blade, vibrating knife, or percussing knife), an electro-cautery mechanism, a cryoablation mechanism, and/or a radiofrequency ablation mechanism), which destroys diseased tissue. If the analyzer determines that no Raman reporter is present, the analyzer does not activate (or, if previously activated, shuts off) the resector mechanism, preserving healthy tissue. In some embodiments, a Raman reporter is initially detected, and the steps of excitation, detection, and analysis are repeated until a Raman reporter is not detected.

In some embodiments, systems and devices of the disclosure enable more precise resection and/or ablation of diseased tissue. Surgeons often resect diseased tissue by visual inspection, which may be imprecise at the margins of diseased and non-diseased tissue, for example, at margins of infiltratively growing cancers or in the setting of metastic spread. In some embodiments, a Raman reporter is a Raman nanoparticle, which specifically targets diseased tissue (e.g., cancer), methods, systems, and devices of the disclosure can allow a surgeon to resect and/or ablate diseased tissue (e.g., cancer) faster and with much higher precision, e.g., compared to visual inspection or other known methods. In some embodiments, a Raman reporter is an intrinsic species within, on, or near diseased tissue, and a predetermined intrinsic Raman spectrum is used in the methods described herein. In some embodiments, resection and/or ablation is performed in a semiautomated fashion, e.g., a device described herein is held approximately at or moved generally over a site of disease and automatically removes only diseased tissue but not adjacent healthy tissue. The methods, systems, and devices described herein have many applications, e.g., open surgical applications, endoscopic approaches, and robotically assisted approaches.

In Vitro and In Vivo Data

Both in vitro and in vivo data demonstrate the R-MRs' ability to outline multiple different tumor types. This includes outlining the bulk tumor, residual tumor in the resection bed that was "missed" by the surgeon, satellite metastases, and even individual tumor cells. (See Figures). Raman images shown in these Figures were acquired with a Renishaw InVia Raman microscope, which allows acquisition of areas up to approx. 3×3 cm, cannot image animals larger than mice, and necessitates imaging times of 15 to 60 min/image. While the data demonstrate the feasibility of the R-MR nanoparticle approach, it also illustrates the need for the high-speed wide field Raman imaging apparatus described herein to translate this approach into humans.

Raman Spectroscopy

Raman spectroscopy provides information about the vibrational state of molecules. Many molecules have atomic bonds capable of existing in a number of vibrational states. Such a molecule is able to absorb incident radiation that matches a transition between two of its allowed vibrational states and to subsequently emit the radiation. These vibrational transitions exhibit characteristic energies that permit definition and characterization of the bonds that are present in a compound. Analysis of vibrational transitions therefore permits spectroscopic molecular identification.

Most often, absorbed radiation is re-radiated at the same wavelength, a process designated Rayleigh or elastic scattering. In some instances, the re-radiated radiation can contain slightly more or slightly less energy than the absorbed radiation (depending on the allowable vibrational states and the initial and final vibrational states of the molecule). The energy difference is consumed by a transition between allowable vibrational states, and these vibrational transitions exhibit characteristic values for particular chemical bonds, which accounts for the specificity of vibrational spectroscopies such as Raman spectroscopy.

The result of the energy difference between the incident and re-radiated radiation is manifested as a shift in the wavelength between the incident and re-radiated radiation, and the degree of difference is designated the Raman shift (RS), measured in units of wavenumber (inverse length). If the incident light is substantially monochromatic (single wavelength) as it is when using a laser source, the scattered light that differs in frequency can be more easily distinguished from Rayleigh scattered light.

Raman spectroscopy may utilize high efficiency solid-state lasers, efficient laser rejection filters, and silicon CCD detectors. In general, the wavelength and bandwidth of light used to illuminate a sample is not critical, so long as the other optical elements of the system operate in the same spectral range as the light source.

In general, a sample should be irradiated with monochromatic light (e.g., substantially monochromatic light). Suitable light sources include various lasers and polychromatic light source-monochromator combinations. It is recognized that the bandwidth of the irradiating light, resolution of the wavelength resolving element(s), and the spectral range of a detector determine how well a spectral feature can be observed, detected, or distinguished from other spectral features. The combined properties of these elements (e.g., the light source, the filter, grating, or other mechanism used to distinguish Raman scattered light by wavelength) define the spectral resolution of the Raman signal detection system. The known relationships of these elements enable the skilled artisan to select appropriate components in readily calculable ways. Limitations in spectral resolution of the system (e.g., limitations relating to the bandwidth of irradiating light, grating groove density, slit width, interferometer stepping, and other factors) can limit the ability to resolve, detect, or distinguish spectral features. The separation and shape of Raman scattering signals can be used to determine the acceptable limits of spectral resolution for the system for any Raman spectral features.

Typically, a Raman peak that both is distinctive of a substance of interest (e.g., a Raman nanoparticle or intrinsic species described herein) and exhibits an acceptable signal-to-noise ratio can be selected. Multiple Raman shift values characteristic of the substance (e.g., Raman nanoparticle or intrinsic species) can be assessed, as can the shape of a Raman spectral region that may include multiple Raman peaks.

Raman Nanoparticles

In some embodiments, methods of the disclosure include use of Raman nanoparticles, e.g., surface-enhanced Raman scattering (SERS) nanoparticles or surface-enhanced (resonance) Raman scattering (SERRS) nanoparticles. SERS and SERRS refer to an increase in Raman scattering exhibited by certain molecules in proximity to certain metal surfaces (see, U.S. Pat. No. 5,567,628; McNay et al., Applied Spectroscopy 65:825-837 (2011)). The SERS effect can be enhanced through combination with a resonance Raman effect. The SERS effect can be increased by selecting a frequency for an excitation light that is in resonance with a major absorption band of a molecule being illuminated. In short, a significant increase in the intensity of Raman light scattering can be observed when molecules are brought into close proximity to (but not necessarily in contact with) certain metal surfaces. Metal surfaces can be roughened or coated with minute metal particles. The increase in intensity can be on the order of several million-fold or more.

Nanoparticles that can be detected using Raman spectroscopy can be used in the methods and devices described herein. Raman nanoparticles and SERS nanoparticles and methods of their production are known and described in, e.g., U.S. Publ. No. 2012/0179029; Kircher et al., Nature Med. 18:829-834 (2012); Yigit et al., Am. J. Nucl. Med. Mol. Imaging 2:232-241 (2012); Zhang et al., Small. 7:3261-9 (2011); Zhang et al., Curr. Pharm. Biotechnol. 11:654-661 (2010).

In some embodiments, Raman nanoparticles (e.g., SERS nanoparticles) are administered to a subject having or suspected of having cancer. Without being bound to theory, it is believed that such nanoparticles target to and/or accumulate within, on the surface of, or proximate to cancer cells by enhanced permeability and retention (EPR) as described in, e.g., Kircher et al., Nature Med. 18:829-834 (2012), and Adiseshaiah et al., Wiley Interdiscip. Rev. Nanomed. Nanobiotechnol. 2:99-112 (2010). Thus, detection of Raman nanoparticles indicates such cells and/or tissues are cancerous.

In some embodiments, the Raman nanoparticles are employed for ablation of the nearby cell tissue or tumor. Energy absorbed at selected frequencies of an excitation light that is in resonance with a major absorption band of a molecule being illuminated causes vibrational mode of the Raman nanoparticle that can cause ablation of the nearby cell tissue or tumor. In certain embodiments, the ablation causes damage to the cell and, in certain embodiments, the ablation causes heating or vaporization of the area situated near the nanoparticle. In some embodiments, the wavelength and bandwidth of light are selected to minimize a mismatch between the depth of measurement employed for the spectroscopic imaging and the depth to which the tissue or tumor is ablated.

In some embodiments, Raman reporter detection is combined with one or more additional modalities for identification of tissue to be resected or ablated. For example, Raman reporter detection can be combined with video imaging, MRI, NMR, PET, SPECT, CT, X-ray, ultrasound, photoacoustic detection, and/or fluorescent detection, for example. Also, Raman nanoparticles may be designed such that they are detected by reporter detection combined with one or more other modalities, such as video imaging, MRI, NMR, PET, SPECT, CT, X-ray, ultrasound, photoacoustic detection, and/or fluorescent detection, for example. Such nanoparticles are described in, e.g., Kircher et al., Nature Med. 18:829-834 (2012); PCT/US 13/57636 and PCT/US13/76475.

Nanoparticles used in accordance with the present disclosure, in theory, can be of any shape (regular or irregular) or design. In some embodiments, a nanoparticle can be or comprise a sphere. Additionally or alternatively, a nanoparticle can be or comprises a star, a rod, a cube, a cuboid, a cone, a pyramid, a cylinder, a prism, a tube, a ring, a tetrahedron, a hexagon, an octagon, a cage, or any irregular shapes. In some embodiments, a nanoparticle has a shape corresponding to that of its substrate; in some embodiments, a nanoparticle has a shape different from that of its substrate. In some embodiments, where the nanoparticle and substrate have different shapes, one or more layers applied to the substrate has a thickness that varies at different locations within the nanoparticle In some embodiments, the greatest dimension or at least one dimension of a nanoparticle may be about or less than 10 µm, 5 µm, 1 µm, 800 nm, 500 nm, 400 nm, 300 nm, 200 nm, 180 nm, 150 nm, 120 nm, 110 nm, 100 nm, 90 nm, 80 nm, 70 nm, 60 nm, 50 nm, 40 nm, 30 nm, 20 nm, 10 nm, 5 nm, 2 nm, or even 1 nm. In some embodiments, the greatest dimension or at least one dimension of a nanoparticle may be more than 10 µm, 5 µm, 1 µm, 800 nm, 500 nm, 400 nm, 300 nm, 200 nm, 180 nm, 150 nm, 120 nm, 110 nm, 100 nm, 90 nm, 80 nm, 70 nm, 60 nm, 50 nm, 40 nm, 30 nm, 20 nm, 10 nm, 5 nm, 2 nm, or even 1 nm. In some embodiments, the greatest dimension or at least one dimension of a nanoparticle may be in a range of about 1 µm to about 5 nm or about 200 nm to about 5 nm. In some embodiments, the greatest dimension or at least one dimension of a nanoparticle may be in a range of about 300 nm to about 50 nm. In some embodiments, the greatest dimension or at least one dimension of a nanoparticle may be in a range of about 130 nm to about 90 nm. In some embodiments, the greatest dimension or at least one dimension of a nanoparticle may be in a range of any two values above. In some embodiments, the dimension of a nanoparticle is a diameter, wherein the diameter can be in a range as mentioned above. In some embodiments, the dimensions of a nanoparticle can be represented by a length, a width or a height in X, Y and Z axis, wherein each dimension can be in a range as mentioned above.

It will be appreciated by those skilled in the art that particular sizes and/or shapes may be especially desirable or useful in different contexts. For example, nanoparticles for in vivo application typically have a size range from about 0.5 nm to about 200 nm; nanoparticles for in vitro application can have a size range from about 10 nm to about 1000 nm.

In some embodiments, nanoparticle sizes and surface charges are tuned to be provided to sites of interest for certain applications. In many embodiments, a site of interest is a tumor. In some embodiments, nanoparticles are designed and constructed to enter tumors via their leaky vasculature. In some embodiments, nanoparticles are designed and constructed to enter and/or be retained in tumors via phagocytosis by tumor (associated) cells (known as "enhanced permeability and retention (EPR)" effect). In certain embodiments, nanoparticles do not wash out of a tumor, but are retained stably within the tumor (e.g., retention time at least 7 days).

In various embodiments, a nanoparticle described herein can comprise a substrate, a plurality of layers (including one or more condensation layers; in some embodiments at least two condensation layers), and one or more dopant entities (in some embodiments at least two dopant entities). In some embodiments, nanoparticles are susceptible to imaging by multiple modalities.

In certain embodiments, a substrate comprises iron oxide for T2 MRI and/or gold substrate for photoacoustics, CT, and X-Rays. In certain embodiments, a plurality of layers are or comprise silica. In certain embodiments, the closest layer to a substrate comprises a surface-enhanced resonance Raman scattering (SE(R)RS)-active agent. In certain embodiments, such a nanoparticle further comprises an outer layer doped with a NIR fluorescent agent. In certain embodiments, there is a buffer layer between the two layers. In certain embodiments, provided nanoparticles can be employed with other agents such as MRI, PET, SPECT, CT, X-Rays or US agents.

Substrate

In accordance with the present invention, a nanoparticle has at least one substrate, which can be or comprise one or more materials, for example depending on applications for which the nanoparticle will be utilized. Exemplary substrate materials include, but are not limited to, metals, non-metals, and semi-metals, or oxides thereof (i.e., metal oxides, non-metal oxides, or semi-metal oxides) (e.g., iron oxide), liposomes, upconverting materials, semiconductors, and combinations thereof. Any materials used in a layer described below can be used as materials of a substrate. In some embodiments, a layer can be a nanoparticle's substrate. In some embodiments, photoacoustic and/or photothermal enhancements can be achieved by associating agents/molecules which induce surface phonon enhancement, within the substrate or layers.

In some embodiments, a substrate can be or contain any metal or any other material capable of generating localized surface plasmon resonances (LSPRs). In many embodiments, a metal is a SE(R)RS active metal. Such a metal can be any (metallic) substance capable of sustaining a (localized) surface plasmon resonance. In some embodiments, a SE(R)RS active metal is or comprises Au, Ag, Cu, Na, K, Cr, Al, or Li. A substrate can also contain alloys of metals. In some embodiments, a substrate is or contains Au, Ag or a combination thereof. In certain embodiments, a substrate can provide a detectable photoacoustic signal.

A substrate can be of any shape or design, and may contain one or more structural elements. In some embodiments, a nanoscale or at least one structural element of it is spherical. In some embodiments, a substrate or at least one structural element of it is non-spherical. In some embodiments, a substrate has structural elements selected from the group consisting of spheres, rods, stars, shells, ellipses, triangles, cubes, cages, pyramids and combinations thereof. For example, a substrate can consist of or comprise a star overlaid with at least one shell. To give another example, a substrate can consist of or comprise two or more concentric shells. In some particular embodiments, a substrate can consist of or comprise a central structure surrounded by satellite structures.

In some embodiments, a substrate comprises at least two structural elements, separated from one another within a distance suitable for a plasmon hybridization effect. A distance can be an average distance. In certain embodiments, a distance between two separated structural elements is less than 100 nm, 50 nm, 30 nm, 20 nm, 15 nm, 10 nm, 8 nm, 5 nm or 3 nm, or 1 nm. In certain embodiments, a distance between two separated structural elements is in a range of about 100 nm to about 50 nm, about 50 nm to about 30 nm, about 30 nm to about 1 nm, or any two values above. In certain embodiments, individual structural elements are separated from one another or filled by a layer.

In some embodiments, a substrate is star-shaped. As used herein, the term "star shaped" refers to a body portion from which a plurality of protrusions extend. In some embodiments, a star shape is a true star shape. A "true star shape", as that term is used herein, comprises a body portion from which a plurality of protrusions extend radially. In some embodiments, a true star shape has at least one access of symmetry. In some embodiments, a true star shape is substantially symmetrical. In some embodiments, protrusions in a true star shape have approximately the same length. In some embodiments, protrusions have approximately the same width. In some embodiments, protrusions have substantially identical structures. In some embodiments, a true star shape has a body portion that is substantially spherical.

In some embodiments, a true star shape has a body portion that is substantially rectangular or square. In some embodiments, protrusions substantially cover the body surface. In some embodiments, protrusions are configured on the body surface for high polarizabilities, for example so that intense localized surface plasmons can arise. It is contemplated that when a particle contains radially-protruding spikes, the coordinated electron oscillation becomes corralled into narrow regions (i.e., the tips) resulting in the build-up of charge in a very small region. Thus, a certain number of spikes results in an electromagnetic enhancement over a geometry which does not contain any. Substrates with an excess of spikes or asymmetric features, on the other hand, have smaller polarizabilities and cannot sustain large surface plasmon resonances because they encounter strong damping from the significant increase in electron-electron collisions, making coordinated oscillations of electrons weak and short-lived.

In some embodiments, the greatest dimension or at least one dimension of a substrate or its each component may be about or less than 5 µm, 1 µm, 800 nm, 500 nm, 400 nm, 300 nm, 200 nm, 100 nm, 90 nm, 80 nm, 70 nm, 60 nm, 50 nm, 40 nm, 30 nm, 20 nm, 15 nm, 10 nm, 5 nm, 2 nm, 1 nm or 0.5 nm. In some embodiments, the greatest dimension or at least one dimension of a substrate or its each component may be more than 5 µm, 1 µm, 800 nm, 500 nm, 400 nm, 300 nm, 200 nm, 100 nm, 90 nm, 80 nm, 70 nm, 60 nm, 50 nm, 40 nm, 30 nm, 20 nm, 15 nm, 10 nm, 5 nm, 2 nm, 1 nm or 0.5 nm. In some embodiments, the greatest dimension or at least one dimension of a substrate or its each component may be in a range of about 500 nm to about 5 nm or about 150 nm to about 5 nm. In some embodiments, the greatest dimension or at least one dimension of a substrate or its each component may be in a range of about 100 nm to about 90 nm, about 90 nm to about 80 nm, about 80 nm to about 70 nm, about 70 nm to about 60 nm, about 60 nm to about 50 nm, about 50 nm to about 40 nm, about 40 nm to about 30 nm, about 30 nm to about 20 nm, about 20 nm to about 10 nm, about 10 nm to about 5 nm. In some embodiments, the greatest dimension or at least one dimension of a substrate or its each component may be in a range of any two values above.

A substrate with a desired size can be grown as metal colloids by a number of techniques well known in the art. For example, chemical or photochemical reduction of metal ions in solution using any number of reducing agents has been described. Likewise, syntheses of substrates can be carried out in constrained volumes, e.g., inside a vesicle. Substrates can also be made via electrical discharge in solution. Substrates can also be made by irradiating a metal with a high intensity pulsed laser.

Layers

Nanoparticles provided by the present disclosure may include a plurality of layers. In some embodiments, one or more inner layers can construct a nanoparticle's substrate.

In some embodiments, a layer substantially covers at least one surface of the substrate (or of another layer that itself substantially covers at least one surface of the substrate or of another layer). In some such embodiments, a layer substantially encapsulates the substrate.

In some embodiments, adjacent layers are in direct physical contact with one another; in some embodiments, adjacent layers are separated from one another so that an inter-layer space is defined; in some embodiments, such an inter-layer space is empty; in some embodiments, such an inter-layer contains liquid, etc.

A layer can have any size and shape. In some embodiments, a layer can be porous. In some embodiments, a layer is in a shape of a thin stripe or mat. In some embodiments, one or more layers substantially or partially cover the surface of a substrate or another layer.

In some embodiments, layers are arranged as shells. In some embodiments, at least two shells can be partially extended from at least one substrate, concentrically extended from at least one substrate, or extended asymmetrically from at least one substrate. Shells can have equal thicknesses, but can also have different thicknesses.

A plurality of layers each can respectively contain one or more materials. Layers (e.g., shells) can be or comprise, but are not limited to, one and the same material (e.g., consisting of, but not limited to, compounds/materials from the group of metal/semi-metal/non-metal, -oxides, -sulfides, -carbides, -nitrides), layers can consist of at least two different materials (e.g., from the groups of metal/semi-metal/non-metal, -oxides, -sulfides, -carbides, -nitrides, polymers, and combinations thereof), layers can consist of the same or different materials in any combination (e.g., consisting of, but not limited to, compounds/materials from the groups of metal/semi-metal/non-metal, -oxides, -sulfide, -carbides, -nitrides, ((bio-)degradable) polymers, (poly)peptides, nucleic acids (DNA), and combinations thereof) with at least one of them being porous.

In some embodiments, a layer is synthesized by reacting precursors and the resulting layer is a condensation layer. Nanoparticles described herein, in some embodiments, comprise at least a condensation layer and at least another layer, which can be another condensation layer or any other layers.

According to various embodiments of the present disclosure, a layer can be or comprise metal (e.g., gold, silver, and the like), semi-metal or non-metal, and metal/semi-metal/non-metal oxides including silica ($SiO_2$), titania ($TiO_2$), alumina ($Al_2O_3$), zirconia ($ZrO_2$), germania ($GeO_2$), tantalum pentoxide ($Ta_2O_5$), $NbO_2$, etc., and non-oxides including metal/semi-metal/non-metal borides, carbides, sulfide and nitrides, such as titanium and its combinations (Ti, $TiB_2$, TiC, TiN, etc.).

Additionally or alternatively, materials of a layer can be polymers including PEG and PLGA/PEG, and polymeric chelators (e.g., poly DOTA, dendrimer backbone, poly DTPA, or dendrimer alone), (multiwalled) carbon nanotubes, graphene, silicone, peptides, nucleic acids, and combinations thereof.

In some embodiments, a layer is or comprises a dielectric. For example, silica can serve as a dielectric.

In some embodiments, each layer in a nanoparticle can be or contain the same material(s). To give one particular example, multilayers in the nanoparticle are all silica layers.

In some embodiments, a layer is or includes silica. For example, a silica layer can be synthesized from a silica precursor including, but not limited to, alkylalkoxysilane; ethylpolysilicate; tetraethylorthosilicate (TEOS); tetramethylorthosilicate (TMOS); partially hydrolyzed TEOS; partially hydrolyzed TMOS or a combination thereof.

In some embodiments, the present invention provides technologies that permit control of layer thickness. For example, in many embodiments, condensation layer thickness is controlled by selection of solvent composition and/or content in the precursor solution. For example, in some embodiments, where a solvent composition comprising water is utilized, water content can control layer thickness. For example, in some embodiments, the well-known Stöber method can be adapted for use in preparing one or more silica layers in accordance with the present disclosure. Typically, the synthesis involves using a solution of one or more precursors in water and alcohol(s). A water content as used herein refers to the ratio of the volume of water to the total volume of a precursor solution.

In some embodiments, condensation reactions utilizing a water-containing solvent achieve different layer thicknesses with different water content. In some embodiments, a water content for synthesis is about 1.0 v/v/%, about 2.0 v/v %, about 3.0 v/v %, about 4.0 v/v %, about 4.5 v/v %, about 5.0 v/v %, about 5.5 v/v %, about 6.0 v/v %, about 6.5 v/v %, about 7.0 v/v %, about 7.5 v/v %, about 8.0 v/v %, about 8.5 v/v %, about 9.0 v/v %, about 9.5 v/v %, or about 10.0 v/v %. In some embodiments, water content for synthesis is in a range of any two values above.

In some embodiments, a layer is or includes one or more polymers, particularly polymers that which have been approved for use in humans by the U.S. Food and Drug Administration (FDA) under 21 C.F.R. § 177.2600, including, but not limited to, polyesters (e.g., polylactic acid, poly(lactic-co-glycolic acid), polycaprolactone, polyvalerolactone, poly(1,3-dioxan-2-one)); polyanhydrides (e.g., poly (sebacic anhydride)); polyethers (e.g., polyethylene glycol); polyurethanes; polymethacrylates; polyacrylates; polycyanoacrylates, copolymers of PEG and poly(ethylene oxide) (PEO).

In some embodiments, a layer is or includes at least a degradable material. Such a degradable material can be hydrolytically degradable, biodegradable, thermally degradable, enzymatically degradable, and/or photolytically degradable polyelectrolytes. In some embodiments, degradation may enable release of one or more dopant entities (e.g., agent for delivery) associated with a particle described herein.

Degradable polymers known in the art, include, for example, certain polyesters, polyanhydrides, polyorthoesters, polyphosphazenes, polyphosphoesters, certain polyhydroxyacids, polypropylfumerates, polycaprolactones, polyamides, poly(amino acids), polyacetals, polyethers, biodegradable polycyanoacrylates, biodegradable polyurethanes and polysaccharides. For example, specific biodegradable polymers that may be used include but are not limited to polylysine, poly(lactic acid) (PLA), poly(glycolic acid) (PGA), poly(caprolactone) (PCL), poly(lactide-co-glycolide) (PLG), poly(lactide-co-caprolactone) (PLC), and poly(glycolide-co-caprolactone) (PGC). Another exemplary degradable polymer is poly (beta-amino esters), which may be suitable for use in accordance with the present application.

In general, any layer within a particle described herein can have a thickness independently and within any ranges. In some embodiments, some or all layers have the same thickness or within the same range.

A layer on a substrate can have an average thickness in various ranges. In some embodiments, an averaged thickness is about or less than 5 μm, 1 μm, 800 nm, 500 nm, 400 nm, 300 nm, 200 nm, 100 nm, 90 nm, 80 nm, 70 nm, 60 nm, 50 nm, 40 nm, 30 nm, 20 nm, 15 nm, 10 nm, 5 nm, 1 nm, 0.5 nm, or 0.1 nm. In some embodiments, an averaged thickness is about or greater than 5 μm, 1 μm, 800 nm, 500 nm, 400 nm, 300 nm, 200 nm, 100 nm, 90 nm, 80 nm, 70 nm, 60 nm, 50 nm, 40 nm, 30 nm, 20 nm, 15 nm, 10 nm, 5 nm, 1 nm, 0.5 nm, or 0.1 nm. In some embodiments, an averaged thickness is in a range from about 0.1 nm to about 5 μm, about 0.5 nm to about 200 nm, about 5 nm to about 50 nm or about 10 to about 30 nm. In some embodiments, an averaged thickness is in a range of any two values above.

In some embodiments, a layer can have or be modified to have one or more functional groups. Such functional groups (within or on the surface of a layer) can be used for association with any agents (e.g., detectable entities, targeting entities, or PEG). Such associated agents can be dopant entities, if associated (e.g., doped) within layers. For example, targeting entities and/or PEG can be associated within one or more layers comprising degradable polymers. When the degradable polymers degrade, the dopant entities can be exposed.

In some embodiments, the surface of an outer-most layer can be modified with reagents to add and/or modify the functional groups on the outer layer (e.g., compounds like, but not limited to, mercaptosilanols, aminosilanols can be used to introduce sulfhydryl or amine groups, respectively, to silica, tantalia, etc.; or catechol-amines can be used to introduce cationic amine-functionality to titania, etc.; oxidizing the newly introduced sulfhydryl-group with hydrogen peroxide to generate anionic sulfonate-functionality can further chemically alter the introduced groups). Apart from changing the surface charge by introducing or modifying surface functionality, the introduction of different functional groups allows the conjugation of linkers (e.g., (cleavable or (bio-)degradable) polymers such as, but not limited to, polyethylene glycol, polypropylene glycol, PLGA, etc.), targeting/homing agents (e.g., such as, but not limited to, small molecules (e.g., folates, dyes, etc), (poly)peptides (e.g., RGD, epidermal growth factor, chlorotoxin, etc), antibodies, proteins, etc.), contrast/imaging agents (e.g., fluorescent dyes, (chelated) radioisotopes (SPECT, PET), MR-active agents, CT-agents), therapeutic agents (e.g., small molecule drugs, therapeutic (poly)peptides, therapeutic antibodies, (chelated) radioisotopes, etc), or combinations thereof.

Dopant Entity

In accordance with many embodiments of the present disclosure, dopant entities can be associated within one or more layers of a nanoparticle. In some embodiments, dopant entities are attached directly or indirectly to layers. In some embodiments, dopant entities are distributed within layer; in some embodiments, dopant entities are discretely localized within layers.

In general, dopant entities can be encapsulated independently within any possible distance from a substrate of a nanoparticle. Exemplary distance includes 5 µm, 1 µm, 800 nm, 500 nm, 400 nm, 300 nm, 200 nm, 100 nm, 90 nm, 80 nm, 70 nm, 60 nm, 50 nm, 40 nm, 30 nm, 20 nm, 15 nm, 10 nm, 5 nm, 1 nm, 0.5 nm, or 0.1 nm.

In some embodiments, dopant entities are positioned within a predetermined distance from the surface of a substrate or an adjacent layer. Such a distance in various embodiments can be about or less than 1 nm, 2 nm, 3 nm, 4 nm, 5 nm, 6 nm, 7 nm, 8 nm, 9 nm, 10 nm, 15 nm, 20 nm, 30 nm, 40 nm, 50 nm, 100 nm, 200 nm, 300 nm, 400 nm, or 500 nm. In some embodiments, a distance between a dopant entity and the surface of a substrate is a range of 2 nm to 5 nm, 5 nm to 10 nm, or 10 nm to 15 nm. In some embodiments, dopant entities can be in direct contact to the surface of a substrate or an adjacent layer.

In some embodiments, surface primers can be used after substrate synthesis. Exemplary surface primers include, but are not limited to, functionalized silica agents such as MPTMS and APTMS, or polymer (e.g., polyethyleneglycol-(PEG)-thiol).

In some embodiments, dopant entities have sufficient affinity for one or more components of a nanoparticle to permit displacement of a capping agent and/or to permit high density and/or close surface localized loading of the dopant entity(ies) into or onto the nanoparticle. A capping agent can be an entity that can be or is displaceable associated with a substrate. Without wishing to be bound by any particular theory, it is noted here that, in some embodiments, capping agents can play an important role in substrate synthesis. In some embodiments, capping agents control the size and geometry of a substrate. In some embodiments, capping agents are present after synthesis as an adsorbed monolayer on the synthesized substrate. In some embodiments, capping agents are strongly adsorbed to the surface of a substrate. In some embodiments, capping agents provide stabilization and/or prevent aggregation of substrates. Exemplary capping agents include, but are not limited to, organic agents such as citrate, citric acid, ascorbic acid, ascorbate, palmitoylascorbate, tetrakis(hydroxymethyl) phosphonium chloride, and amino acids. In some such instances, some or all capping agents are ultimately removed from a substrate by surface primers. In contrast to traditional surface priming methods wherein capping agents are displaced by surface primers, in some embodiments of the present disclosure a capping agent itself is employed to enable substrate encapsulation.

In various embodiments, one or more layers can have one or more entities/agents (e.g., detectable entities, targeting entities, or PEG) doped within. In general, any entity of interest can be utilized as a dopant entity in accordance with the present invention. A single dopant entity (or a layer/substrate) can be susceptible to imaging in multiple modalities.

In some embodiments, a dopant entity is a detectable entity including, but not limited to, SE(R)RS-active agent, fluorochromes (e.g., near infrared (metal-enhanced fluorescence agent, 2-photon fluorescence agent), MRI agents, photoacoustic-active dyes, upconverting materials, positron emission tomography (PET) tracers, single photon emission tomography (SPECT) tracers, computed tomography (CT) agents, X-Rays agents, ultrasound (US) agents and combinations thereof.

In some embodiments, layers can be doped with compounds/materials such as, but not limited to, SER(R)S-active dyes, (near infrared) fluorescent dyes, luminescent compounds, photoacoustic-active dyes, upconverting materials (e.g., consisting of materials from the group of the rare-earth metals and/or transition metals), (laser) pumping materials (e.g., consisting of, but not limited to, materials from the group of the rare-earth metal- and/or transition metal-based compounds), "slow light"-inducing materials (e.g., praseodymium-based compounds), MRI-active materials (e.g., consisting of, but not limited to rare-earth metals and/or transition metals such as gadolinium, manganese, iron(-oxides)). In some embodiments, at least one layer is doped with for instance a SERRS-active dye and at least one other layer is doped with for instance a near infrared fluorescent dye. In certain embodiments, some layers do not contain dopants but serve as spacers and/or separators between two dopant-containing shells. Layers can additionally be doped with therapeutic agents consisting of, but not limited by, (radiolabeled-) small molecule-, chelate-, peptide-, protein-, antibody, RNA, DNA, aptamer-based compounds/materials, and combinations thereof.

SE(R)RS-Active Agents

In some embodiments, a dopant entity is or comprises a dye, for example, a resonance dye. A dopant entity can be or comprise an agent useful in Raman spectroscopy (e.g., SE(R)RS-active agents). Exemplary dopant entities include, but are not limited to, those agents described in the art such as in U.S. Pat. Nos. 5,306,403; 6,002,471; and 6,174,677, the contents of which are incorporated by reference.

In some particular embodiments, a dopant entity is SE(R) RS- and/or photoacoustic active agent(s). In some particular embodiments, a high density of a SE(R)RS-active agent located close to a substrate contributes to unprecedented Raman sensitivity achieved by a particle described herein. SE(R)RS-active agents generally benefit from signal intensity enhancement in the proximity of a metal surface. In accordance with the present disclosure, a skilled artisan in the art would be capable to choose a SE(R)RS-active agent, to achieve chemical enhancement and/or electromagnetic enhancement, considering factors such as substrate materials, substrate configurations, layer material, etc. Such a SE(R)RS-active agent can have a charge transfer effect, from a metal to the molecule, or from the molecule to the metal.

A SE(R)RS-active agent refers to a molecule that is capable of generating a SERS or SE(R)RS spectrum when appropriately illuminated. Non-limiting examples of SE(R) RS-active agents include phthalocyanines such as methyl, nitrosyl, sulphonyl and amino phthalocyanines, naphthalocyanines, chalcogen-based dyes, azomethines, cyanines, squaraines, and xanthines such as the methyl, nitro, sulphano and amino derivatives. Each of these may be substituted in any conventional manner, giving rise to a large number of useful labels. It is noted that the choice of a SE(R)RS-active agent can be influenced by factors such as the resonance frequency of the molecule, the resonance frequency of other molecules present in a sample, etc.

Typically, detecting a SE(R)RS signal involves using incident light from a laser. The exact frequency chosen will depend on the SE(R)RS-active agent, and metal surface. Frequencies in visible or near-infrared spectrum tend, on the whole, to give rise to better surface enhancement effects for noble metal surfaces such as silver and gold. However, it is possible to envisage situations in which other frequencies, for instance in the ultraviolet range might be used. The selection and, if necessary, tuning of an appropriate light source, with an appropriate frequency and power, will be well within the capabilities of one of ordinary skill in the art, particularly on referring to the available SE(R)RS literature.

The Raman enhancement generally is proportional to the density of a SE(R)RS-active agent associated (e.g., adsorbed) on a metal surface. A surprisingly high density of a SE(R)RS-active agent adsorbed on a substrate surface in accordance with the present disclosure may contribute to the superior sensitivity of particles disclosed herein.

Fluorescent Agents

In some embodiments, a dopant entity is or comprises a fluorescent dye/agent (e.g., near infrared (NIR) fluorescent dye). For example, fluorescent dyes/agents including, but not limited to, polymethines, cyanines, (na)phthalocyanines, porphorines, merocyanines, (pe)rylene (bisimides), squaraines, anthocyanins, phycocyanins, bodipys, rotaxanes, rhodamines, certain organometallic complexes, can be used in accordance with the present invention.

In some embodiments, a fluorescent dye/agent has a predetermined distance from a substrate by means of synthesis method described therein. In some embodiments, a nanoparticle is doped with a near infrared (NIR) fluorescent dye and other agents.

MRI Agents

In some embodiments, a dopant entity is or comprises an MRI agent. In some embodiments, the amount or number of MRI agents associated with a layer can be about 1 to 10,000,000 MRI agents or about 5,000 to 500,000 MRI agents. See US Patent Application Publication No. 20120179029, the contents of which are incorporated by references.

Some embodiments of a MRI agent can be Gd(-salts), iron oxide, paramagnetic chemical exchange saturation transfer (CEST) agents, 19F active materials, manganese, melanin, or a substance that shortens or elongates T1 or T2 and a combination thereof. In certain embodiments, a Gd MRI agent can be a compound such as DOTA-Gd, DTPA-Gd, Gd within a polymeric chelator, and Gd immobilized by negative charges on a layer. In certain embodiments, an iron oxide MRI agent can be a compound such as a small paramagnetic iron oxide (SPIO) or an ultrasmall SPIO with or without a dextran or other stabilizing layer. In certain embodiments, a paramagnetic CEST MRI agent can be a compound such as lanthanide complexes.

In some embodiments, MRI agents can be linked to a layer via a linkage such as a maleimide linkage, NHS ester, click chemistry, or another covalent or non-covalent approach or a combination thereof. In some embodiments, MRI agents can also be loaded without addition of any exogenous agent, i.e., only layer(s) and MRI agent.

Alternatively or in addition to MRI agents, one or more other agents can be associated with a particle. Exemplary diagnostic agents including a PET (e.g., $^{18}F$, $^{64}Cu$, $^{11}C$, $^{13}N$, $^{15}O$, and the like), SPECT (e.g., $^{99}Tc$, $^{67}Ga$, $^{192}Ir$ and the like), fluorochrome (e.g., Alexa 647, Alexa 488 and the like), radio nuclide (e.g., alpha-emitting radionuclides (e.g., At-211, Bi-212, Bi-213, Ra-223, and Ac-225), beta-emitting radionuclides (e.g., Cu-67, Y-90, Ag-111, I-131, Pm-149, Sm-153, Ho-166, Lu-177, Re-186, and Re-188)), and the like, can be associated with a particle and be detected using appropriate detection systems. In certain embodiments, the use of a radionuclide can be used to induce signal via Cerenkov radiation.

In addition to detectable entities or alternatively, particles described herein can be prepared with dopant entities that are agents intended for administration or delivery. In some embodiments, such an agent remains associated with the particle after administration of the particle; in some embodiments, such an agent is released or otherwise dissociated from the particle after administration.

Any of a wide range of dopant entities may be used in accordance with the present invention. For example, dopant entities may be or comprise any therapeutic agents (e.g., antibiotics, NSAIDs, angiogenesis inhibitors, neuroprotective agents), cytotoxic agents, diagnostic agents (e.g., contrast agents; radionuclides; and fluorescent, luminescent, and magnetic moieties), targeting agents, prophylactic agents (e.g., vaccines), and/or nutraceutical agents (e.g., vitamins, minerals, etc.), or other substances (e.g., salt) that may be suitable for introduction to biological tissues, including pharmaceutical excipients and substances for cosmetics, and the like. Exemplary dopant entities may include, but are not limited to, therapeutic agents and/or imaging agents.

Targeting Agents

In some embodiments, Raman nanoparticles described herein include one or more targeting agent to facilitate and/or enhance the targeting of nanoparticles to a diseased tissue. Targeting agents include, e.g., various specific ligands, such as antibodies, monoclonal antibodies and their fragments, folate, mannose, galactose and other mono-, di-, and oligosaccharides, and RGD peptide. Additional examples of targeting agents include, but are not limited to, nucleic acids (e.g., RNA and DNA), polypeptides (e.g., receptor ligands, signal peptides, avidin, Protein A, and antigen binding proteins), polysaccharides, biotin, hydrophobic groups, hydrophilic groups, drugs, and any organic molecules that bind to receptors.

In some embodiments, a targeting agent is an antigen binding protein (e.g., an antibody or binding portion thereof). Antibodies can be generated using known methods to allow for the specific targeting of antigens or immunogens (e.g., tumor, tissue, or pathogen specific antigens) on various biological targets (e.g., pathogens, or tumor cells). Such antibodies include, but are not limited to, polyclonal antibodies; monoclonal antibodies or antigen binding fragments thereof; modified antibodies such as chimeric antibodies, reshaped antibodies, humanized antibodies, or fragments thereof (e.g., Fv, Fab', Fab, F(ab')2); or biosynthetic antibodies, e.g., single chain antibodies, single domain antibodies (DAB), Fvs, or single chain Fvs (scFv). Methods of making and using polyclonal and monoclonal antibodies are well known in the art, e.g., in Harlow et al., Using Antibodies: A Laboratory Manual: Portable Protocol I. Cold Spring Harbor Laboratory (Dec. 1, 1998). Methods for making modified antibodies and antibody fragments (e.g., chimeric antibodies, reshaped antibodies, humanized antibodies, or fragments thereof, e.g., Fab', Fab, F(ab')2 fragments); or biosynthetic antibodies (e.g., single chain antibodies, single domain antibodies (DABs), Fv, single chain Fv (scFv), and the like), are known in the art and can be found, e.g., in Zola, Monoclonal Antibodies: Preparation and Use of Monoclonal Antibodies and Engineered Antibody Derivatives, Springer Verlag (Dec. 15, 2000; 1st edition).

In some embodiments, the targeting agent is a nucleic acid (e.g., RNA or DNA). In some examples, the nucleic acid targeting agents are designed to hybridize by base pairing to a particular nucleic acid (e.g., chromosomal DNA, mRNA, or ribosomal RNA). In other situations, the nucleic acids bind a ligand or biological target. For example, the nucleic acid can bind reverse transcriptase, Rev or Tat proteins of HIV (Tuerk et al., Gene 137:33-9 (1993)); human nerve growth factor (Binkley et al., Nuc. Acids Res. 23:3198-205 (1995)); or vascular endothelial growth factor (Jellinek et al., Biochem. 83:10450-10456 (1994)). Nucleic acids that bind ligands can be identified by known methods, such as the SELEX procedure (see, e.g., U.S. Pat. Nos. 5,475,096; 5,270,163; and 5,475,096; and WO 97/38134; WO 98/33941; and WO 99/07724). The targeting agents can also be aptamers that bind to particular sequences.

The targeting agents can recognize a variety of known epitopes on preselected biological targets (e.g., pathogens or tumor cells). In some embodiments, the targeting agent targets nanoparticles to factors expressed by oncogenes. These can include, but are not limited to, tyrosine kinases (membrane-associated and cytoplasmic forms), such as members of the Src family; serine/threonine kinases, such as Mos; growth factor and receptors, such as platelet derived growth factor (PDDG), small GTPases (G proteins), including the ras family, cyclin-dependent protein kinases (cdk), members of the myc family members, including c-myc, N-myc, and L-myc, and bcl-2 family members.

Other Agents

In accordance with the present disclosure, a particle can include one or more agents for delivery after administration/implantation. Such an agent may be or comprise small molecules, large (i.e., macro-) molecules, or any combinations thereof. Additionally or alternatively, an agent can be a formulation including various forms, such as liquids, liquid solutions, gels, hydrogels, solid particles (e.g., microparticles, nanoparticles), or combinations thereof.

In representative, non-limiting, embodiments, an agent can be selected from among amino acids, vaccines, antiviral agents, nucleic acids (e.g., siRNA, RNAi, and microRNA agents), gene delivery vectors, interleukin inhibitors, immunomodulators, neurotropic factors, neuroprotective agents, antineoplastic agents, chemotherapeutic agents, polysaccharides, anticoagulants, antibiotics, analgesic agents, anesthetics, antihistamines, anti-inflammatory agents, vitamins and/or any combination thereof. In some embodiments, an agent may be selected from suitable proteins, peptides and fragments thereof, which can be naturally occurring, synthesized or recombinantly produced.

In some embodiments, an agent is or comprises a biologic. Examples of biologics including, but are not limited to, monoclonal antibodies, single chain antibodies, aptamers, enzymes, growth factors, hormones, fusion proteins, cytokines, therapeutic enzymes, recombinant vaccines, blood factors, and anticoagulants. Exemplary biologics suitable for use in accordance with the present disclosure are discussed in S. Aggarwal, Nature Biotechnology, 28:11, 2010, the contents of which are incorporated by reference herein.

In some embodiments, compositions and methods in accordance with the present application are particularly useful to deliver one or more therapeutic agents.

In some embodiments, a therapeutic agent is a small molecule and/or organic compound with pharmaceutical activity. In some embodiments, a therapeutic agent is a clinically-used drug. In some embodiments, a therapeutic agent is or comprises an anti-cancer agent, antibiotic, antiviral agent, anesthetic, anticoagulant, inhibitor of an enzyme, steroidal agent, anti-inflammatory agent, anti-neoplastic agent, antigen, vaccine, antibody, decongestant, antihypertensive, sedative, birth control agent, progestational agent, anti-cholinergic, analgesic, anti-depressant, anti-psychotic, β-adrenergic blocking agent, diuretic, cardiovascular active agent, vasoactive agent, anti-glaucoma agent, neuroprotectant, angiogenesis inhibitor, etc.

Exemplary anticancer agents included, but are not limited to, a cytokine, a chemokine, a growth factor, a photosensitizing agent, a toxin, an anti-cancer antibiotic, a chemotherapeutic compound, a radionuclide, an angiogenesis inhibitor, a signaling modulator, an anti-metabolite, an anti-cancer vaccine, an anti-cancer oligopeptide, a mitosis inhibitor protein, an antimitotic oligopeptide, an anti-cancer antibody, an anti-cancer agent, antibiotic, an immunotherapeutic agent, hyperthermia or hyperthermia therapy, a bacterium, radiation therapy and a combination of such agents. In some examples, an anticancer agent is cisplatin, carboplatin, gemcitabine, irinotecan, an anti-EGFR antibody, an anti-VEGF antibody and any combinations thereof.

A therapeutic agent used in accordance with the present application can be or comprise an agent useful in combating inflammation and/or infection. A therapeutic agent may be an antibiotic. Exemplary antibiotics include, but are not limited to, β-lactam antibiotics, macrolides, monobactams, rifamycins, tetracyclines, chloramphenicol, clindamycin, lincomycin, fusidic acid, novobiocin, fosfomycin, fusidate sodium, capreomycin, colistimethate, gramicidin, minocycline, doxycycline, bacitracin, erythromycin, nalidixic acid, vancomycin, and trimethoprim. For example, β-lactam antibiotics can be ampicillin, aziocillin, aztreonam, carbenicillin, cefoperazone, ceftriaxone, cephaloridine, cephalothin, cloxacillin, moxalactam, penicillin G, piperacillin, ticarcillin and any combination thereof. Other anti-microbial agents such as copper may also be used in accordance with the present invention. For example, anti-viral agents, anti-protazoal agents, anti-parasitic agents, etc. may be of use. Additionally or alternatively, a therapeutic agent may be an anti-inflammatory agent.

A therapeutic agent may be a mixture of pharmaceutically active agents. For example, a local anesthetic may be delivered in combination with an anti-inflammatory agent such as a steroid. Local anesthetics may also be administered with vasoactive agents such as epinephrine. To give but another example, an antibiotic may be combined with an inhibitor of the enzyme commonly produced by bacteria to inactivate the antibiotic (e.g., penicillin and clavulanic acid).

In some embodiments, a therapeutic agent may a therapeutic gene as known in the art. In some embodiments, a therapeutic agent is a non-viral vector. Typical non-viral gene delivery vectors comprise DNA (e.g., plasmid DNA produced in bacteria) or RNA. In certain embodiments, a non-viral vectors is used in accordance with the present invention with the aid of a delivery vehicle. Delivery vehicles may be based around lipids (e.g., liposomes) which fuse with cell membranes releasing a nucleic acid into the cytoplasm of the cell. Alternatively or alternatively, peptides or polymers may be used to form complexes (e.g., in form of particles) with a nucleic acid which may condense as well as protect the therapeutic activity as it attempts to reach a target destination.

Systems and Instruments

Systems of the disclosure include detectors and associated components for detecting Raman spectra from cells and/or tissues. In some embodiments, such systems include an excitation source (e.g., a light source), optics for directing such excitation source to a sample (e.g., cells and/or tissues), and a detector for detecting Raman spectra from such sample. In some implementations, the excitation source and optics are used to interrogate the presence of a Raman reporter and to ablate the area or region where presence of the Raman reporter is detected.

The light source for producing excitation light may include one or more lasers, and optics for directing the excitation light onto and/or into the target tissue are configured to disperse the excitation light evenly over the wide field corresponding to the target tissue. For example, near-infrared (NIR) could be used, e.g., 785 nm diodes, 300 mW, and/or 1064 nm Nd:YAG lasers. In some embodiments, the wavelength can be in the visible range, the near-infrared range, or in the mid-infrared range (e.g., about 500 nm to about 11 μm).

In some embodiments, a hyperspectral wide field imaging device is used with CCD detector and filter. For example, monochromatic images of the whole wide field are obtained at each of a plurality of wavelengths (e.g., a limited set of 2 to 10 wavelengths), each wavelength corresponding to a spectral peak characteristic of the Raman reporter. The laser may be a tunable laser source. Optics may include a tunable laser line filter (LLF) and/or a tunable notch filter (NF), where the filters are tandem thick volume Bragg gratings. The plurality of monochromatic images may be analyzed, by the detector, for graphical identification of the Raman reporters within the wide field. Images displaying the location of R-MR nanoparticle reporters (indicative of tumor or other abnormal tissue) may be superimposed, for example, on corresponding video images of the wide field, allowing the surgeon the ability to visualize such tissue and remove it with limited damage to surrounding healthy tissue.

The system may allow scanning/imaging of a wide field of view of about 5×5 cm, 10×10 cm, 20×20 cm. In some embodiments, the field of view is about 25 $cm^2$, 50 $cm^2$, 75 $cm^2$, 100 $cm^2$, 150 $cm^2$, 200 $cm^2$, 300 $cm^2$, 400 $cm^2$, 500 $cm^2$, or larger. Individual images of R-MR nanoparticles may be acquired within seconds, for example, or less than a second, such that a real-time or near real-time sequence of images may be viewed (e.g., 10 images per second or more, e.g., 20 or more images per second).

In some embodiments, systems of the disclosure include detectors and associated components for detecting Raman spectra from cells and/or tissues and implements for treating (e.g., ablating and/or resecting) cells and/or tissues from which Raman spectra are detected. In some embodiments, such systems include an excitation source (e.g., a light source), optics for directing such excitation source to a sample (e.g., cells and/or tissues), a detector for detecting Raman spectra from such sample, and implements for treating (e.g., ablating and/or resecting) cells and/or tissues from which Raman spectra are detected.

In some embodiments, a system of the disclosure includes a handheld instrument of size and length that can be customized to a particular application. A system can include a resector/ablation mechanism (e.g., a mechanical resector (e.g., rotary blade, vibrating knife, or percussing knife), an electro-cautery mechanism, a cryoablation mechanism, and/or a radiofrequency ablation mechanism. A system can optionally include a vacuum suction mechanism connected to a collection bag that removes resected tissue from the site of resection. Adjacent and/or near the motorized resection mechanism within the handheld device can be located an excitation laser pathway and optics for measuring emitted Raman spectra. Optionally, a rinsing mechanism can be included within the device to help clean the optics. The hand-held device can be connected with a cable (e.g., fiberoptic cable) and tubing (e.g., suction tubing) to a box located adjacent to the operating site that houses mechanics, optics, and electronics (e.g., excitation laser, Raman spectral analysis optics, CCD chips, and optionally motors to drive the resection instrument, suction motor, and rinsing mechanism).

An exemplary system is illustrated schematically in FIG. 26. As shown in FIG. 26, system 2600 of the disclosure includes a hand-held instrument/housing 2601 having a terminal end 2612. The instrument 2601 may include optics for directing an excitation light onto a target sample 2630 (e.g., cells, or tissue). In this exemplary system, excitation light source 2602 is a Raman laser, for example, having a wavelength of 785 nm. The excitation light is transmitted along cable 2610 from excitation light source 2602 through device 2601 and is directed to target tissue 2630 through terminal end 2612. In some embodiments, the excitation light passes through one or more filters 2611 before reaching target 2630. The filter(s) may or may not be contained within the hand-held instrument 2601. In alternative embodiments, the excitation light is not directed onto the tissue 2630 by the hand-held instrument 2601, but instead is directed onto the tissue 2630 via optics, apart from the instrument 2601.

The system 2600 also includes a detector for detecting a signal from target 2630. Such signal follows cable 2620 to signal analyzer 2603. In this exemplary system, signal analyzer 2603 is a Raman analyzer. Upon determination that an appropriate signal is detected, signal analyzer 2603 relays a positive signal to ablation controller 2604. Ablation controller 2604 is operably linked to instrument 2601 via cable 2605, which terminates in an ablation device near terminal end 2612 of instrument 2601. Upon receiving a positive signal from ablation controller 2604, the ablation device ablates cells and/or tissue at or near target 2630. In some embodiments, ablation controller 2604 includes a mechanical ablation controller operably linked to a suction vacuum mechanism near terminal end 2612 of instrument 2601 via tubing 2606.

In alternative embodiments, the system 2600 includes a motor-driven and controlled resection mechanism (e.g., a rotating blade) located at the tip 2612 of the handheld device 2601, such that activation of the resection mechanism is triggered upon detection of a Raman signal by the Raman Analyzer 2603.

In some embodiments, a system of the disclosure includes a handheld instrument of size and length that can be customized depending on application. A system can include a laser suitable for ablating/destroying tissue (e.g., a $CO_2$, Er:YAG, or Nd:YAG laser). In some implementations, the ablating laser is also used as the excitation light source for interrogating an area of a tissue for the presence of the Raman reporter, e.g., where the power level is lower for interrogation and higher for ablation. A system can optionally include a vacuum suction mechanism connected to a collection bag that removes destroyed tissue (and, optionally, nanoparticles described herein) within targeted tissue. Adjacent to the ablation laser pathway within the handheld device can be located an excitation laser pathway and optics for measuring emitted Raman spectra. Optionally, a rinsing mechanism can be included within the device to help clean the optics. The handheld device can be connected with a cable (e.g., fiberoptic cable) and tubing (e.g., suction tubing) to a box located adjacent to the operating site that houses mechanics, optics, and electronics (e.g., excitation laser, ablation laser, Raman spectral analysis optics, CCD chip(s), and optionally motors to drive the suction motor, and rinsing mechanism).

Two exemplary systems are illustrated schematically in FIG. 27. As shown in FIG. 27, system 2700 of the disclosure includes a hand-held instrument 2701 having a terminal end 2714. The instrument 2701 includes a housing 2702 for directing an excitation light to a target sample 2715. In this exemplary system, excitation light source 2704 is a Raman laser, for example, having a wavelength of 785 nm. The excitation light is transmitted along cable 2707 from excitation light source 2704 through instrument 2701 and is directed to target 2715 through terminal end 2714. In some embodiments, the excitation light passes through one or more filters 2710 and 2712 before reaching target 2715. The filter(s) may or may not be contained within the hand-held instrument 2701. In alternative embodiments, the excitation light is not directed onto the tissue 2715 by the hand-held instrument 2701, but instead is directed onto the tissue 2715 via optics apart from the instrument 2701.

The system 2700 also includes a detector for detecting a signal from target 2715. Such signal travels through cable 2708 to signal analyzer 2705. In this exemplary system, signal analyzer 2705 is a Raman analyzer. Signal analyzer 2705 is operably linked to ablation laser 2706. In this exemplary system, ablation laser 2706 is a $CO_2$ laser. Upon determination that an appropriate signal is detected, signal analyzer 2705 relays a positive signal to ablation laser 2706. Ablation laser 2706 is operably linked to device 2701 via cable 2709, which directs the ablation laser through housing 2703 to target 2715. In some embodiments, ablation laser passes through filters 2711 and 2713 before reaching target 2715.

FIG. 27 also illustrates exemplary system 2750, which differs from system 2700 in the configuration of device 2751. As shown in FIG. 27, device 2751 includes housing 2752 for directing excitation light from an excitation light source and for directing Raman signals to a signal analyzer as described for system 2700. Device 2751 also includes housing 2753 for directing ablation laser to target 2758, as described for system 2700. Device 2751 includes filter 2754 and deflector 2756, which directs ablation laser along or near the same pathway used by the excitation light to reach target 2758.

FIG. 28 illustrates another exemplary system 2800. As shown in FIG. 28, the system 2800 employs an ablation laser 2802 that generates excitation light for interrogating the presence of a Raman reporter within or on the tissue sample 2814 and for ablating the area of the sample where the Raman signal is detected. Ablation laser 2802 may be operably linked to a separate, hand-held device/housing 2804 via cable 2810, which directs the ablation laser through housing 2804 to target 2814.

In some implementations, the ablation laser 2802 first outputs the excitation light source at an interrogation power level sufficient to penetrate the tissue to a desired depth for detection of the Raman reporter in that region yet not high enough to cause damage (e.g., via thermal or ionizing energy) to the tissue or sample. In certain implementations, the interrogation power level is less than 20 milliwatt or less than 10%, for example, of the maximum power level of the ablation laser. Other power levels may be employed for the interrogation and may be selected based on, for example, but not limited to, the type and/or density of the tissue, the depth of the intended interrogation, the type of Raman reporter used, and the wavelength/frequency of the outputted excitation light source.

The ablation laser 2802 is also configured to output an excitation source at an ablation power level sufficient to ablate the tissue when the presence of the Raman reporter is detected from the interrogation of the tissue. This level may be sufficient to cause heating, and in instances, vaporization, of the area or region in the vicinity of the Raman reporter. In some implementations, the effect is the result of the vibrational state of the Raman reporter when excited by the excitation source. In other implementations, the ablation power level is sufficient to cause damage to the tissue through this vibrational mode of the Raman reporter when excited by the excitation source. In such implementations, the heating, vaporization, or vibration damage may be the result of amplification of the Raman scattering by the Raman reporter due to the resonance effect with the excitation source. To this end, in such implementations, the ablation power level can be at a level that does not cause damage to the tissue or the area/region exposed to the excitation source unless the Raman reporter is present therein, or the exposure time by the excitation source may not be of sufficient duration. In yet other implementations, an ablation power level can be employed that is sufficient to directly cause thermal effects on the tissue exposed to the excitation light source, whereby the thermal effects cause the ablation of the tissue. In certain embodiments, the laser 2802 is a $CO_2$ laser. In other embodiments, the laser is a different kind of laser, as described elsewhere herein. In some implementations, the elevated ablation power level is above 150 mW. In such implementations, the power level can be between 50% and 100% of the maximum power output of the ablation laser.

As shown in FIG. 28, the system 2800 includes a housing 2804 for directing the excitation light source to a target sample 2814. The ablation laser 2802 has a wavelength of about 500 nm to about 11 µm. The ablation laser 2802 transmits the excitation light along cable 2810 through instrument 2804 and is directed to the target sample 2814 through a terminal end 2812. In some implementations, the system 2800 includes one or more filters and optics 2810

(such as prism) through which the excitation light passes 2712 before reaching the target 2814. The prism directs the returned light emanating from the tissue 2814 through one or more filters to cable 2808 to Raman analysis.

In some implementations, the filters and optics 2810 include an optical assembly comprising one or more confocal lens to vary the focus length of the excitation light source outputted from the system 2800. The optical assembly may control the depth of the spectral measurement (e.g., during the interrogation of the Raman reporter) to match to the depth of the ablation.

The system 2800 also includes a detector 2806 for detecting a signal from target 2814 received from cable 2808. In some implementations, the detector 2806 includes a charge-coupled device (CCD) coupled with a optics assembly and a transmission grating. For example, the optic assembly may collimate the detected lights from a slit, located at the entrance of the detector assembly, to the transmission grating. The grating disperses the incident light to the CCD detector by way of a focusing mirror. The detector converts the light to a signal for processing by the Raman analyzer 2806. A controller (not shown) operatively links the ablation laser 2802 and the Raman analyzer 2806. The Raman analyzer 2806 employs a correlation analysis, for example, to determine for the presence of a Raman signal associated with the Raman reporter (e.g., SERS nanoparticles, SERRS nanoparticles, or an intrinsic species). Upon determination that a Raman signature is present, the Raman analyzer 2806 triggers a signal to the controller or the ablation laser 2802 to elevate the output power level of the laser for a pre-defined period to ablate the tissue sample 2814. In some implementations, the elevated power level is above 150 mW. In such implementations, the power level can be between 50% and 100% of the maximum power output of the ablation laser. The ablation power level and exposure time may be a function of the tissue type and density, the depth of the intended ablation, the type of Raman reporter, and the wavelength of outputted excitation light sources.

It should be appreciated by those skilled in the art that other power levels may be employed. In certain implementations, higher power level may be employed with shorter ablation time, for example, to increase ablation speed.

FIG. 30 is an example method 3000 of operation of an ablation/scanning device. The ablation/scanning device is energized, at a scanning, non-ablating power level, to produce an electromagnetic radiation on the sample in which the sample has been treated (e.g., injected) with a Raman Reporter (e.g., SERS, SERRS, SERS-MRI, R-MR and other nanoparticles or intrinsic species) (step 3002). In some implementations, the non-ablating power is less than about 10% (e.g., between about 1% to 10%) of the maximum power of the laser, which may be equivalent to about few milliwatts (e.g., 1-20 mW). The ablation/scanning device acquires a spectrum of the resulting Raman scattering from the test sample in which the scattering is caused by the generated electromagnetic radiation (step 3004). The acquired spectrum may be filtered for a specific bandwidth.

The ablation/scanning device compares the acquired laser spectrum to a stored reference spectrum to generate a comparison index value (step 3006). In some implementations, the reference spectrum is a correlative profile of the Raman reporter ((e.g., SERS nanoparticles, SERRS nanoparticles, or an intrinsic species). In other implementations, the reference spectrum is a correlative profile of a specific type of tissue or tumor treated with the Raman reporter. In yet other implementations, the reference spectrum is a correlative profile of the Raman reporter when binded to a specific type of tissue or tumor. The reference spectrum may be stored in memory of the ablation/scanning device.

Still referring to FIG. 30, if the ablation/scanning device determines that the current location of the tissue sample does not have the Raman reporter, the device moves to a next location (step 3010). The next location may be a pre-defined step from the current location. In some embodiments, the ablation/scanning device continuously outputs the laser at the scanning, non-ablating power level while the laser is moved to the next location or the laser may be de-energized.

Upon a determination that the index exceeds a specified threshold (e.g., between 50-99%), the ablation/scanning device energizes the laser at an ablation power at the same point location (step 3008). In some implementations, the laser is outputted between about 50 percent and 100 percent of the maximum power output of the laser. The output may have a duration of, for example, about 1 to about 200 milliseconds. Subsequently, the Raman ablation device is rastered to a next location (step 3010).

In some implementation, the Raman ablation device repeats steps 3002 to 3008 at a given ablated location or region. In such implementations, the Raman ablation device outputs a second ablation output, and subsequent ablation outputs, if a Raman reporter is still detected there.

FIGS. 31A and 31B are schematic illustrations of an exemplary method of controlling a laser ablation and Raman scanning device of the disclosure. As shown in FIG. 31A, the interrogation source 3102 and ablation source 3104 may be outputted in pulses. The interrogation source 3102 may have duration less than 120 milliseconds (equivalent to about 10 hertz).

As shown in FIG. 31B, the interrogation source 3106 and ablation source 3108 may be continuous in which the interrogation source 3106 is continually output. Then, upon a Raman reporter being detected by the system, the interrogation source 3106 is elevated to a power level sufficient to ablate the tissue or sample (in some embodiments, the ablation due at least in part to additional energy provided by the Raman reporter, itself, to the nearby tissue).

The instruments 2601, 2701, 2750, and 2800 described above, instead of being hand-held, may be endoscopic instruments designed for insertion into a patient, for example, into the gastrointestinal tract, the respiratory tract, the ear, the urinary tract, the female reproductive system, the abdominal or pelvic cavity, the interior of a joint (arthroscopy), organs of the chest, or the amnion.

In some embodiments, systems 2600, 2700, and 2800 described above additionally include one or more additional modalities for detecting a Raman nanoparticle, and/or for otherwise detecting tissue to be ablated or resected. For example, the system further includes MRI, NMR, PET, SPECT, CT, X-ray, ultrasound, photoacoustic, and/or fluorescent detection modalities.

Systems of the disclosure described herein may have components of small size (e.g., micromechanical components), such that the systems may be used in microsurgical procedures.

Systems of the disclosure described herein may be robot-assisted or robot-guided. For example, the instrument 2601, 2701, 2751, and 2802 may be part of a robotic system that positions and/or moves the instrument automatically or semi-automatically. Other components of known robotic surgical systems may be used in conjunction with the systems of this disclosure.

In some embodiments, a system described herein further includes a Raman raster scanning device. For example, a Raman raster scanning device can be used to scan (e.g., systematically scan) a field having a particular dimension (e.g., a surface area of target tissue). FIG. 29 illustrates an exemplary system for using a Raman scanning device, which can be used in any of the embodiments described herein. As shown in FIG. 29, a controller is operably linked to a motor, which manipulates the position of a stage (e.g., an X-Y stage, an X-Y-Z stage, or an XYZ/rotation stage).

The system may raster between sampling points at step sizes between 0.1 mm and 10 mm apart. In certain implementations, the step size is greater than 10 mm. The system may perform an initial scan at a coarse step size (e.g., 1-10 mm) to identify tissue areas of interest. Subsequently, the system then perform an ablation scan at a finer step size (e.g., 0.1 mm to 2 mm) to scan and ablate the tissue. The finer step size may be a function of the laser spot (e.g., between 5 μm to 2 mm) and the sample acquisition rate (e.g., greater than 10 Hz).

Excitation Sources

Generally, excitation light for producing Raman photon scattering from a target cell and/or tissue is provided using a laser. Particular wavelengths useful in producing Raman scattering can be determined by the target to be excited. In some embodiments, excitation light is in the visible to near infrared range (e.g., about 400 nm to about 1400 nm). For example, in some embodiments, excitation light of 244 nm, 325 nm, 442 nm, 488 nm, 514 nm, 532 nm, 633 nm, 785 nm, or 830 nm can be used.

Selection of a particular wavelength for excitation light can be based on the particular substance to be excited. In some embodiments, a Raman nanoparticle, e.g., a SERS nanoparticle, is excited to produce Raman scattered photons. The composition of a particular Raman nanoparticle can be used to select an appropriate wavelength. In some embodiments, a SERS nanoparticle described in Kircher et al., Nature Med. 18:829-834 (2012); Yigit et al., Am. J. Nucl. Med. Mol. Imaging 2:232-241 (2012); Zhang et al., Small. 7:3261-9 (2011); or Zhang et al., Curr. Pharm. Biotechnol. 11:654-661 (2010) is used, and excitation light of 785 nm is used.

In some embodiment, an intrinsic non-enhanced or intrinsic enhanced (SERS) Raman spectrum of a tissue to be destroyed is excited. In such embodiments, selection of a particular wavelength of excitation light can be determined by particular properties of the diseased tissue.

Detectors

Raman scattered photons from an illuminated sample can be collected and transmitted to one or more detectors. The detector(s) may be or may include a charge-coupled device (CCD) image sensor, for example, a time-gated intensified CCD camera (e.g., an ICCD camera). Alternatively or additional, the detector(s) may include an active pixel sensor (CMOS), an electron-multiplying CCD (EMCCD), frame transfer CCD, or the like.

In some embodiments, electromagnetic radiation used to obtain Raman images is transmitted to a detector in a "mappable" or "addressable" fashion, such that radiation (e.g., light) transmitted from different assessed regions of tissue can be differentiated by the detector. Light detected by a detector can be light transmitted, reflected, emitted, or scattered by the tissue through air interposed between the tissue surface and the detector. Alternatively, light can be transmitted by way of one or more optical fibers to the detector, for example. In some embodiments, one or more additional optical elements can be interposed between a target cell and/or tissue and detector(s). If optical elements are used to facilitate transmission from the surface to the detectors, other optical element(s) can be optically coupled with the fibers on either end or in the middle of such fibers. Examples of suitable optical elements include one or more lenses, beam splitters, diffraction gratings, polarization filters, bandpass filters, or other optical elements selected for transmitting or modifying light to be assessed by detectors. One or more appropriate optical elements may be coupled with a detector.

For example, a suitable filter can be a cut-off filter, a Fabry Perot angle tuned filter, an acousto-optic tunable filter, a liquid crystal tunable filter, a Lyot filter, an Evans split element liquid crystal tunable filter, a Solc liquid crystal tunable filter, or a liquid crystal Fabry Perot tunable filter. Suitable interferometers include a polarization-independent imaging interferometer, a Michelson interferometer, a Sagnac interferometer, a Twynam-Green interferometer, a Mach-Zehnder interferometer, and a tunable Fabry Perot interferometer.

Tissue Ablation/Resection

As discussed herein, after a Raman signal is detected from cells and/or tissue, such cells and/or tissue are ablated or resected using known implements and/or methods for ablating or resecting cells and/or tissues, such as laser ablation, mechanical ablation, electro-cautery, radiofrequency ablation, and/or cryoablation.

In some embodiments, ablation is achieved using radiofrequency energy. Additional forms of energy for ablation include, without limitation, microwave energy, or photonic or radiant sources such as infrared or ultraviolet light. Photonic sources can include, for example, semiconductor emitters, lasers, and other such sources. Light energy may be either collimated or non-collimated. In some embodiments, ablation utilizes heatable fluids, or, alternatively, a cooling medium, including such non-limiting examples as liquid nitrogen, Freon™, non-CFC refrigerants, $CO_2$ or $N_2O$ as an ablation energy medium. For ablations using hot or cold fluids or gases, an apparatus can be used to circulate heating/cool medium from outside a patient to a heating/cooling balloon or other element and then back outside the patient again. Mechanisms for circulating media in cryosurgical probes are well known in the ablation arts. For example, and incorporated by reference herein, suitable circulating mechanisms are disclosed in U.S. Pat. No. 6,182, 666; 6,193,644; 6,237,355; and 6,572,610.

In some embodiments, light energy is used to ablate cells and/or tissues, and laser light is precisely aimed to cut or destroy diseased cells and/or tissue (e.g., a tumor) according to methods of the disclosure. In some embodiments, a method, system or device described herein is used to delivery laser-induced interstitial thermotherapy (LITT), or interstitial laser photocoagulation to target cells or tissues. LITT uses heat to shrink tumors by damaging or killing cancer cells. In some embodiments, a method, system or device described herein is used to delivery photodynamic therapy (PDT). In PDT, a certain drug (e.g., a photosensitizer or photosensitizing agent) is injected into a patient and absorbed by cells all over the patient's body. After a couple of days, the agent is found mostly in cancer cells. Laser light is then used to activate the agent and destroy cancer cells.

Lasers typically used to destroy cancerous tumors include solid state lasers, gas lasers, semiconductor lasers, and others. Typical wavelengths of electromagnetic radiation used in cancer treatments are from about 200 nm to about 5000 nm, and to about 12 μm for $CO_2$ lasers. Typical power levels range from about 0.1 W to about 15 W, and to about 30 W for $CO_2$ lasers. However, greater or lesser power levels may be used in some circumstances. Typical treatment times for exposing cancerous cells to laser energy range from less than about 1 minute to greater than about 1 hour, although longer or shorter times may be used. The laser energy applied to the cancerous cells may also be modulated. Laser energy may be applied to cancerous cells by continuous wave (constant level), pulsing (on/off), ramping (from low to high energy levels, or from high to low energy levels), or other waveforms (such as sine wave, square wave, triangular wave, etc.). Modulation of laser energy may be achieved by modulating energy to the laser light source or by blocking or reducing light output from the laser light source according to a desired modulation pattern.

Specific lasers for ablation of cells and/or tissues are known in the art. Exemplary, nonlimiting lasers useful in the methods, systems, and devices described herein include carbon dioxide ($CO_2$) lasers, argon lasers, neodymium-doped yttrium-aluminum-garnet (Nd:YAG) lasers, and erbium-doped yttrium-aluminum-garnet (Er:YAG) lasers.

In some embodiments, cells and/or tissues are resected mechanically using, e.g., an electrically powered rotary blade. Additional mechanical resection mechanisms and/or methods may also be used. Resection mechanisms may include, for example, drills, dermatomes, scalpels, lancets, drill bits, rasps, trocars, and the like.

Other surgical instruments may be used in conjunction with the ablation and resection mechanisms described above, including, for example forceps, clamps, retractors, dilators, suction tips and tubes, irrigation needles, injection needles, calipers, and the like.

Raman-Triggered Ablation System with Laser that Performs Both Interrogation and Ablation An exemplary setup for a Raman-triggered ablation device is now described. A sample comprised of Raman spectroscopic (SERRS) nanostar nanoparticles having a concentration of 5 nM is treated on a surface of workpiece. The sample was staged under a Raman spectrometer probe mounted on a linear scanning system. The probe is connected to a 240 milliwatt, 785 nm, $CO_2$ laser. The probe and scanning system were controlled from a computing device operating a graphical user interface (GUI). The Raman spectrometer probe used in this exemplary system is a Miniram Raman Spectrometer manufactured by BWTek of Newark, Del., model BAC-100. The GUI was programmed in Matlab of Mathworks of Natick, Mass.

The computing device evaluated the acquired spectral data with signal pre-processing, e.g., background 'dark' subtraction and mean normalization of the acquired data. Several correlative algorithms were implemented and tested. It was found that the Correlation Coefficient algorithm produced the most robust results in this exemplary system among the algorithm employed. Examples of correlative analysis may be found in Kwiatkowski et al., Algorithms of Chemical Detection Using Raman Spectra," Metrol. Meas. Syst., Vol. XVII, No. 4, pp. 549-560 (2010).

In each loop, the device energized the laser at a non-ablating power level to interrogate for the presence of Raman reporter in that area. An optic assembly of the spectrometer probe directs the output of the laser to a point on the test sample. The device outputted an excitation source with a beam size of approximately 400 micrometer at a power level of about 3% of the maximum output power of the laser, or about 7-8 milliwatt. The interrogation beam was outputted for about 100 milliseconds.

The device acquired a spectrum of the Raman scatter from the interrogated area during this 100 milliseconds. The acquired spectrum was compared to a reference spectrum (indicative of presence of the Raman reporter) to generate a comparison index by correlative analysis.

Using the Correlation Coefficient algorithm, if the comparison index is above a threshold (e.g., 0.75), the device is configured to energized the laser to the maximum power (~240 mW) for a duration sufficient to heat and flash-burn the particles on the test sample (e.g., the treated paper). In this exemplary example, the duration is set to 100 milliseconds. The comparison index is calculated, in some implementation, based on:

$$\frac{\sum_{i=1}^{n}(s_i-s)(r_i-r)}{\sqrt{\sum_{i=1}^{n}(s_i-s)^2 \sum_{i=1}^{n}(r_i-r)^2}},$$

in which $s_i$ is the acquired spectrum at acquisition point i, $r_i$ is the reference spectrum at point i, s is the mean of the acquired spectrum, and r is the mean of the reference spectrum, and n is the number acquisition points. Subsequently, the laser is turned off and the probe is moved to a next test point.

FIG. 32 is a diagram of an example graphical user interface (GUI) used to control the Raman spectrometer in this exemplary system. The GUI continuously generates and displays a comparison index (HQI) 3202 between the reference spectrum and the acquired spectrum. The GUI also generates and plots the acquired spectrum (3206) and the reference spectrum (3204) used in the comparison. As shown, the index has a range of 0-100 (on a scale of 0-100) in which 100 means an identical data sets.

FIG. 33 shows data acquired via a Raman ablation and scanning device 3302.

The sequence in the figure shows the device 3302 scanning over a test sample 3308. The test sample 3308 is a paper partially treated with a Raman reporter. Here, the Raman reporter includes 5 nanomolar (nM), SERRS-nanostar nanoparticles. In FIG. 33, Subfigure A, the probe 3302 is shown scanning a point 3306A on the test sample 3308 not treated with the Raman reporter. Each scan was performed at 3% of the maximum output of the laser (or 7-8 milliwatt) for approximately 100 milliseconds. The system determined that the acquired spectrum at point 3306A does not have the Raman signature of interest when compared to a stored reference spectrum of the Raman reporter and moved to a next interrogation location. The total acquisition time took approximately 120 milliseconds to provide a scanning rate of about 10 Hertz.

In FIG. 33, Subfigure B, the system is shown interrogating a point 3306B near the border of the surface area 3304 treated with the SERRS-nanostar nanoparticles. The system determined that the point 3306B did not have the spectral signature of interest and subsequently moved to a next test location.

In FIG. 33, Subfigure C, the system is shown interrogating a point 3306C on the treated surface area 3304. The system determined that the acquired spectrum at point 3306C has the Raman signature of interest when compared to the stored reference spectrum and increased the laser output to an ablation power level (in this setup, at 100% of the maximum power, or about 240 milliwatt, of the $CO_2$ laser for a duration of 100 milliseconds) causing the paper and nanoparticle to heat up and flashburn. It was observed that the SERRS-nanostar nanoparticles assisted in the ablation of the test sample.

In FIG. 33, Subfigure D, the system is shown interrogating another point 3306D on the treated surface area 3304. The system determined that the point 3306C includes the Raman signature of interest and is also ablated.

In FIG. 33, Subfigures E and F, the system is shown interrogating two points 3306E and 3306F not treated with the Raman reporter. The interrogated points 3306E, 3306F were not ablated.

FIG. 34 shows the thermal paper 3308 of FIG. 33 subsequent to being scanned and ablated by the Raman scanning and ablation system 3302. The left image shows the top view 3402 of the thermal paper 3308 that was treated with the Raman reporter and was exposed to the laser beam during the interrogation and ablation. The right image shows the bottom view 3404 of the paper 3308. As shown, the areas 3406 treated with the Raman reporter were ablated by the laser if scanned by the system.

Among other things, the data demonstrate that an acquisition rate greater than 10 Hertz can be employed robustly using low interrogation power levels and that the ablation and interrogation may be performed by the same laser. The results also demonstrated that the Raman reporter can be employed to assist in the ablation event.

Cells/Tissues

The methods, systems, and devices described herein can be used to resect and/or ablate a variety of cells and/or tissues, e.g., diseased cells and/or tissues. The methods, systems, and devices described herein can also be used to identify and/or distinctly visualize a variety of cells and/or tissues, e.g., diseased cells and/or tissues. In some embodiments, methods described herein identify hyperproliferative, hyperplastic, metaplastic, dysplastic, and pre-neoplastic tissues.

By "hyperproliferative tissue" is meant a neoplastic cell growth or proliferation, whether malignant or benign, including all transformed cells and tissues and all cancerous cells and tissues. Hyperproliferative tissues include, but are not limited to, precancerous lesions, abnormal cell growths, benign tumors, malignant tumors, and cancer. Additional nonlimiting examples of hyperproliferative tissues include neoplasms, whether benign or malignant, located in the brain, prostate, colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, or urogenital tract.

As used herein, the term "tumor" or "tumor tissue" refers to an abnormal mass of tissue that results from excessive cell division. A tumor or tumor tissue comprises "tumor cells", which are neoplastic cells with abnormal growth properties and no useful bodily function. Tumors, tumor tissue, and tumor cells may be benign or malignant. A tumor or tumor tissue can also comprise "tumor-associated non-tumor cells", such as vascular cells that form blood vessels to supply the tumor or tumor tissue. Non-tumor cells can be induced to replicate and develop by tumor cells, for example, induced to undergo angiogenesis within or surrounding a tumor or tumor tissue.

As used herein, the term "malignancy" refers to a non-benign tumor or a cancer. As used herein, the term "cancer" means a type of hyperproliferative disease that includes a malignancy characterized by deregulated or uncontrolled cell growth. Examples of cancer include, but are not limited to, carcinoma, lymphoma, blastoma, sarcoma, and leukemia or lymphoid malignancies. More particular examples of such cancers are noted below and include squamous cell cancer (e.g., epithelial squamous cell cancer), lung cancer (including small-cell lung cancer, non-small cell lung cancer, adenocarcinoma of the lung and squamous carcinoma of the lung), cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial cancer, uterine carcinoma, salivary gland carcinoma, kidney or renal cancer, prostate cancer, vulval cancer, thyroid cancer, hepatic carcinoma, anal carcinoma, penile carcinoma, as well as head and neck cancer. The term "cancer" includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor).

The methods described herein can be used to ablate and/or resect premalignant tissue and to prevent progression to a neoplastic or malignant state including, but not limited to, those disorders described above. Such uses are indicated in conditions known or suspected of preceding progression to neoplasia or cancer, in particular where non-neoplastic cell growth consisting of hyperplasia, metaplasia, or dysplasia has occurred (see, e.g., Robbins and Angell, *Basic Pathology*, 2d Ed., W.B. Saunders Co., Philadelphia, pp. 68-79 (1976)).

In addition to tumors and/or malignant tissue, the apparatus and methods described herein can also be used to identify premalignant tissue or hyperplastic tissue. The apparatus and methods described herein can further be used to identify premalignant tissue or hyperplastic tissue. Hyperplasia is a form of controlled cell proliferation, involving an increase in cell number in a tissue or organ, without significant alteration in structure or function. Hyperplastic disorders include, but are not limited to, angiofollicular mediastinal lymph node hyperplasia, angiolymphoid hyperplasia with eosinophilia, atypical melanocytic hyperplasia, basal cell hyperplasia, benign giant lymph node hyperplasia, cementum hyperplasia, congenital adrenal hyperplasia, congenital sebaceous hyperplasia, cystic hyperplasia, cystic hyperplasia of the breast, denture hyperplasia, ductal hyperplasia, endometrial hyperplasia, fibromuscular hyperplasia, focal epithelial hyperplasia, gingival hyperplasia, inflammatory fibrous hyperplasia, inflammatory papillary hyperplasia, intravascular papillary endothelial hyperplasia, nodular hyperplasia of prostate, nodular regenerative hyperplasia, pseudoepitheliomatous hyperplasia, senile sebaceous hyperplasia, and verrucous hyperplasia.

The apparatus and methods described herein can also be used to identify or ablate/resect metaplastic tissue. Metaplasia is a form of controlled cell growth in which one type of adult or fully differentiated cell substitutes for another type of adult cell. Metaplastic disorders include, but are not limited to, agnogenic myeloid metaplasia, apocrine metaplasia, atypical metaplasia, autoparenchymatous metaplasia, connective tissue metaplasia, epithelial metaplasia, intestinal metaplasia, metaplastic anemia, metaplastic ossification, metaplastic polyps, myeloid metaplasia, primary myeloid metaplasia, secondary myeloid metaplasia, squamous metaplasia, squamous metaplasia of amnion, and symptomatic myeloid metaplasia.

The apparatus and methods described herein can also be used to ablate/resect or identify dysplastic tissue. Dysplasia can be a forerunner of cancer and is found mainly in the epithelia. Dysplasia is a disorderly form of non-neoplastic cell growth, involving a loss in individual cell uniformity and in the architectural orientation of cells. Dysplastic cells can have abnormally large, deeply stained nuclei, and exhibit pleomorphism. Dysplasia can occur, e.g., in areas of chronic irritation or inflammation. Dysplastic disorders include, but are not limited to, anhidrotic ectodermal dysplasia, anterofacial dysplasia, asphyxiating thoracic dysplasia, atriodigital dysplasia, bronchopulmonary dysplasia, cerebral dysplasia, cervical dysplasia, chondroectodermal dysplasia, cleidocranial dysplasia, congenital ectodermal dysplasia, craniodiaphysial dysplasia, craniocarpotarsal dysplasia, craniometaphysial dysplasia, dentin dysplasia, diaphysial dysplasia, ectodermal dysplasia, enamel dysplasia, encephalo-ophthalmic dysplasia, dysplasia epiphysialis hemimelia, dysplasia epiphysialis multiplex, dysplasia epiphysialis *punctata*, epithelial dysplasia, faciodigitogenital dysplasia, familial fibrous dysplasia of the jaws, familial white folded dysplasia, fibromuscular dysplasia, fibrous dysplasia of bone, florid osseous dysplasia, hereditary renal-retinal dysplasia, hidrotic ectodermal dysplasia, hypohidrotic ectodermal dysplasia, lymphopenic thymic dysplasia, mammary dysplasia, mandibulofacial dysplasia, metaphysial dysplasia, Mondini dysplasia, monostotic fibrous dysplasia, mucoepithelial dysplasia, multiple epiphysial dysplasia, oculoauriculovertebral dysplasia, oculodentodigital dysplasia, oculovertebral dysplasia, odontogenic dysplasia, ophthalmomandibulomelic dysplasia, periapical cemental dysplasia, polyostotic fibrous dysplasia, pseudoachondroplastic spondyloepiphysial dysplasia, retinal dysplasia, septo-optic dysplasia, spondyloepiphysial dysplasia, and ventriculoradial dysplasia.

Additional pre-neoplastic tissue that can be identified by the apparatus and methods described herein include, but are not limited to, benign dysproliferative disorders (e.g., benign tumors, fibrocystic conditions, tissue hypertrophy, intestinal polyps, colon polyps, and esophageal dysplasia), leukoplakia, keratoses, Bowen's disease, Farmer's Skin, solar cheilitis, and solar keratosis.

The apparatus, methods, and systems described herein can also be used to ablate/resect or identify infected cells and/or tissues. In some embodiments, apparatus and methods described herein identify tissues infected with a virus, bacterium, fungus, protozoan, and/or helminth.

In some embodiments, infected tissue is infected with one or more of an immunodeficiency virus (e.g., a human immunodeficiency virus (HIV), e.g., HIV-1, HIV-2), a hepatitis virus (e.g., hepatitis B virus (HBV), hepatitis C virus (HCV), hepatitis A virus, non-A and non-B hepatitis virus), a herpes virus (e.g., herpes simplex virus type I (HSV-1), HSV-2, Varicella-zoster virus, Epstein Barr virus, human cytomegalovirus, human herpesvirus 6 (HHV-6), HHV-7, HHV-8), a poxvirus (e.g., variola, vaccinia, monkeypox, Molluscum contagiosum virus), an influenza virus, a human papilloma virus, adenovirus, rhinovirus, coronavirus, respiratory syncytial virus, rabies virus, coxsackie virus, human T-cell leukemia virus (types I, II and III), parainfluenza virus, paramyxovirus, poliovirus, rotavirus, rhinovirus, rubella virus, measles virus, mumps virus, adenovirus, yellow fever virus, Norwalk virus, West Nile virus, a Dengue virus, Severe Acute Respiratory Syndrome Coronavirus (SARS-CoV), bunyavirus, Ebola virus, Marburg virus, Eastern equine encephalitis virus, Venezuelan equine encephalitis virus, Japanese encephalitis virus, St. Louis encephalitis virus, Junin virus, Lassa virus, and Lymphocytic choriomeningitis virus.

In some embodiments, infected tissue is infected with one or more bacteria from the following genera and species: *Chlamydia* (e.g., *Chlamydia pneumoniae*, *Chlamydia psittaci*, *Chlamydia trachomatis*), *Legionella* (e.g., *Legionella pneumophila*), *Listeria* (e.g., *Listeria monocytogenes*), *Rickettsia* (e.g., *R. australis*, *R. rickettsii*, *R. akari*, *R. conorii*, *R. sibirica*, *R. japonica*, *R. africae*, *R. typhi*, *R. prowazekii*), *Actinobacter* (e.g., *Actinobacter baumannii*), *Bordetella* (e.g., *Bordetella pertussis*), *Bacillus* (e.g., *Bacillus anthracis*, *Bacillus cereus*), *Bacteroides* (e.g., *Bacteroides fragilis*), *Bartonella* (e.g., *Bartonella henselae*), *Borrelia* (e.g., *Borrelia burgdorferi*), *Brucella* (e.g., *Brucella abortus*, *Brucella canis*, *Brucella melitensis*, *Brucella suis*), *Campylobacter* (e.g., *Campylobacter jejuni*), *Clostridium* (e.g., *Clostridium botulinum*, *Clostridium difficile*, *Clostridium perfringens*, *Clostridium tetani*), *Corynebacterium* (e.g., *Corynebacterium diphtheriae*, *Corynebacterium amycolatum*), *Enterococcus* (e.g., *Enterococcus faecalis*, *Enterococcus faecium*), *Escherichia* (e.g., *Escherichia coli*), *Francisella* (e.g., *Francisella tularensis*), *Haemophilus* (e.g., *Haemophilus influenzae*), *Helicobacter* (e.g., *Helicobacter pylori*), *Klebsiella* (e.g., *Klebsiella pneumoniae*), *Leptospira* (e.g., *Leptospira interrogans*), *Mycobacteria* (e.g., *Mycobacterium leprae*, *Mycobacterium tuberculosis*), *Mycoplasma* (e.g., *Mycoplasma pneumoniae*), *Neisseria* (e.g., *Neisseria gonorrhoeae*, *Neisseria meningitidis*), *Pseudomonas* (e.g., *Pseudomonas aeruginosa*), *Salmonella* (e.g., *Salmonella typhi*, *Salmonella typhimurium*, *Salmonella enterica*), *Shigella* (e.g., *Shigella dysenteriae*, *Shigella sonnei*), *Staphylococcus* (e.g., *Staphylococcus aureus*, *Staphylococcus epidermidis*, *Staphylococcus saprophyticus*), *Streptococcus* (e.g., *Streptococcus agalactiae*, *Streptococcus pneumoniae*, *Streptococcus pyogenes*), *Treponoma* (e.g., *Treponoma pallidum*), *Vibrio* (e.g., *Vibrio cholerae*, *Vibrio vulnificus*), and *Yersinia* (e.g., *Yersinia pestis*).

In some embodiments, infected tissue is infected with one or more protozoa, for example, one or more of *Cryptosporidium parvum*, *Entamoeba* (e.g., *Entamoeba histolytica*), *Giardia* (e.g., *Giardia lambila*), *Leishmania* (e.g., *Leishmania donovani*), *Plasmodium* spp. (e.g., *Plasmodium falciparum*, *Plasmodium vivax*, *Plasmodium ovale*, *Plasmodium malariae*), *Toxoplasma* (e.g., *Toxoplasma gondii*), *Trichomonas* (e.g., *Trichomonas vaginalis*), and *Trypanosoma* (e.g., *Trypanosoma brucei*, *Trypanosoma cruzi*).

In some embodiments, infected tissue is infected with one or more fungal pathogens such as *Aspergillus*, *Candida* (e.g., *Candida albicans*), *Coccidiodes* (e.g., *Coccidiodes immitis*), *Cryptococcus* (e.g., *Cryptococcus neoformans*), *Histoplasma* (e.g., *Histoplasma capsulatum*), and *Pneumocystis* (e.g., *Pneumocystis carinii*).

In some embodiments, infected tissue is infected with one or more helminths, such as *Ascaris lumbricoides*, *Ancylostoma*, *Clonorchis sinensis*, *Dracuncula medinensis*, *Enterobius vermicularis*, *Filaria*, *Onchocerca volvulus*, *Loa loa*, *Schistosoma*, *Strongyloides*, *Trichuris trichura*, and *Trichinella spiralis*.

Computer/Software

Embodiments may include a computer which executes software that controls the operation of one or more instruments/devices, and/or that processes data obtained by the system. The software may include one or more modules recorded on machine-readable media such as magnetic disks, magnetic tape, CD-ROM, and semiconductor memory, for example. The machine-readable medium may be resident within the computer or can be connected to the computer by a communication link (e.g., access via internet link). However, in alternative embodiments, one can substitute computer instructions in the form of hardwired logic for software, or one can substitute firmware (i.e., computer instructions recorded on devices such as PROMs, EPROMS, EEPROMs, or the like) for software. The term machine-readable instructions as used herein is intended to encompass software, hardwired logic, firmware, object code and the like.

The computer can be, for example, a general purpose computer. The computer can be, for example, an embedded computer, a personal computer such as a laptop or desktop computer, or another type of computer, that is capable of running the software, issuing suitable control commands, and/or recording information in real-time. The computer may include a display for reporting information to an operator of the system/device (e.g., displaying a view field to a surgeon during an operation), a keyboard and/or other I/O device such as a mouse for enabling the operator to enter information and commands, and/or a printer for providing a print-out. In certain embodiments, some commands entered at the keyboard enable a user to perform certain data processing tasks.

Auxiliary Imaging Systems

The Raman-based systems, methods, and devices described herein that are utilized in a surgical or non-surgical procedure may be used in combination with other imaging systems implemented before, during, or after the procedure. For example, the Raman-based systems, methods, and devices may be used in combination with video, microscope, x-ray, Computed Tomography (CT), magnetic resonance imaging (MRI), ultrasound (US), thermography, fluorescence imaging, Diffuse Optical Tomography (DOT), Positron Emission Tomography (PET), PET/CT, Single Photon Emission Computed Tomography (SPECT), and/or SPECT/CT systems.

In some embodiments, a target tissue (e.g., diseased tissue) is imaged using an auxiliary imaging system, and the image can be used to guide a Raman ablation system described herein to the target tissue. In some embodiments, an auxiliary imaging system includes hardware and/or software for co-registering the image with detected Raman signals. For example, a video camera can be used in conjunction with the Raman system described herein, such that the video camera provides an image that serves to identify locations at which the ablation or resection device is inoperative (regardless of the presence of a Raman reporter at such location). Furthermore, other detection modalities, such as MRI, NMR, PET, SPECT, CT, X-ray, ultrasound, photoacoustic detection, and/or fluorescent detection can be used in conjunction with the Raman systems described herein to identify tissue to be resected/ablated.

EQUIVALENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

We claim:

1. A system comprising:
a Raman particle to be administered to a subject, wherein the Raman particle is a Surface Enhanced Resonance Raman Scattering (SERRS) nanoparticle comprising a nanoscale substrate, a capping agent associated with the substrate, and a Raman active agent, wherein the capping agent is a member selected from the group consisting of a citrate, a citric acid, an ascorbic acid, an ascorbate, a palmitoylascorbate, a tetrakis(hydroxymethyl)phosphonium chloride, and an amino acid, and the Raman active agent is characterized by sufficient affinity for the nanoscale substrate to permit displacement of the capping agent, thereby providing a high density and localized loading of the Raman active agent onto the Raman particle, such that the Raman active agent is in direct contact with the nanoscale substrate and positioned a distance between 1 nm and 10 nm from the nanoscale substrate;
an ablation laser for directing electromagnetic radiation onto or into a scanning point of a target tissue of the subject containing the administered Raman particle;
an instrument operably linked to the ablation laser, the instrument comprising optics for directing the electromagnetic radiation onto or into the scanning point of the target tissue of the subject containing the administered Raman particle;
a detector for detecting scattered photons emanating from the scanning point of the target tissue of the subject containing the administered Raman particle, said scattered photons resulting from illumination with the electromagnetic radiation; and
a processor configured to regulate output power levels of the ablation laser and to process data corresponding to the scattered photons detected from the scanning point of the target tissue of the subject containing the administered Raman particle,
the processor being configured to trigger a switch from an interrogation power level of the ablation laser to an ablation power level of the ablation laser upon a determination of a presence of the administered Raman particle in the target tissue of the subject in and/or upon the scanning point, the ablation power level being sufficient to ablate tissue at the scanning point.

2. The system of claim 1, wherein the electromagnetic radiation has a wavelength of about 500 nm to about 11 μm.

3. The system of claim 1, wherein the instrument is an endoscopic instrument.

4. The system of claim 1, wherein the ablation laser is selected from the group consisting of a $CO_2$ laser, an Er:YAG laser, and a Nd:YAG laser.

5. The system of claim 1, wherein the instrument comprises optics for imaging.

6. The system of claim 1 further comprising a suction vacuum operably linked to the instrument.

7. The system of claim 1, wherein the interrogation power level is less than 10% of the maximum power level of the ablation laser.

8. The system of claim 1, wherein the ablation power level is greater than 50% of the maximum power level of the ablation laser.

9. The system of claim 1, wherein the processor determines whether the acquired signal is indicative of the presence of the Raman reporter in and/or upon the scanning point by:
determining a comparison index between the acquired signal and a referenced signal of the administered Raman particle; and
evaluating the determined comparison index to determine if the index exceeds a pre-defined threshold.

10. The system of claim 1, comprising:
a raster scanning device for positioning the instrument over the target tissue.

11. The system of claim 1, wherein, upon the determination of the presence of the Raman particle in and/or upon the scanning point, the ablation power level of the ablation laser is at a power level that does not cause damage to tissue exposed to electromagnetic radiation at the ablation power level unless the Raman particle is present therein or thereupon.

12. The system of claim 1, wherein the Raman particle can be detected at a sensitivity of $10^{-12}$ M or better.

13. The system of claim 1, wherein the capping agent comprises a citrate.

14. The system of claim 1, wherein the excitation light is in the visible to near infrared range.

15. The system of claim 1, wherein the excitation light is near infrared.

16. The system of claim 1, wherein the nanoscale substrate comprises a member selected from the group consisting of gold, silver, copper, sodium, potassium, chromium, aluminum, and lithium.

17. The system of claim 1, wherein the nanoscale substrate has a spherical shape.

18. The system of claim 1, wherein the nanoscale substrate has a non-spherical shape.

19. The system of claim 18, wherein the non-spherical shape of the nanoscale substrate or a cross-section thereof is a member selected from the group consisting of a rod, a star, a shell, an ellipse, a triangle, a pyramid, a cube, and a cage.

20. The system of claim 1, wherein the excitation light source produces near infrared excitation light having a frequency that is in resonance with a major absorption band of the SERRS nanoparticle.

21. The system of claim 20, wherein the excitation light source is a laser that produces near infrared light.

22. The system of claim 1, wherein the excitation light source produces visible excitation light having a frequency that is in resonance with a major absorption band of the SERRS nanoparticle.

23. The system of claim 22, wherein the excitation light source is a laser that produces visible light.

24. The system of claim 1, wherein the Raman active agent is in direct contact with the nanoscale substrate and positioned a distance between 1 nm and 3 nm from the nanoscale substrate.

25. The system of claim 1, wherein the Raman particle comprises a layer that encapsulate the nanoscale substrate, wherein the layer comprises silica.

26. The system of claim 25, wherein the layer has an average thickness between greater than or equal to 10 nm and less than or equal to 30 nm.

27. The system of claim 26, wherein the layer has an average thickness between greater than or equal to 20 nm and less than or equal to 30 nm.

28. The system of claim 1, wherein the Raman active agent comprises a phthalocyanine, a naphthalocyanine, a chalcogen-based dye, an azomethine, a squaraine, and/or a xanthine.

\* \* \* \* \*